United States Patent
Ishikawa et al.

(10) Patent No.: US 9,959,982 B2
(45) Date of Patent: May 1, 2018

(54) PHOTOELECTRIC CONVERSION ELEMENT AND METHOD FOR PRODUCING THE SAME

(71) Applicant: Konica Minolta, Inc., Tokyo (JP)

(72) Inventors: Takayuki Ishikawa, Tokyo (JP); Kazuya Isobe, Tokyo (JP)

(73) Assignee: KONICA MINOLTA, INC., Tokyo (JP)

( * ) Notice: Subject to any disclaimer, the term of this patent is extended or adjusted under 35 U.S.C. 154(b) by 372 days.

(21) Appl. No.: 14/430,407

(22) PCT Filed: Sep. 18, 2013

(86) PCT No.: PCT/JP2013/075194
§ 371 (c)(1),
(2) Date: Mar. 23, 2015

(87) PCT Pub. No.: WO2014/046145
PCT Pub. Date: Mar. 27, 2014

(65) Prior Publication Data
US 2015/0243445 A1 Aug. 27, 2015

(30) Foreign Application Priority Data

Sep. 24, 2012 (JP) .................................. 2012-209702
Feb. 13, 2013 (JP) .................................. 2013-025881

(51) Int. Cl.
*H01L 31/00* (2006.01)
*H01G 9/20* (2006.01)
(Continued)

(52) U.S. Cl.
CPC ......... *H01G 9/2059* (2013.01); *C07D 495/04* (2013.01); *C08G 61/126* (2013.01);
(Continued)

(58) Field of Classification Search
None
See application file for complete search history.

(56) References Cited

U.S. PATENT DOCUMENTS 6,291,763 B1 * 9/2001 Nakamura ........... H01G 9/2009
136/252
2005/0132562 A1 * 6/2005 Saito .................... H01M 4/0404
29/623.5

(Continued)

FOREIGN PATENT DOCUMENTS

JP H01-123228 A 5/1989
JP 3-134018 A 6/1991
(Continued)

OTHER PUBLICATIONS

Extended European Search Report dated May 18, 2016 from the corresponding European Application; Application No./ Patent No. 13838385.6-1555 / 2899799 PCT/JP2013075194; Applicant: Konica Minolta, Inc.; Total of 10 pages.
(Continued)

*Primary Examiner* — Eli Mekhlin
(74) *Attorney, Agent, or Firm* — Lucas & Mercanti, LLP

(57) ABSTRACT

To provide a photoelectric conversion element being excellent in photoelectric conversion efficiency and stability of photoelectric conversion function, a method for producing the photoelectric conversion element, and a solar cell using the photoelectric conversion element. A photoelectric conversion element having a substrate, a first electrode, a photoelectric conversion layer containing a semiconductor and a sensitizing pigment, a hole transport layer having a conductive polymer, and a second electrode, wherein the hole transport layer is formed by bringing the photoelectric conversion layer into contact with a solution containing a conductive polymer precursor and an oxidizer at a ratio of $0.1<[Ox]/[M]$ (wherein [Ox] is the molar concentration of
(Continued)

the oxidizer; and [M] is the molar concentration of the conductive polymer precursor), and irradiating the photoelectric conversion layer with light.

17 Claims, 1 Drawing Sheet

(51) Int. Cl.
| | | |
|---|---|---|
| *C07D 495/04* | (2006.01) | |
| *C09B 57/00* | (2006.01) | |
| *C08G 61/12* | (2006.01) | |
| *C09B 5/62* | (2006.01) | |
| *C09B 23/01* | (2006.01) | |
| *C09B 23/10* | (2006.01) | |
| *C09B 23/14* | (2006.01) | |
| *C09B 69/00* | (2006.01) | |
| *H01L 51/42* | (2006.01) | |
| *H01L 51/00* | (2006.01) | |

(52) U.S. Cl.
CPC .............. *C09B 5/62* (2013.01); *C09B 23/005* (2013.01); *C09B 23/0058* (2013.01); *C09B 23/0066* (2013.01); *C09B 23/0075* (2013.01); *C09B 23/105* (2013.01); *C09B 23/107* (2013.01); *C09B 23/145* (2013.01); *C09B 23/148* (2013.01); *C09B 57/00* (2013.01); *C09B 57/008* (2013.01); *C09B 69/008* (2013.01); *H01L 51/0036* (2013.01); *H01L 51/0061* (2013.01); *H01L 51/4226* (2013.01); *C08G 2261/1424* (2013.01); *C08G 2261/3223* (2013.01); *C08G 2261/91* (2013.01); *H01L 51/0037* (2013.01); *H01L 51/0068* (2013.01); *Y02E 10/549* (2013.01); *Y02P 70/521* (2015.11)

(56) References Cited

U.S. PATENT DOCUMENTS

| | | |
|---|---|---|
| 2006/0206985 A1 | 9/2006 | Proctor |
| 2006/0266411 A1 | 11/2006 | Sugiyama et al. |
| 2012/0042953 A1* | 2/2012 | Nishimura .......... H01L 51/0037 136/263 |
| 2012/0060927 A1 | 3/2012 | Onaka et al. |
| 2012/0085411 A1 | 4/2012 | Isobe et al. |
| 2012/0104308 A1* | 5/2012 | Okamoto ........... C08G 73/0266 252/62.2 |
| 2012/0152356 A1 | 6/2012 | Ishikawa et al. |

FOREIGN PATENT DOCUMENTS

| | | |
|---|---|---|
| JP | 2003142168 A | 5/2003 |
| JP | 2004063758 A | 2/2004 |
| JP | 2008-531570 A | 8/2008 |
| JP | 2009-108175 A | 5/2009 |
| JP | 2010-021217 A | 1/2010 |
| JP | 2012-043640 A | 3/2012 |
| JP | 2012064332 A | 3/2012 |
| JP | 2012144688 A | 8/2012 |
| JP | 2013145677 A | 7/2013 |
| JP | 2013186996 A | 9/2013 |
| WO | 2005078853 A1 | 8/2005 |
| WO | 2007007735 A1 | 1/2007 |

OTHER PUBLICATIONS

Article by Norihiro Fukuri e al; "Electron Transport Analysis for improvement of Solid-State Dye-Sensitized Solar Cells Using Poly (3, 4-ethylenedioxythiophene) as Hole Conductors +", Journal of Physical Chemistry Part B; Condensed Matter, Materials, Surfaces, Interfaces & Biophysical, vol. 110, No. 50, Oct. 12, 2006, pp. 25251-25258.
International Preliminary Report on Patentability dated Apr. 2, 2015 for PCT Application No. PCT/JP2013/075194 and English translation.
International Search Report dated Oct. 29, 2013 for Application No. PCT/JP2013/075194 with English Translation.
Notification of Reasons for Refusal dated Jun. 27, 2017 from corresponding Japanese Patent Application No. JP 2014-536885 and English translation.
Chemicals great dictionary member-of-editorial-board meeting, chemicals large encyclopedia 3 miniature edition, 1960, p. 910 (Document showing a well-known technique).

\* cited by examiner

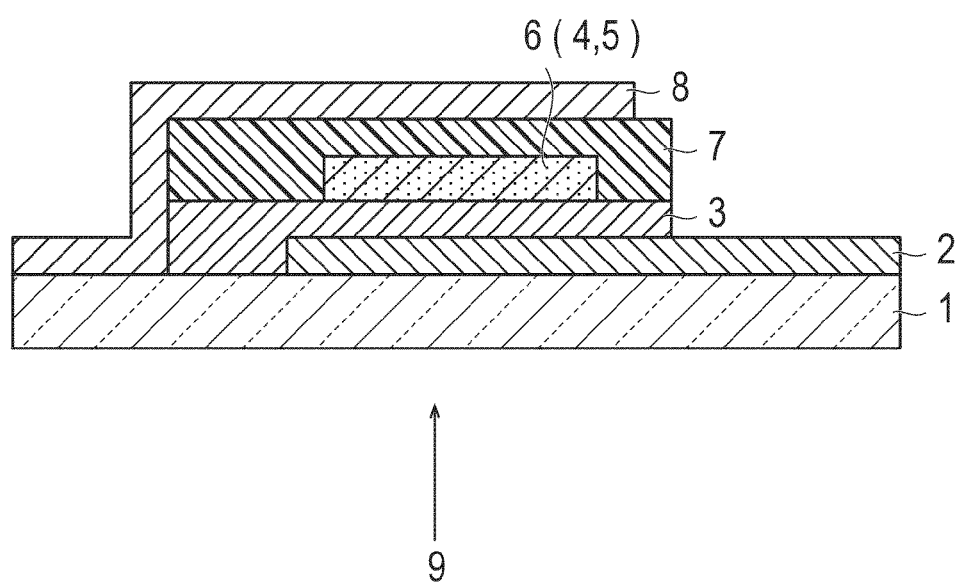

PHOTOELECTRIC CONVERSION ELEMENT AND METHOD FOR PRODUCING THE SAME

CROSS REFERENCE TO RELATED APPLICATION

This Application is a 371 of PCT/JP2013/075194 filed on Sep. 18, 2013 which, in turn, claimed the priority of Japanese Patent Application No. JP2012-209702 filed on Sep. 24, 2012 and Japanese Patent Application No. JP2013-025881 filed on Feb. 13, 2013, all applications are incorporated herein by reference.

TECHNICAL FIELD

The present invention relates to a photoelectric conversion element and a solar cell constituted by using the photoelectric conversion element, and production methods therefor.

BACKGROUND ART

In recent years, solar power generation technologies in which solar energy, which is one of renewable energies, is used without using fossil fuels, as a means for solving the problem of global warming, have gained attention. Among the solar power generation technologies, a pigment-sensitized solar cell attracts lots of attention as one of inexpensive, high-performance roof-top type solar cells that are responsible for the next generation, since it generates electricity by a similar mechanism to that of light-induced electron transfer conducted by a chlorophyll pigment.

A general constitution of such pigment-sensitized solar cell is such that a substrate, a first electrode, a semiconductor layer on which a sensitizing pigment is carried (a photoelectric conversion layer), a hole transport layer, and a second electrode are stacked in this order. For example, the technology for a pigment-sensitized solar cell includes Patent Literature 1. This Patent Literature 1 discloses a photoelectric conversion element including a second electrode in which platinum is supported on a transparent conductive glass plate coated with fluorine-doped tin oxide as a counter electrode for electrolysis, and an electrolytically-polymerized aniline film is formed on the counter electrode by leaving a predetermined size of a platinum part on the central part of the electrode surface, masking the other parts by a imide-based resin tape, and immersing the counter electrode in an acidic aqueous solution including aniline and hydrogen fluoroborate, and energizing the counter electrode at a predetermined current density, and a production method therfor, and a photoelectric conversion element formed by immersing this electrolytically-polymerized film of aniline in a liquid electrolyte, and a production method therefor.

Furthermore, in the case when an electrolyte is used as in the above-mentioned Patent Literature 1, the leaking or depletion of the electrolyte may occur, and thus there are technologies using a solid electrolyte as a hole transport layer. In Patent Literature 2, which is one of the technologies, discloses that a mesoporous titanium dioxide porous layer, which is a photoelectric conversion layer, is immersed in an acetonitrile solution in which pyrrole and $LiClO_4$ are dissolved, the retention voltage is set to 250 mV, platinum is used as a counter electrode, $Ag/Ag^+$ is used as a reference electrode, light is irradiated, and the voltage is retained until the polymerization electrical charge amount becomes a predetermined value, and also discloses a photoelectric conversion element in which a polypyrrole layer as a hole transport layer is formed onto the layer surface of the above-mentioned photoelectric conversion layer and a production method therefor.

CITATION LIST

Patent Literature

Patent Literature 1: WO 2005/078853
Patent Literature 2: JP 2003-142168 A

SUMMARY OF INVENTION

The hole transport layer in the above-mentioned pigment-sensitized solar cell is formed by electrolytic polymerization in Patent Literature 1, and is formed by photoelectrolysis (photoelecrochemical oxidation polymerization) in Patent Literature 2. In general, an electrolytic polymerization process is frequently adopted as one of methods for synthesizing a conductive polymer, and is a method for forming a polymer, in which an electrode pair is immersed in a solution in which a monomer and a support electrolyte are dissolved and a voltage is applied to the electrode pair, whereby the monomer is oxidized or reduced on the surface of the electrode. From the viewpoint that pn can be controlled at this time since the counterions in the solution can be uptaken on the electrode by electrochemical doping, electrolytic polymerization is adopted to a method for forming a hole transport layer in the field of pigment-sensitized solar cells.

However, in order to form a hole transport layer by electrolytic polymerization such as photoelectrolytic polymerization, a long time is required for the polymerization, and the amount of polymerization is small. In a method in which an aniline film that serves as a substrate for a hole transport layer is electrolytically polymerized on a second electrode as a counter electrode, and the aniline film is then attached to a substrate having a pigment-containing semiconductor film and a transparent conductive film as in the above-mentioned Patent Literature 1, there is a problem that the pigment cannot be sufficiently covered with the aniline film. Furthermore, in a method in which a polypyrrole layer is directly formed on a photoelectric conversion layer as in the above-mentioned Patent Literature 2, there is a problem that the monomer solution is difficult to completely permeate into the mesoporous as a photoelectric conversion layer, and thus a polypyrrole layer in an amount that is sufficient to cover the pigment cannot be formed.

Furthermore, in the case when a hole transport layer is formed by electrolytic polymerization such as photoelectrolytic polymerization, it is necessary to apply a voltage as mentioned above, whereas in a method in which a polypyrrole layer is directly formed on a photoelectric conversion layer as in Patent Literature 2, it is necessary to conduct polymerization under a low voltage so that the pigment is not oxidized (deteriorated). However, when the polymerization of a polymer that constitutes a hole transport layer at a low potential is conducted, descending of voltage occurs together with the precipitation of the polymer, and thus there is a problem that a sufficient potential for oxidizing or reducing the monomer is not applied to the surface of the electrode and thus it is difficult to form a sufficient amount of polymer around the pigment.

Furthermore, it was necessary to conduct polymerization at a lower potential as mentioned above in photoelectrolytic polymerization, and thus there is a problem that a long time is required for the polymerization and thus the producibility is low. In addition, in the case when increasing in the surface area of a photoelectric conversion element is considered, it is difficult to homogeneously apply a potential in photoelectrolytic polymerization due to the high resistance of the electrode itself such as FTO, and thus it was difficult to homogeneously form a hole transport layer on the entirety of a photoelectric conversion element, and thus there is a problem that the light durability of the photoelectric conversion element is low.

Therefore, in order to improve such problems, the present inventors aim at providing a photoelectric conversion element having a homogeneously-formed hole transport layer, a method for producing the photoelectric conversion element, and a solar cell.

The present invention can achieve the above-mentioned object by a photoelectric conversion element including a substrate, a first electrode, a photoelectric conversion layer containing a semiconductor and a sensitizing pigment, a hole transport layer having a conductive polymer, and a second electrode, wherein the hole transport layer is formed by bringing the photoelectric conversion layer into contact with a conductive polymer precursor in the presence of an oxidizer, and irradiating the above-mentioned sensitizing pigment with light to polymerize the conductive polymer precursor.

BRIEF DESCRIPTION OF DRAWINGS

FIG. 1 is a schematic cross-sectional drawing showing an example of the photoelectric conversion element of the present invention. In FIG. 1, 1 represents a substrate; 2 represents a first electrode; 3 represents a buffer layer; 4 represents a sensitizing pigment; 5 represents a semiconductor; 6 represents a photoelectric conversion layer; 7 represents a hole transport layer; 8 represents a second electrode; 9 represents the incidence direction of solar light; and 10 represents a photoelectric conversion element, respectively.

DESCRIPTION OF EMBODIMENTS

The preferable embodiments of the present invention will be explained below.

The first of the present invention is a photoelectric conversion element having a substrate, a first electrode, a photoelectric conversion layer containing a semiconductor and a sensitizing pigment, a hole transport layer having a conductive polymer, and a second electrode, wherein the hole transport layer is formed by bringing the photoelectric conversion layer into contact with a conductive polymer precursor in the presence of an oxidizer, and irradiating the above-mentioned sensitizing pigment with light to polymerize the conductive polymer precursor. By adopting the above-mentioned constitution, the photoelectric conversion element according to the present invention forms the hole transport layer by bringing a solution containing the conductive polymer precursor and the oxidizer into contact with the photoelectric conversion layer, and then conducting photochemical polymerization; therefore, the photoelectric conversion element has a hole transport layer that is more homogeneous than a hole transport layer formed by conventional (photo)electrolytic polymerization, and thus an element having high durability can be prepared. It is preferable that the above-mentioned conductive polymer precursor and oxidizer are brought into contact at a ratio of the following mathematical formula (1):

[Math. 1]

$$0.1 < [Ox]/[M] \tag{1}$$

wherein in the mathematical formula (1), [Ox] is the molar concentration of the oxidizer; and [M] is the molar concentration of the conductive polymer precursor.

As mentioned above, hole transport layers were formed by electrolytic polymerization such as photoelectrolytic polymerization in the past; however, a homogeneous polymerized film was difficult to be obtained, and there was a problem in the light durability of a photoelectric conversion element. Furthermore, photochemical polymerization of an oxidation polymerizable monomer using an oxidizer and a photosensitizer has also been conventionally known (for example, JP H1-123228 A, JP 2009-16582 A). However, in this polymerization process, the molar ratio of the oxidizer to the monomer is small and thus the reactivity is poor, and thus there was a problem that it is difficult to form a sufficient film that is required for a photoelectric conversion element for a photoelectric conversion element, especially a pigment-sensitizing solar cell, and thus the light durability of the photoelectric conversion element is low.

In response to this, in the present invention, the sensitizing pigment is excited by irradiation of light, and the excited electrons are consumed by the oxidizer (for example, hydrogen peroxide). By this way, the sensitizing pigment is put into a cation state, and the sensitizing pigment in a cation state withdraws electrons from the conductive polymer precursor, whereby the conductive polymer precursor is put into a cation state. The conductive polymer precursor that has been put into a cation state acts as a trigger, whereby polymerization is initiated. Meanwhile, according to the present invention, since the sensitizing pigment in a cation state efficiently withdraws electrons from the conductive polymer precursor, the polymerization can be initiated more quickly by using the conductive polymer precursor that has been put into a cation state as a trigger, by mixing the oxidizer and conductive polymer precursor at such a ratio that the oxidizer exists at a higher concentration than that of the conductive polymer precursor. Since the above-mentioned process progresses very quickly as compared to a process of electrolytic polymerization, it is possible to shorten the polymerization time, and this is very advantageous in simplifying the production process. Furthermore, it is also possible to easily form a hole transport layer having a large surface area by the above-mentioned process.

Furthermore, according to the present invention, since the sensitizing pigment promotes polymerization while exerting an action as a polymerization initiator to thereby form a hole transport layer containing a conductive polymer, the sensitizing pigment is difficult to peel off from the photoelectric conversion layer due to causes such as an outer voltage and solvation, and thus a photoelectric conversion element having an excellent photoelectric conversion efficiency, and a solar cell can be provided.

Furthermore, the method for producing the photoelectric conversion element includes a method for producing a photoelectric conversion element having a substrate, a first electrode, a photoelectric conversion layer containing a semiconductor and a sensitizing pigment, a hole transport layer having a conductive polymer, and a second electrode, the method including the steps of: step (1): forming the photoelectric conversion layer on the substrate including the first electrode on the surface, step (2): bringing the conductive polymer precursor into contact with the photoelectric conversion layer in the presence of an oxidizer, step (3): irradiating the sensitizing pigment with light in the presence of the oxidizer to polymerize the conductive polymer precursor to thereby form the hole transport layer, and step (4): forming the second electrode on the hole transport layer. In the above-mentioned step (2), it is preferable that the above-mentioned conductive polymer precursor and oxidizer are brought into contact at a ratio of the following mathematical formula (1):

[Math. 2]

$$0.1 < [Ox]/[M] \qquad (1)$$

wherein in the mathematical formula (1), [Ox] is the molar concentration of the oxidizer; and [M] is the molar concentration of the conductive polymer precursor. Furthermore, in the step (3), it is preferable that the hole transport layer has entered into the photoelectric conversion layer formed of the semiconductor carrying the sensitizing pigment, and is present thereon, and the second electrode has attached onto the hole transport layer. Therefore, as mentioned below, the semiconductor layer is preferably a porous body. Furthermore, a current can be taken out by attaching terminals to the first electrode and second electrode.

{Photoelectric Conversion Element}

A preferable constitution of the photoelectric conversion element according to the present invention will be explained with referring to FIG. 1. FIG. 1 is a schematic cross-sectional drawing showing an example of the photoelectric conversion element of the present invention. As shown in FIG. 1, the photoelectric conversion element 10 is constituted by substrate 1, first electrode 2, buffer layer 3, photoelectric conversion layer 6, hole transport layer 7 and second electrode 8 as a counter electrode. The photoelectric conversion layer 6 contains semiconductor 5 and sensitizing pigment 4. As shown in FIG. 1, the buffer layer 3 may be formed as necessary between the first electrode 2 and the photoelectric conversion layer 6 for the purposes of prevention of short-circuit, sealing and the like. In FIG. 1, the solar light enters from the direction of arrow 9 on the lower position of the drawing, but the present invention is not limited to this embodiment, and solar light may enter from the upper side of the drawing.

The photoelectric conversion element according to the present invention has a structure in which the substrate, the first electrode, the photoelectric conversion layer, the hole transport layer and the second electrode as a counter electrode are stacked in this order as essential constitutional elements, and where necessary, a buffer layer may be formed between the substrate and the first electrode, and/or a buffer layer may be formed on the surface of the second electrode. Hereinafter the respective constitutional elements of the photoelectric conversion element according to the present invention, and the method for producing the photoelectric conversion element according to the present invention will be explained.

"Substrate"

The substrate in the present invention is disposed on the side of the light incidence direction, and is preferably a transparent substrate and is more preferably a transparent conductive substrate having the first electrode formed on the surface, and the substrate has a light transmittance of more preferably 10% or more, further more preferably 50% or more, and especially preferably from 80% to 100%, in view of the photoelectric conversion efficiency of the photoelectric conversion element.

The light transmittance refers to a total light transmittance in the visible light wavelength region measured by a method based on "Method for testing total light transmittance of plastic-transparent material" in JIS K 7361-1: 1997 (this corresponds to ISO 13468-1: 1996).

The material, shape, structure, thickness, hardness and the like of the substrate can be suitably selected from known ones, but it is preferable that the substrate has high light transmittivity as mentioned above.

The substrate can be roughly classified into rigid substrates such as glass plates and acrylic plates, and flexible substrates such as film substrates. Among the former rigid substrates, glass plates are preferable in view of heat resistance, and the kind of glass is not especially questioned. The thickness of the substrate is preferably from 0.1 to 100 mm, further preferably from 0.5 to 10 mm.

Examples of the latter flexible substrates can include polyester-based resin films such as polyethylene telephthalate (PET), polyethylene naphthalate and modified polyesters, polyolefin resin films such as polyethylene (PE) resin films, polypropylene (PP) resin films, polystyrene resin films and cyclic olefin-based resins, vinyl-based resin films such as polyvinyl chloride and polyvinylidene chloride, polyvinyl acetal resin films such as polyvinyl butyral (PVB), polyether ether ketone (PEEK) resin films, polysulfone (PSF) resin films, polyethersulfone (PES) resin films, polycarbonate (PC) resin films, polyamide resin films, polyimide resin films, acrylic resin films, triacetylcellulose (TAC) resin films, and the like. Besides these resin films, inorganic glass films may also be used as the substrate. The thickness of the substrate is preferably from 1 to 1,000 μm, further preferably from 10 to 100 μm.

Any resin film having a transmittance at a wavelength in the visible region (400 to 700 nm) of 80% or more can be especially and preferably applied to the present invention.

Specifically, from the viewpoints of transparency, heat-resistance, easiness of handling, intensity and cost, a biaxially-stretched polyethylene telephthalate film, a biaxially-stretched polyethylene naphthalate film, a polyethersulfone film or a polycarbonate film is preferable, and a biaxially-stretched polyethylene telephthalate film or a biaxially-stretched polyethylene naphthalate film is more preferable.

These substrates can be subjected to a surface treatment, or an easily adhesive layer can be disposed on these substrates so as to ensure wettability for an application liquid and adhesiveness.

For the surface treatment and easily adhesive layer, conventionally-known technologies can be used. Examples of the surface treatment can include surface activation treatments such as a corona discharging treatment, a flame treatment, an ultraviolet treatment, a high frequency treatment, a glow discharge treatment, an active plasma treatment and a laser treatment.

Furthermore, examples of the easily adhesive layer include polyesters, polyamides, polyurethanes, vinyl-based copolymers, butadiene-based copolymers, acrylic-based copolymers, vinilidene-based copolymers, epoxy-based copolymers and the like.

"First Electrode"

The first electrode in the present invention is disposed between the substrate and the photoelectric conversion layer. The first electrode is disposed on one surface of the substrate which becomes the opposite side of the light incidence direction. As the first electrode, one having a light transmittance of 80% or more, further 90% or more (upper limit: 100%) is preferably used. The light transmittance is similar to that described in the above-mentioned explanation on the substrate.

The material that forms the first electrode is not especially limited, and known materials can be used. Examples include metals such as platinum, gold, silver, copper, aluminum, rhodium and indium; and $SnO_2$, CdO, ZnO, CTO systems ($CdSnO_3$, $Cd_2SnO_4$, $CdSnO_4$), $In_2O_3$, $CdIn_2O_4$ and the like, and metal oxides thereof, and the like. Among these, silver is preferably exemplified as the metal, and a grid-patterned film having openings, or a film formed by dispersing microparticles or nanowires and applying the dispersion is preferably used so as to impart light transmittivity. Furthermore, preferable examples of the metal oxides include composite (doped) materials formed by adding one kind or two or more kinds selected from Sn, Sb, F and Al to the above-mentioned metal oxides. More preferably, conductive metal oxides such as Sn-doped $In_2O_3$ (ITO), Sb-doped $SnO_2$ and F-doped $SnO_2$ (FTO) are preferably used, and FTO is the most preferable in view of heat resistance. The application amount of the material that forms the first electrode onto the substrate is not especially limited, and is preferably about 1 to 100 g per 1 $m^2$ of the substrate.

The first electrode in the present invention is preferably a transparent conductive substrate disposed on the surface of a transparent substrate as a substrate, and the substrate having the first electrode formed on the surface is herein also referred to as a transparent conductive substrate (or a first electrode substrate).

The average thickness of the transparent conductive substrate is not especially limited, and is preferably in the range of from 0.1 mm to 5 mm. Furthermore, the transparent conductive substrate has a surface resistance of preferably 50 $\Omega/cm^2$ ($\square$(square)) or less, more preferably 20$\Omega/\square$ (square) or less, and further preferably 10$\Omega/\square$ (square) or less. In addition, although the lower limit of the surface resistance of the transparent conductive substrate is preferably low as possible, and thus it is not necessary to define the lower limit, it is sufficient that the lower limit is 0.01$\Omega/\square$ (square) or more. The preferable range of the light transmittance of the transparent conductive substrate is similar to the preferable range of the light transmittance of the above-mentioned substrate.

"Second Electrode"

The second electrode in the present invention may be any one having conductivity, and an optional conductive material is used. An insulating substance can also be used as long as a conductive substance layer is installed on the side facing to the hole transport layer. Furthermore, it is preferable that the second electrode has fine contact property with the hole transport layer. It is also preferable that the second electrode has a small difference in work functions from the hole transport layer and thus is chemically stable. Such material is not especially limited, and examples include metal thin films of gold, silver, copper, aluminum, platinum, rhodium, magnesium, indium and the like, carbon, carbon black, organic conductive bodies such as conductive polymer and conductive metal oxides (indium-tin composite oxide, fluorine-doped tin oxide and the like), and the like. Furthermore, the average thickness of the second electrode is also not especially limited, and is preferably from 10 to 1,000 nm. Furthermore, the surface resistance of the second electrode is not especially limited, and is preferably low. Specifically, the range of the surface resistance of the second electrode is preferably 80$\Omega/\square$ (square) or less, further preferably 20$\Omega/\square$ (square) or less. In addition, although the lower limit of the surface resistance of the second electrode is preferably low as possible, and thus it is not necessary to define the lower limit, it is sufficient that the lower limit is 0.01$\Omega/\square$ (square) or more.

"Buffer Layer"

The photoelectric conversion element according to the present invention preferably has a buffer layer that has a film shape (laminar shape) and is disposed between the first electrode and the photoelectric conversion layer (semiconductor layer) as a means for preventing short-circuit and as a rectification action.

In a preferable embodiment, the buffer layer and photoelectric conversion layer in the present invention are porous as mentioned below, and in this case, when the porosity of the buffer layer is C [%] and the porosity of the semiconductor layer is D [%], for example, D/C is preferably about 1.1 or more, more preferably about 5 or more, and further preferably about 10 or more. Since the upper limit of D/C is preferably high as possible, it is not necessary to especially define the upper limit, but the upper limit is generally about 1,000 or less. By this way, the buffer layer and semiconductor layer can exert their functions respectively in more preferable ways.

More specifically, for example, the porosity C of the buffer layer is preferably about 20% by volume or less, more preferably about 5% by volume or less, and further preferably 2% by volume or less. In other words, the buffer layer is preferably a fine layer. By this way, effects such as prevention of short-circuit and a rectification action can further be improved. Meanwhile, since the lower limit of the porosity C of the buffer layer is preferably small as possible, it is not necessary to especially define the lower limit, but the lower limit is generally about 0.05% by volume or more.

The average thickness (film thickness) of the buffer layer is for example, preferably about 0.01 to 10 µm, more preferably about 0.03 to 0.5 µm. By this way, the above-mentioned effect can further be improved.

The constitutional material of the buffer layer in the present invention is not especially limited, and for example, one kind or combinations of two or more kinds of zinc, niobium, tin, titanium, vanadium, indium, tungsten, tantalum, zirconium, molybdenum, manganese, iron, copper, nickel, iridium, rhodium, chromium, ruthenium or oxides thereof, and perovskites such as strontium titanate, calcium titanate, barium titanate, magnesium titanate and strontium niobate, or composite oxides or oxide mixtures thereof, various metal compounds such as CdS, CdSe, TiC, $Si_3N_4$, SiC and BN, and like can be used.

Especially in the case when the hole transport layer is a p-type semiconductor, in the case when a metal is used in the buffer layer, it is preferable to use a metal that has a smaller value of work function than that of the hole transport layer and gives Schottky-type contact. Furthermore, in the case when a metal oxide is used in the buffer layer, it is preferable to use a metal oxide that contacts the transparent conductive layer in an ohmic manner, and has a lower energy potential of a conduction band than that of the porous semiconductor layer. At this time, the electron transfer efficiency from the porous semiconductor layer (photoelectric conversion layer) to the buffer layer can be improved by selecting an oxide. Among these, those having equivalent electroconductivity to that of the semiconductor layer (photoelectric conversion layer) are preferable, and those containing titanium oxide as a major component are especially more preferable.

In this case, the titanium oxide layer may be either of an anatase type titanium oxide and a rutile type titanium oxide having a relatively high dielectric constant.

"Photoelectric Conversion Layer"

It is preferable that the photoelectric conversion layer in the present invention is formed of a semiconductor layer containing a semiconductor and a sensitizing pigment, wherein the sensitizing pigment is supported on the semiconductor.

The total content of the pigment per 1 m² of the photoelectric conversion layer is preferably from 0.01 to 100 mmol/m², more preferably from 0.1 to 50 mmol/m², especially preferably from 0.5 to 20 mmol/m².

(Semiconductor)

In the semiconductor in the present invention, single bodies such as silicon and germanium, compounds having elements of Group 3 to Group 5 and Group 13 to Group 15 in the Periodic Table (also referred to as Elemental Periodic Table), metal oxide, metal sulfides, metal serenides or metal nitrides, and the like can be used.

Examples of preferable semiconductors include titanium oxide, tin oxide, zinc oxide, iron oxide, tungsten oxide, zirconium oxide, hafnium oxide, strontium oxide, oxides of indium, cerium, yttrium, lanthanum, vanadium and niobium, or tantalum oxide, cadmium sulfide, zinc sulfide, lead sulfide, silver sulfide, antimony or bismuth sulfide, cadmium or lead serenide, cadmium telluride, and the like. Furthermore, examples of other compound semiconductors include phosphides of zinc, gallium, indium, cadmium and the like, serenide of gallium-arsenic or copper-indium, sulfide of copper-indium, titanium nitride, and the like. More specifically, specific examples of the semiconductor include $TiO_2$, $SnO_2$, $Fe_2O_3$, $WO_3$, $ZnO$, $Nb_2O_5$, $CdS$, $ZnS$, $PbS$, $Bi_2S_3$, $CdSe$, $CdTe$, $GaP$, $InP$, $GaAs$, $CuInS_2$, $CuInSe_2$, $Ti_3N_4$ and the like. Among these, $TiO_2$, $ZnO$, $SnO_2$, $Fe_2O_3$, $WO_3$, $Nb_2O_5$, $CdS$ and $PbS$ are preferably used, $TiO_2$ or $Nb_2O_5$ is more preferably used, and titanium oxide ($TiO_2$) is further more preferably used. The above-mentioned semiconductors may be used singly, or plural semiconductors may be used in combination. For example, several kinds of the above-mentioned metal oxides or metal sulfides can be used in combination, and a titanium oxide semiconductor can be used by mixing with 20 mass % of titanium nitride ($Ti_3N_4$). Furthermore, the zinc oxide/tin oxide composite described in J. Chem. Soc., Chem. Commun., 15 (1999) may be used. At this time, in the case when a component other than metal oxide or metal sulfide is added as a semiconductor, the mass ratio of the additional component to the metal oxide or metal sulfide semiconductor is preferably 30% or less.

In addition, in the case when $TiO_2$ is used in the semiconductor layer, the $TiO_2$ may be either of an anatase type titanium oxide and/or a rutile type titanium oxide that has a relatively high dielectric constant.

Examples of the shape of the semiconductor in the present invention include a filler shape, a particulate shape, a cone shape, a columnar shape, a tubular shape, a flat plate shape and the like, and the shape is not especially limited. Furthermore, as the semiconductor layer in the present invention, a film-shaped semiconductor formed by flocculation of semiconductors having these filler shape, particulate shape, a cone shape, a columnar shape, a tubular shape and the like. Furthermore, in this case, a semiconductor formed by coating the surface with a sensitizing pigment in advance may be used, or a layer formed of a semiconductor may be formed and the layer may be coated with a sensitizing pigment.

In the case when the semiconductor in the present invention has a particulate shape, the particles are preferably primary particles and have an average particle size of preferably from 1 to 5,000 nm, preferably from 2 to 100 nm. Meanwhile, the above-mentioned "average particle size" of the semiconductor is an average particle size of primary particle diameters (primary average particle size (diameter)) when 100 or more samples are observed under an electron microscope.

Furthermore, the semiconductor in the present invention can be subjected to a surface treatment by using an organic base. Examples of the above-mentioned organic base include diary amine, triarylamine, pyridine, 4-t-butylpyridine, polyvinylpyridine, quinoline, piperidine, amidine and the like, and pyridine, 4-t-butylpyridine and polyvinylpyridine are especially preferable. The method for the surface treatment of the semiconductor at this time is not especially limited, and a known method can be used as it is or after suitable modification. For example, in the case when the above-mentioned organic base is a liquid, the liquid is used in its original form, or in the case when the above-mentioned organic base is a solid, a solution dissolved in an organic solvent (an organic base solution) is prepared, and the semiconductor in the present invention is immersed in the above-mentioned liquid organic base or organic base solution at 0 to 80° C. for 1 minutes to 24 hours, whereby the surface treatment of the semiconductor can be conducted.

(Sensitizing Pigment)

The sensitizing pigment in the present invention is carried by the semiconductor by the above-mentioned treatment for sensitizing the semiconductor, and can generate an electromotive force by being excited by light upon irradiation of light, and an arylamine-based pigment is preferable, and a compound represented by the following general formula (1) is more preferable.

[Chem. 1]

General formula (1)

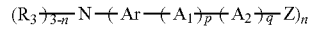

In the above-mentioned general formula (1), $R_3$ each independently represents a hydrogen atom, a halogen atom, a substituted or unsubstituted alkyl group, a substituted or unsubstituted alkoxy group, a substituted or unsubstituted alkenyl group, a substituted or unsubstituted alkynyl group, a substituted or unsubstituted aryl group, an amino group (—$NH_2$), a cyano group (—CN) or a substituted or unsubstituted heterocyclic group. When n is 1, two $R_3$s may be different from each other, and $R_3$ may connect to another substituent to form a cyclic structure. Similarly, the moieties of the formula: —Ar($A_1$)$_p$-($A_2$)$_q$-Z (the right parts connected to the nitrogen atom in the general formula (1)) in the case when n is 2 or 3 may be the same or different from each other. Ar represents a bivalent cyclic compound group. $A_1$ and $A_2$ each independently represents a single bond, a bivalent saturated or unsaturated hydrocarbon group, a substituted or unsubstituted alkylene group, an arylene group, or a bivalent heterocyclic group. Z is an organic group having an acidic group, an alkoxysilane or a halogenated silane, and is preferably an organic group containing at least one carboxyl group. When n is 2 or more, each of the plural $A_1$s, $A_2$s and Zs may be different from each other. p and q are each independently an integer of 0 or more and 6 or less. Here, p and q may be the same or different from each other. In the case when p is 2 or more, the $A_1$s may be the same or different from each other. Similarly, the $A_2$s in the case when q is 2 or more may be the same or different from each other. n is an integer of 1 or more and 3 or less, and is preferably 2.

The Ar in the general formula (1) is not especially limited, and for example, a bivalent to tetravalent cyclic compound group is preferable. Specific examples of the cyclic compound group are those derived from aromatic rings such as a benzene ring, a naphthalene ring, an anthracene ring, a thiophene ring, a phenylthiophene ring, a diphenylthiophene ring, an imidazole ring, an oxazole ring, a thiazole ring, a pyrrole ring, a furan ring, a benzimidazole ring, a benzoxazole ring, a rhodanine ring, a pyrazolone ring, an imidazolone ring, a pyran ring, a pyridine ring and a fluorene ring. A plurality of these aromatic rings may be used in combination, and examples include a biphenyl group, a terphenyl group, a fluorenyl group, a bithiophene group, a 4-thienylphenyl group, a diphenylstyryl group and the like, and groups derived from stilbene, 4-phenylmethylene-2, 5-cyclohexadiene, triphenylethene (for example, 1,1,2-triphenylethene), phenylpyridine (for example, 4-phenylpyridine), styrylthiophene (for example, 2-styrylthiophene), 2-(9H-fluoren-2-yl)thiophene, 2-phenylbenzo[b]thiophene, a phenylbithiophene ring, (1,1-diphenyl-4-phenyl)-1,3-butadiene, 1,4-diphenyl-1,3-dibutadiene, 4-(phenylmethylene)-2,5-cyclohexadiene and a phenyldithienothiophene ring, and the like. These aromatic rings may have substituents, and examples of the substituents include halogen atoms (for example, fluorine, chlorine, bromine and the like), straight chain or branched alkyl groups having a carbon chain length of 1 to 24 (for example, a methyl group, an ethyl group, a t-butyl group, an isobutyl group, a dodecyl group, an octadecyl group, a 3-ethylpentyl group), hydroxyalkyl groups (for example, a hydroxymethyl group, a hydroxyethyl group), alkoxyalkyl groups (for example, a methoxyethyl group and the like), alkoxy groups having a carbon chain length of 1 to 18 (for example, a methoxy group, an ethoxy group, a propoxy group, an isopropoxy group, a butoxy group, a pentyloxy group, a hexyloxy group and the like), aryl groups (for example, a phenyl group, a tolyl group and the like), alkenyl groups (for example, a vinyl group, an allyl group and the like), amino groups (for example, a dimethylamino group, a diethylamino group, a diphenylamino group) and heterocyclic groups (for example, morphonyl group, furanyl groupor the like), each of which is substituted or unsubstituted, and the like. Furthermore, bivalent or trivalent aromatic groups formed by removing two or three hydrogen atoms from the above-mentioned aromatic groups are preferable.

As Ar in the general formula (1) in the present invention, the following chemical formulas (1-A) to (1-G) are encompassed as preferable groups.

[Chem. 2]

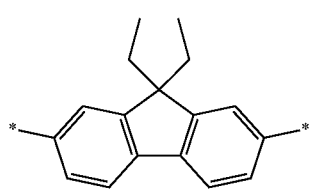

Chemical formula (1-A)

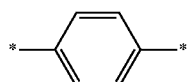

Chemical formula (1-B)

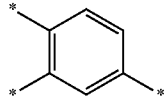

Chemical formula (1-C)

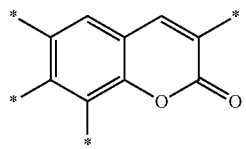

Chemical formula (1-D)

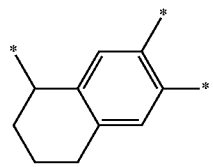

Chemical formula (1-E)

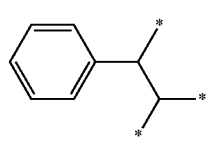

Chemical formula (1-F)

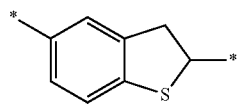

Chemical formula (1-G)

Furthermore, the alkyl group in the general formula (1) is preferably a straight chain or branched alkyl group having a carbon chain length of 1 to 30 or a cycloalkyl group having a carbon chain length of 3 to 10, and more preferably a straight chain or branched alkyl group having a carbon chain length of 1 to 24 or a cycloalkyl group having a carbon chain length of 3 to 9. Among these, the straight chain or branched alkyl group having a carbon chain length of 1 to 30 is not especially limited. Examples include a methyl group, an ethyl group, a n-propyl group, an isopropyl group, a n-butyl group, an isobutyl group, a sec-butyl group, a tert-butyl group, a n-pentyl group, an isopentyl group, a tert-pentyl group, a neopentyl group, a 1,2-dimethylpropyl group, a n-hexyl group, an isohexyl group, a 1,3-dimethylbutyl group, a 1-isopropylpropyl group, a 1,2-dimethylbutyl group, a n-heptyl group, a 1,4-dimethylpentyl group, a 3-ethylpentyl group, a 2-methyl-1-isopropylpropyl group, a 1-ethyl-3-methylbutyl group, a n-octyl group, a 2-ethylhexyl group, a 3-methyl-1-isopropylbutyl group, a 2-methyl-1-isopropyl group, a 1-t-butyl-2-methylpropyl group, a n-nonyl group, a 3,5,5-trimethylhexyl group, a n-decyl group, an isodecyl group, a n-undecyl group, a 1-methyldecyl group, a n-dodecyl group, a n-tridecyl group, a n-tetradecyl group, a n-pentadecyl group, a n-hexadecyl group, a n-heptadecyl group, a n-octadecyl group, a n-nonadecyl group, a n-eicosyl group, a n-heneicosyl group, a n-docosylgroup, a n-tricosyl group, a n-tetracosyl group and the like. Among these, straight chain or branched alkyl groups having a carbon chain length of 6 to 24 are preferable, and straight chain alkyl groups having a carbon chain length of 6 to 18 are preferable.

Furthermore, the above-mentioned cycloalkyl group having a carbon chain length of 3 to 10 is also not especially limited. Examples include a cyclopropyl group, a cyclobutyl group, a cyclopentyl group, a cyclohexyl group, a cycloheptyl group, a cyclooctyl group, a cyclononyl group, a cyclodecyl group and the like. Among these, cycloalkyl groups having a carbon chain length of 3 to 6 are preferable.

Among these, straight chain or branched alkyl groups having a carbon chain length of 1 to 18, and cycloalkyl groups having a carbon chain length of 3 to 7 are preferable, and straight chain alkyl groups having a carbon chain length of 1 to 6 such as a methyl group, an ethyl group, a n-propyl group, a n-butyl group, a n-pentyl group and a n-hexyl group, and branched alkyl groups having a carbon chain length of 3 to 6 such as an isopropyl group and a t-butyl group, and cycloalkyl groups having a carbon chain length of 5 to 6 such as a cyclopentyl group and a cyclohexyl group are more preferable.

The alkoxy group in the general formula (1) is not especially limited, and is preferably an alkoxy group having a carbon chain length of 1 to 30, preferably an alkoxy group having a carbon chain length of 1 to 18. Examples include a methoxy group, an ethoxy group, a propoxy group, an isopropoxy group, a butoxy group, an isobutoxy group, a sec-butoxy group, a tert-butoxy group, a pentyloxy group, an isopentyloxy group, a hexyloxy group, a 2-ethylhexyloxy group, an octyloxy group, a nonyloxy group, a decyloxy group, an undecyloxy group, a dodecyloxy group, a tridecyloxy group, a tetradecyloxy group, a pentadecyloxy group, a hexadecyloxy group, a heptadecyloxy group, an octadecyloxy group, a n-heneicosyloxy group, a n-docosyloxy group, a n-tricosyloxy group, a n-tetracosyloxy group and the like. Among these, alkoxy groups having a carbon chain length of 6 to 18 are preferable, and a hexyloxy group and a decyloxy group are more preferable.

The alkenyl group in the general formula (1) is not especially limited, and the alkenyl group may be either straight, branched or cyclic. Furthermore, the carbon number that the alkenyl group has is preferably 2 to 18. Specific examples of the alkenyl group include a vinyl group, an allyl group, a propenyl group, an isopropenyl group, a 1-butenyl group, a 2-butenyl group, a 3-butenyl group, a 1-hexenyl group, a 2-hexenyl group, a 3-hexenyl group, 4-hexenyl group, 5-hexenyl group, a cyclopentenyl group, a cyclohexenyl group, a cyclooctenyl group and the like. Other alkenyl groups may also be used.

The alkynyl group in the general formula (1) is not especially limited, and may be either straight, branched or cyclic. Furthermore, the carbon number that the alkynyl group has is preferably 2 to 18. Specific examples of the alkynyl group include an ethynyl group, a 2-propynyl group, a 2-butynyl group and the like. Other alkynyl groups may also be used.

The aryl group in the general formula (1) is not especially limited, and examples include a phenyl group, a naphthyl group, biphenyl group, a fluorenyl group, an anthryl group, a pyrenyl group, an azulenyl group, an acenaphthylenyl group, a terphenyl group, a phenanthryl group and the like. Among these, a phenyl group, a biphenyl group and a naphthyl group are preferable.

The heterocyclic group in the general formula (1) is not especially limited, and is preferably a heterocyclic group containing at least one kind selected from a nitrogen atom, an oxygen atom and a sulfur atom, and the heterocyclic group is not limited to a monocyclic heterocyclic group, and may also be a condensed heterocyclic group in which plural heterocyclic rings are condensed (for example, a group derived from dithieno[3,2-b:2',3'-d]thiophene in which three thiophene rings are condensed, or a condensed heterocyclic group in which a heterocyclic ring and a hydrocarbon ring (a non-aromatic hydrocarbon ring or an aromatic hydrocarbon ring) are condensed (ortho-condensation, ortho and peri-condensation and the like). Furthermore, the heterocyclic group may be either non-aromatic or aromatic. In addition, in the condensed heterocyclic group in which a heterocyclic ring and a hydrocarbon ring are condensed, either of the heterocyclic ring or hydrocarbon ring may have a bond. Specific examples of the heterocyclic group in the general formula (1) include a pyrrolyl group, an imidazolyl group, a pyridyl group, a pyrazinyl group, an indolyl group, a quinolyl group, an isoquinolyl group, a quinazolyl group, a carbazolyl group, a carbolinyl group, a phenanthrydinyl group, an acridinyl group, a phenazinyl group, isobenzofuranyl, a chromenyl group, a thienyl group, a thianthrenyl group, a morpholinyl group, an isothiazolyl group, an isoxazolyl group, a phenoxathiinyl group and the like. Preferable heterocyclic groups are a pyrrolyl group, an indolyl group and a carbazolyl group.

Furthermore, the "substituted or unsubstituted" in the general formula (1) of the present invention refers to that at least one or more hydrogen atom(s) in the alkyl group, alkoxy group, alkenyl group, alkynyl group, aryl group and heterocyclic group exemplified above is/are substituted with other substituent(s), and the substituent(s) may be substituted with the substituent(s) to the extent that the above-mentioned alkyl group, alkoxy group, alkenyl group, alkynyl group, aryl group and heterocyclic group does not exceed the number of the carbon number. The same will apply to the following. The substituent that is optionally present is not the same as the substituent to be substituted. For example, in the case when $R_3$ is an alkyl group, the alkyl group is not further substituted with an alkyl group.

Preferable groups for $R_3$ in the general formula (1) in the present invention include the following chemical formulas (2-A) to (2-S).

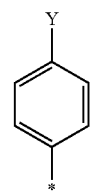

Chemical formula (2-A)

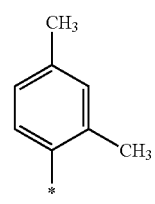

Chemical formula (2-B)

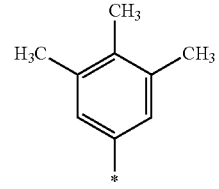

Chemical formula (2-C)

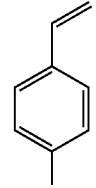

Chemical formula (2-D)

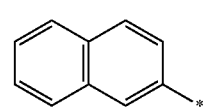

Chemical formula (2-E)

-continued

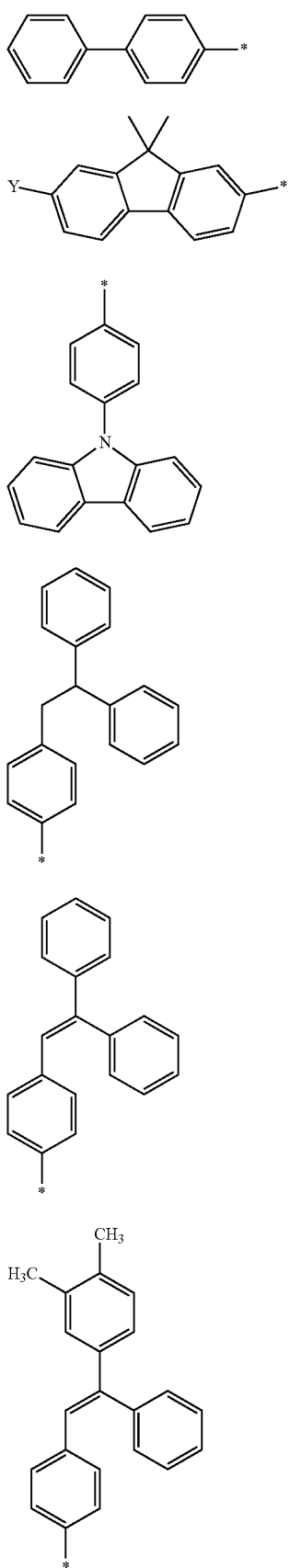

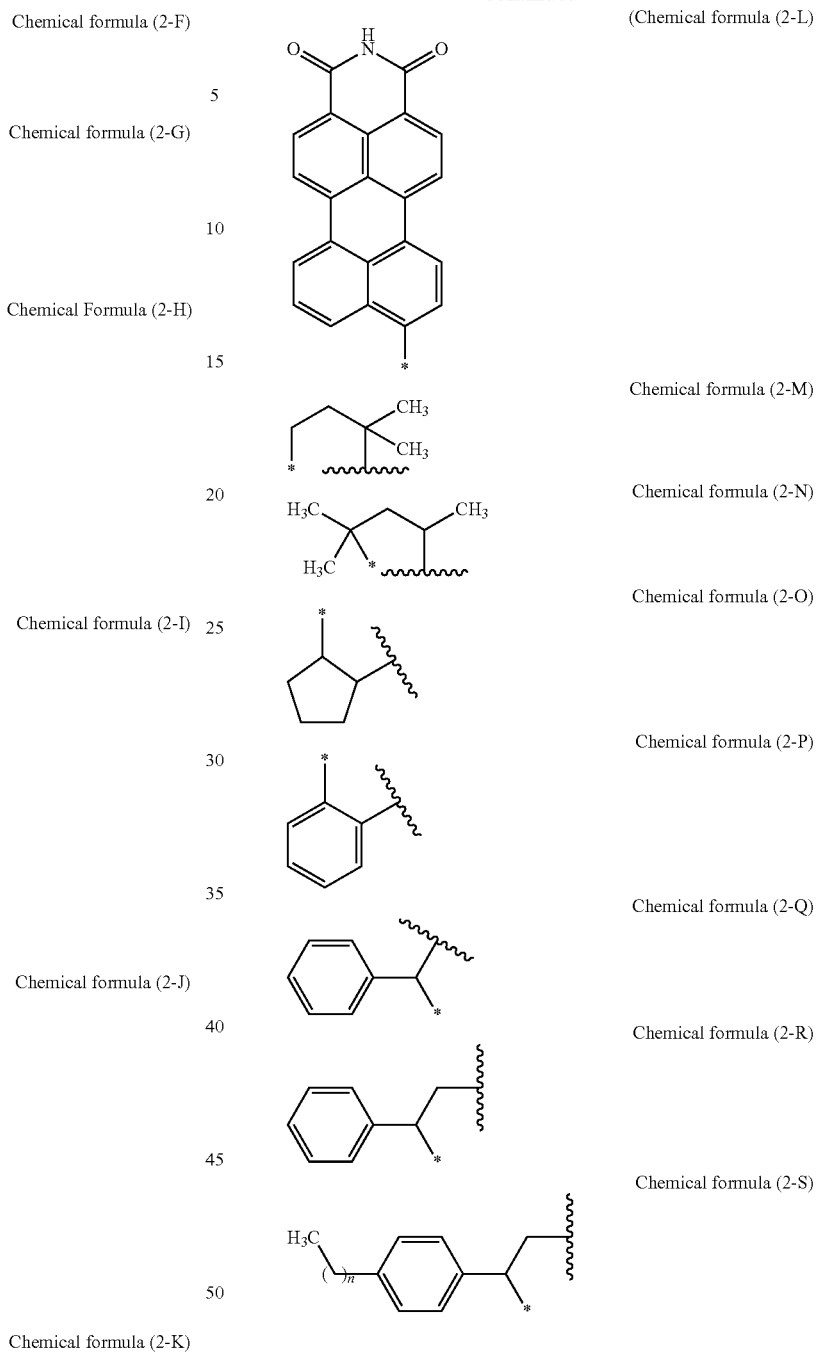

Furthermore, in the above-mentioned chemical formula (2-S), h is a polymerization degree and is an integer of 1 or more and 17 or less.

In the above-mentioned chemical formulas (2-A) and (2-G), Y represents a hydrogen atom, the above-mentioned alkyl group, an alkoxy group, an alkenyl group, an alkynyl group, an aryl group or a heterocyclic group, and is preferably a hydrogen atom, an alkyl group or an alkoxy group. Furthermore, in the above-mentioned chemical formulas (2-M) to (2-S), the wave line part represents the position that connects to other group. For example, $R_3$ forms condensed cyclic structure together with Ar by the connection of the wave line part.

The alkylene group in the general formula (1) is not especially limited and has a linear or branched chain form, and examples can include a methylene group, an ethylene group, a propylene group, a butylene group, an isobutylene group, sec-butylene group, a tert-butylene group, a pentylene group, an iso-pentylene group, a hexylene group and the like.

The arylene group in the general formula (1) is not especially limited, and examples include a phenylene group, a biphenyl-diyl group, a terphenyl-diyl group, a naphthalene-diyl group, an anthracene-diyl group, a tetracene-diyl group, a fluorene-diyl group, a phenanthrene-diyl group and the like.

Preferable groups as $A_1$ and $A_2$ in the general formula (2) in the present invention include the chemical formulas (3-A) to (3-Z) and the chemical formulas (3-a) to (3-b) below.

[Chem. 4]

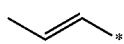
Chemical formula (3-A)

Chemical formula (3-B)

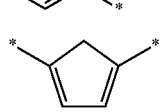
Chemical formula (3-C)

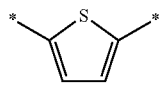
Chemical formula (3-D)

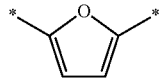
Chemical formula (3-E)

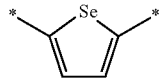
Chemical formula (3-F)

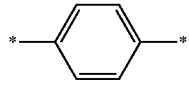
Chemical formula (3-G)

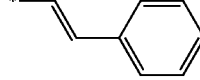
Chemical formula (3-H)

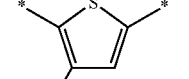
Chemical formula (3-I)

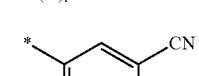
Chemical formula (3-J)

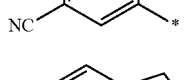
Chemical formula (3-K)

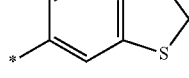
Chemical formula (3-L)

-continued

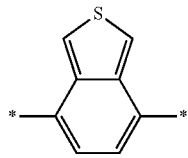
Chemical formula (3-M)

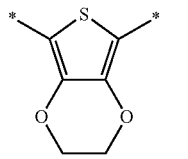
Chemical formula (3-N)

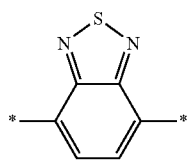
Chemical formula (3-O)

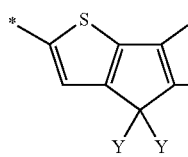
Chemical formula (3-P)

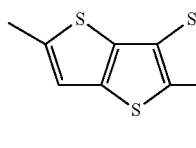
Chemiucal formula (3-Q)

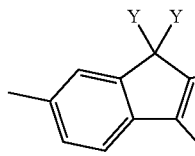
Chemical formula (3-R)

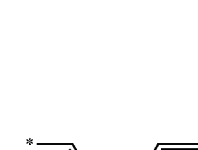
Chemical formula (3-S)

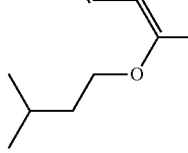

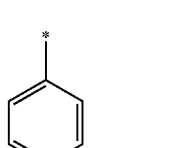
Chemical formula (3-T)

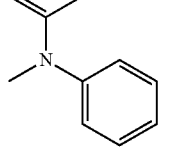

Chemical formula (3-U)
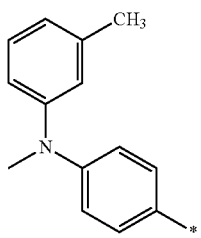

Chemical formula (3-V)
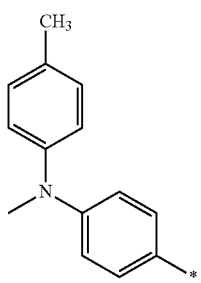

Chemical formula (3-W)
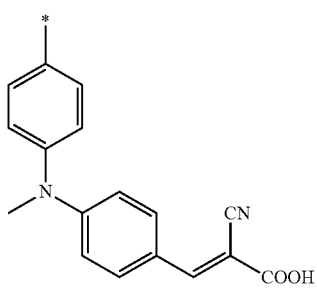

[Chem. 5]

Chemiocal formula (3-X)
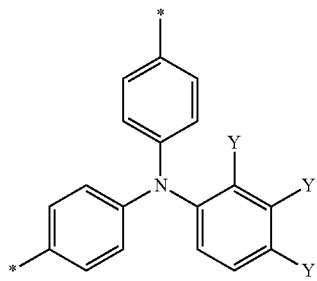

Chemical formula (3-Y)

Chemical formula (3-Z)
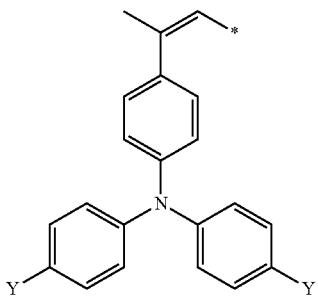

Chemical formula (3-a)
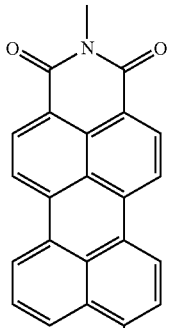

Chemical formula (3-b)
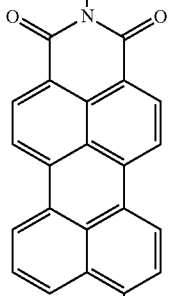

Furthermore, in the above-mentioned chemical formula (3-I), i is a polymerization degree, and is an integer of 1 or more and 17 or less. Furthermore, in the above-mentioned chemical formulas (3-P), (3-R), (3-X), and (3-Z), Y represents a hydrogen atom, the above-mentioned alkyl group, an alkoxy group, an alkenyl group, an alkynyl group, an aryl group or a heterocyclic group, and is preferably a hydrogen atom, an alkyl group or an alkoxy group.

Furthermore, in the general formula (1), Z is an organic group having an acidic group, an alkoxysilane or a halogenated silane, preferably an organic group having a partial structure of either of Ar having an acidic group and an electron withdrawing group or an electron withdrawing cyclic structure, more preferably an organic group containing at least one carboxyl group. This partial structure Z is substituted with at least one hydrogen atom (H) existing in either of Ar, $Ar_1$ and $Ar_2$, and $R_3$ in the general formula (1), and is preferably substituted by at least the hydrogen atom (H) at the terminal of $Ar_2$. In this case, examples of the acidic group in the partial structure Z include a carboxyl group, a sulfo group [—$SO_3H$], a sulfino group, a sulfinyl group, a phosphonate group [—$PO(OH)_2$], a phosphoryl group, a phosphinyl group, a phosphono group, a thiol group, a hydroxy group, a phosphonyl group, an alkoxysilane group, and a sulfonyl group; and salts thereof, and the like. Among these, as the acidic group, a carboxyl group, a sulfo group, a phosphate group and a hydroxy group are preferable, and a carboxyl group is more preferable. Furthermore, examples of the electron withdrawing group include a cyano group, a nitro group, a fluoro group, a chloro group, a bromo group, an iodo group, a perfluoroalkyl group (for example, a trifluoromethyl group), an alkylsulfonyl group, an arylsulfonyl group, a perfluoroalkylsulfonyl group, a perfluoroarylsulfonyl group and the like. Among these, a cyano group, a nitro group, a fluoro group and a chloro group are preferable, and a cyano group and a nitro group are more preferable. Examples of the electron withdrawing cyclic structure include a rhodanine ring, a dirhodanine ring, an imidazolone ring, a pyrazolone ring, a pyrazoline ring, a quinone ring, a pyran ring, a pyrazine ring, a pyrimidine ring, an imidazole ring, an indole ring, a benzothiazole ring, a benzoimidazole ring, a benzoxazole ring, a thiadiazole ring and the like. Among these, a rhodanine ring, a dirhodanine ring, an imidazolone ring, a pyrazoline ring, a quinone ring and a thiadiazole ring are preferable, and a rhodanine ring, a dirhodanine ring, an imidazolone ring and a pyrazoline ring are more preferable. These Zs can effectively inject photoelectrons to a semiconductor (especially an oxide semiconductor). Furthermore, in the partial structure Z, the acidic group and the electron withdrawing group or electron withdrawing cyclic structure may bond via an atom such as an oxygen atom (O), a sulfur atom (S), a serenium atom (Se) or a tellurium atom (Te). Alternatively, the partial structure Z may be charged, especially positively charged, and may have a counterion such as $Cl^-$, $Br^-$, $I^-$, $ClO_4^-$, $NO_3^-$, $SO_4^{2-}$ or $H_2PO_4^-$ at this time.

Specifically, preferable examples of Z in the above-mentioned general formula (2) include the following chemical formulas (4-A) to (4-N).

[Chem. 6]

Chemical formula (4-A)

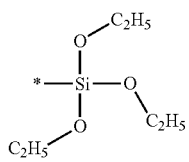

Chemical formula (4-B)

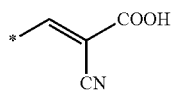

Chemical formula (4-C)

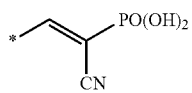

Chemical formula (4-D)

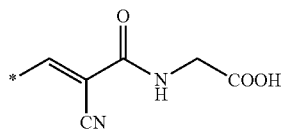

Chemical formula (4-E)

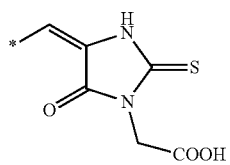

Chemical formula (4-F)

-continued

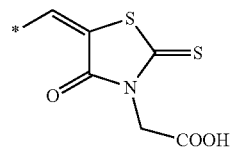

Chemical formula (4-G)

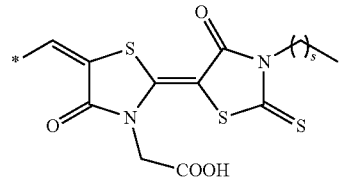

Chemical formula (4-H)

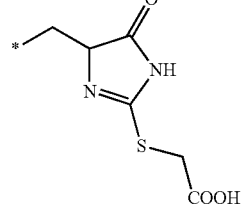

Chemical formula (4-I)

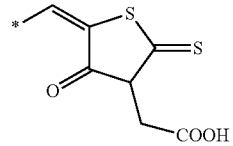

Chemical formula (4-J)

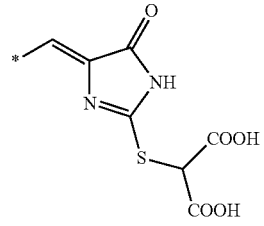

Chemical formula (4-K)

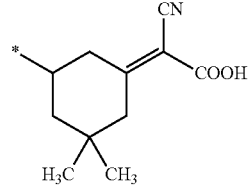

Chemical formula (4-L)

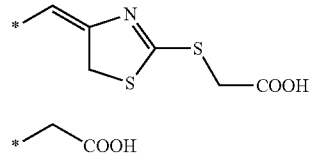

Chemical formula (4-M)

Chemical formula (4-N)

In the above-mentioned chemical formula (4-H), g represents a polymerization degree, and is an integer of 1 or more and 17 or less.

In the present invention, since the pigment is not deteriorated by the detachment of $CO_2$ (Kolbe electrolysis) by an applied voltage even a carboxyl group is present, a sensitizing pigment having a carboxyl group can be preferably used.

Furthermore, especially preferable examples of the sensitizing pigment in the present invention are shown below.

[Chem. 7]
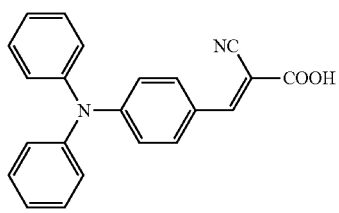 A-1
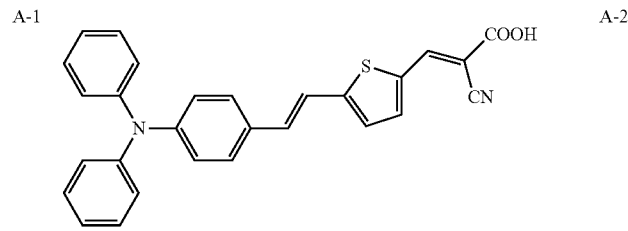 A-2
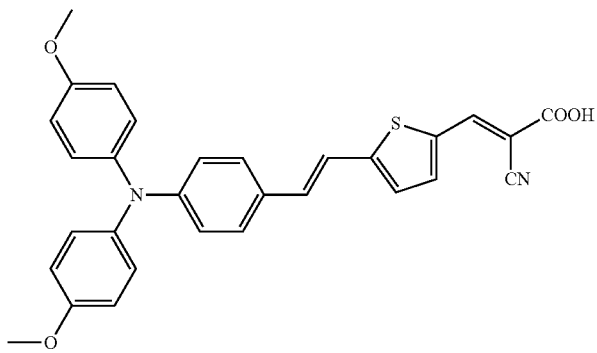 A-3
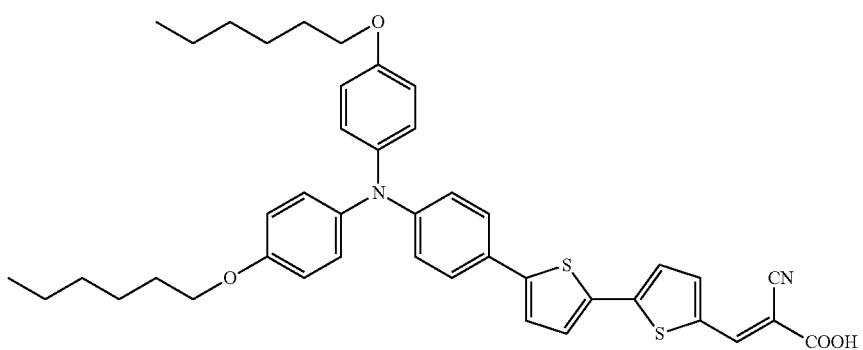 A-4
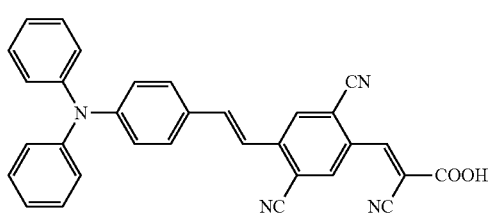 A-5
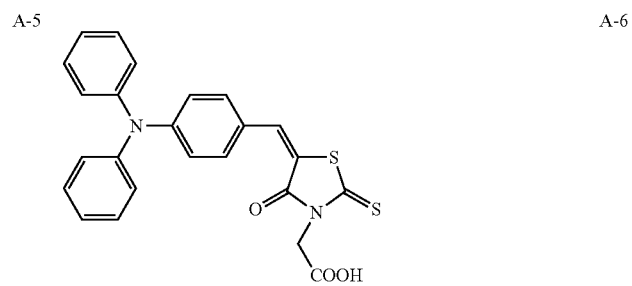 A-6
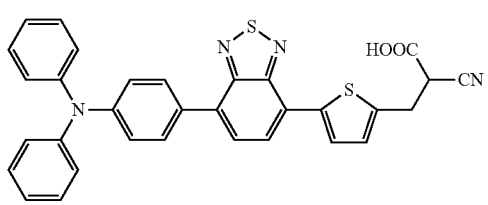 A-7
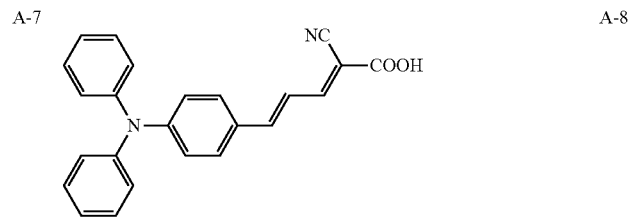 A-8

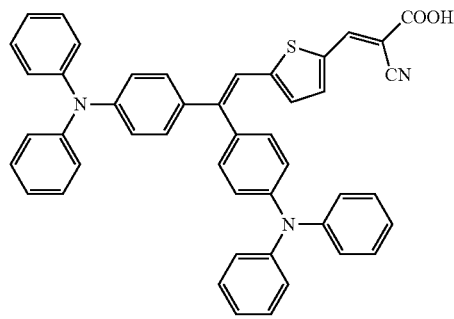 A-9
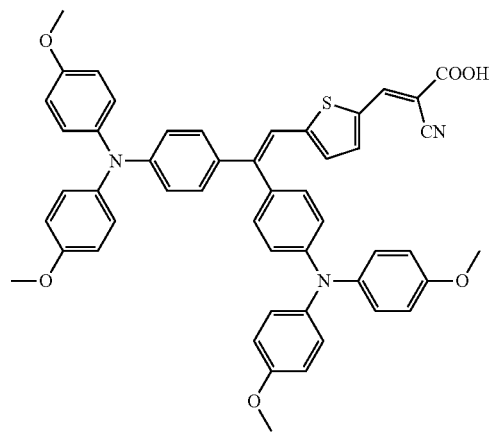 A-10
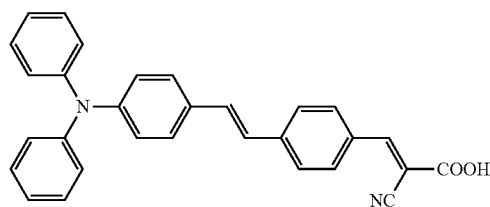 A-11
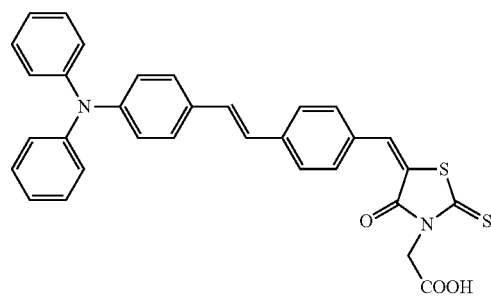 A-12
[Chem. 8]
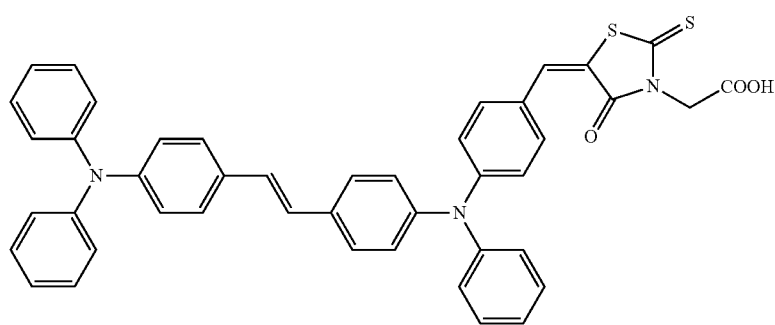 A-13
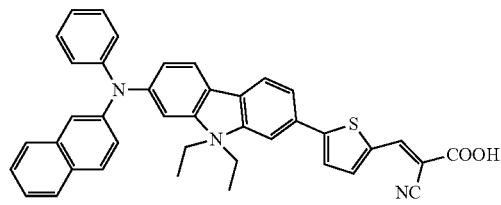 A-14
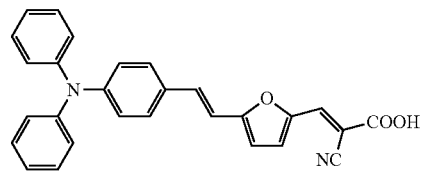 A-15
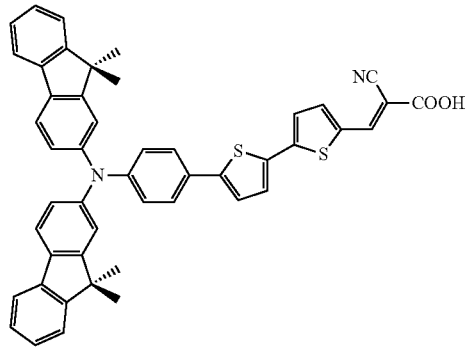 A-16
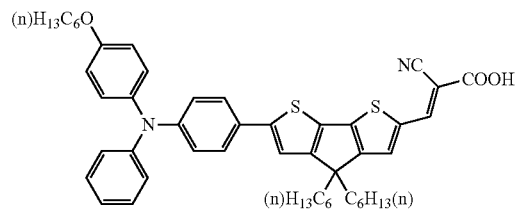 A-17

-continued
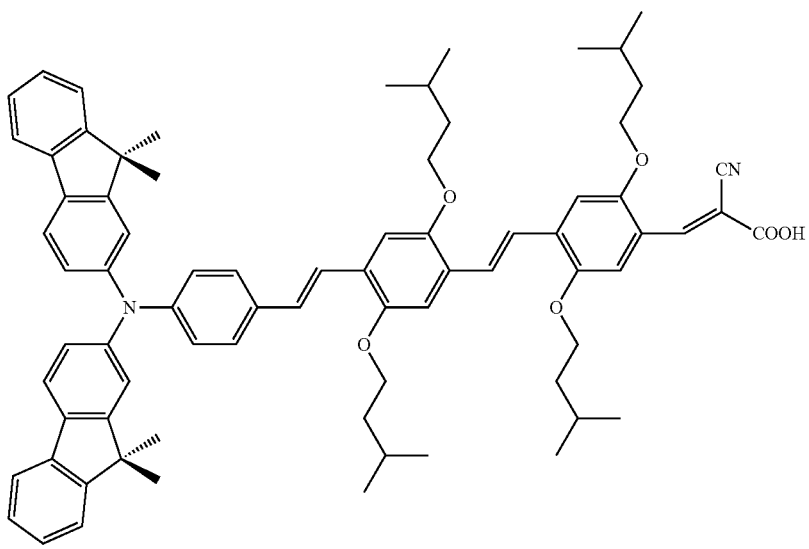
A-18
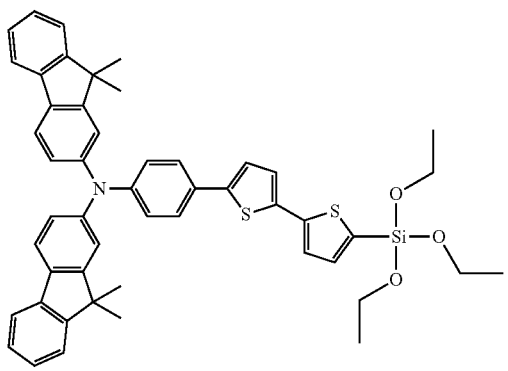
A-19
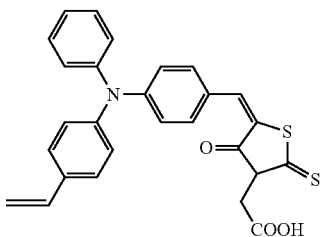
A-20
[Chem. 9]
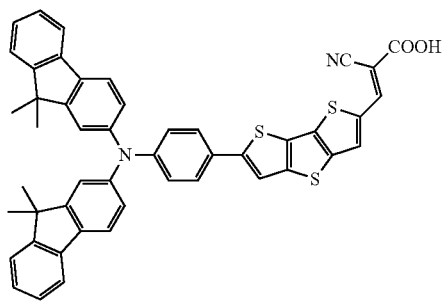
A-21
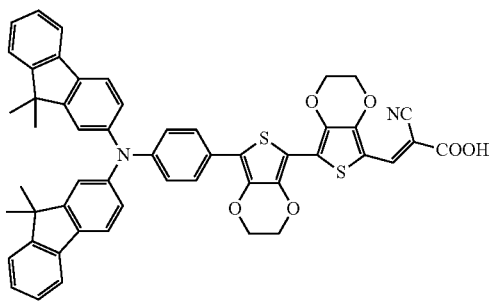
A-22
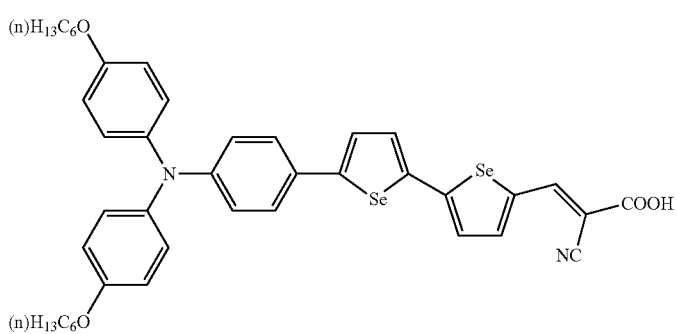
A-23

A-24
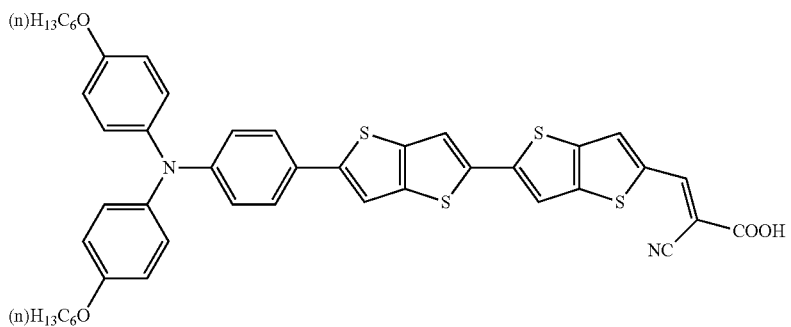
A-25
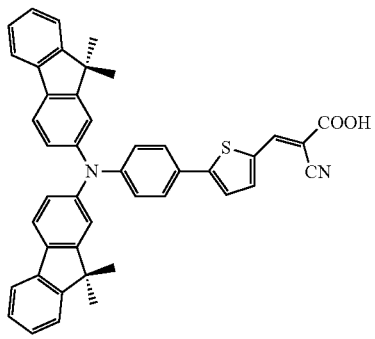
A-26
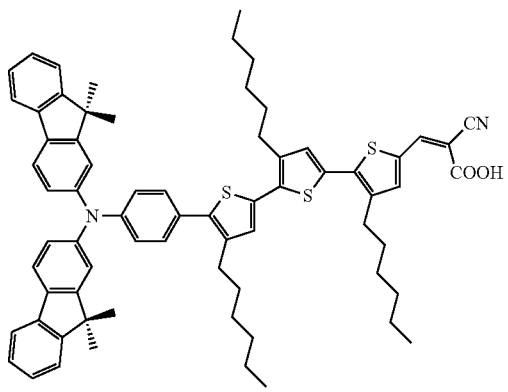
A-27
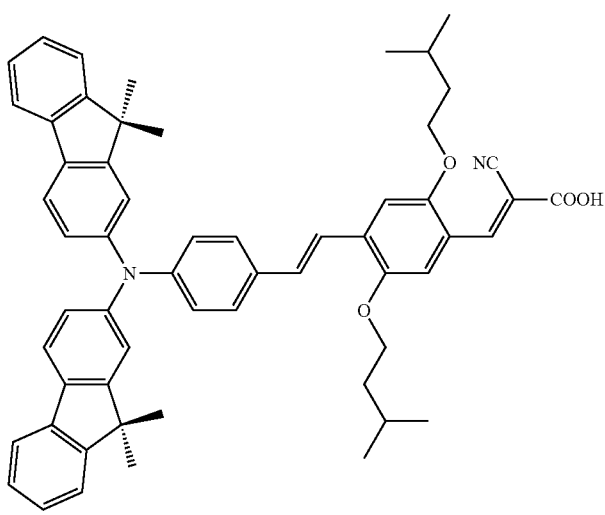

A-28
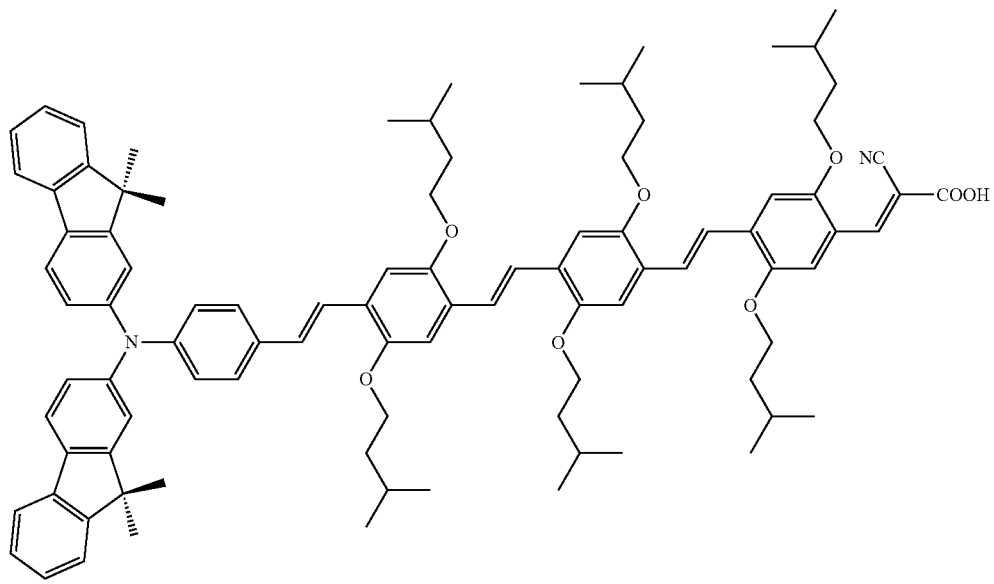
[Chem. 10]
A-29
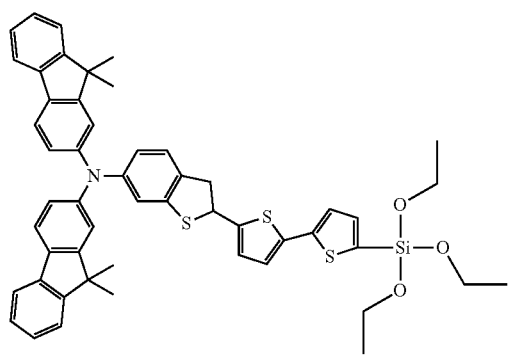
A-30
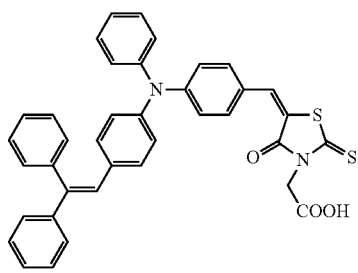
A-31
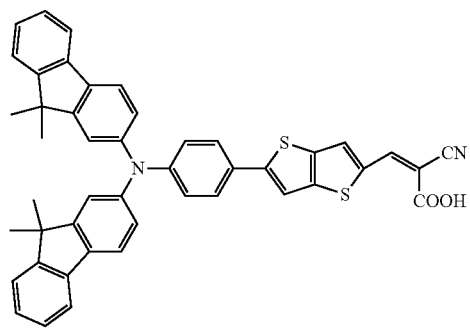
A-32
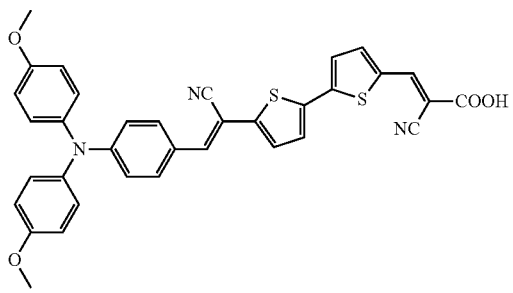
A-33
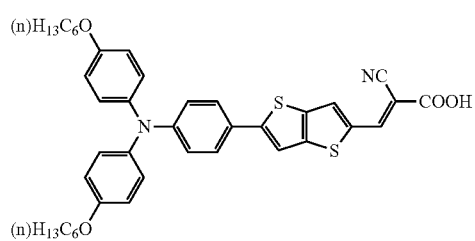
A-34
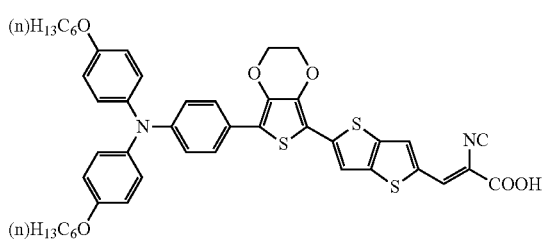

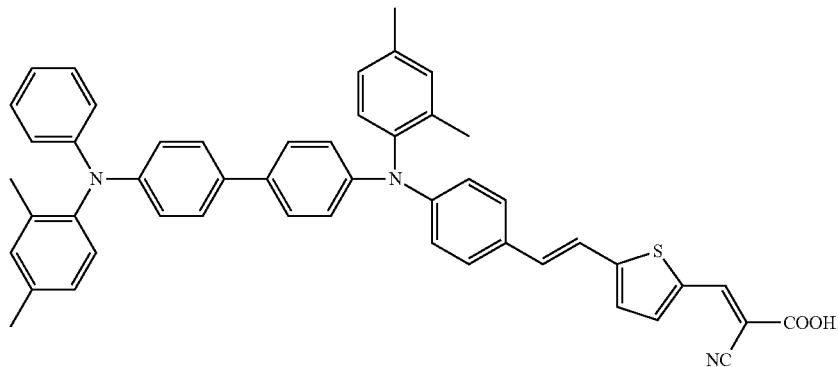
A-35
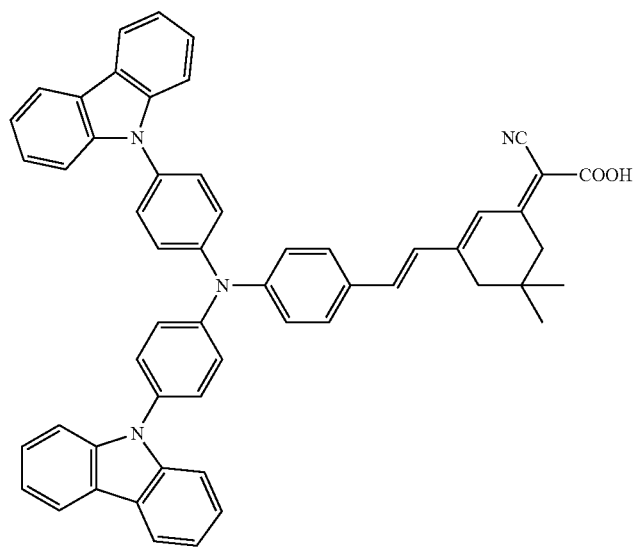
A-36
[Chem. 11]
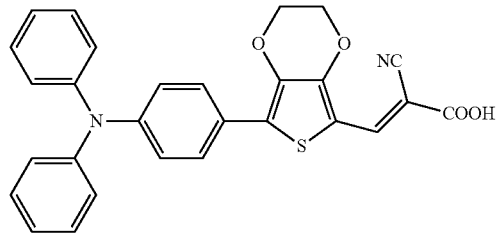
A-37
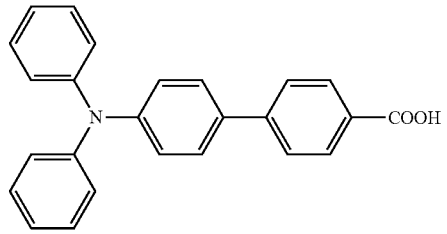
A-38
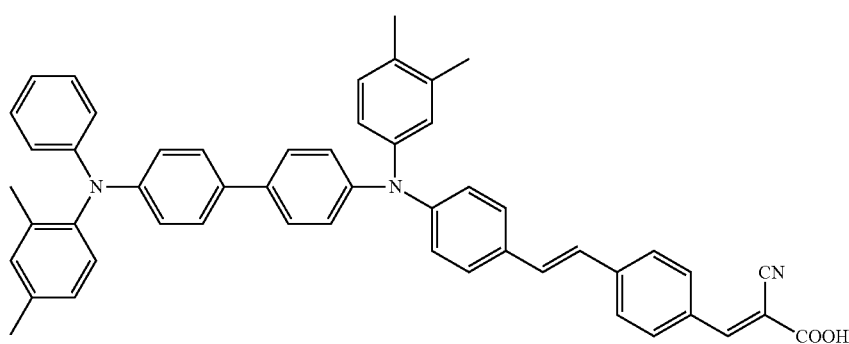
A-39

A-40
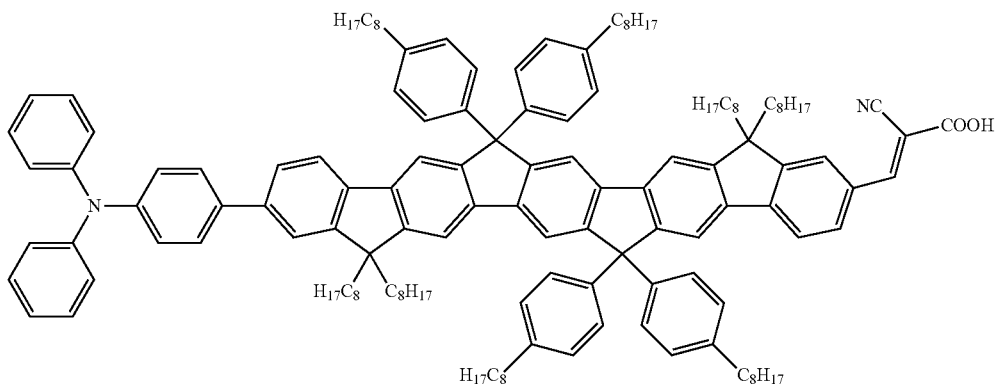
A-41
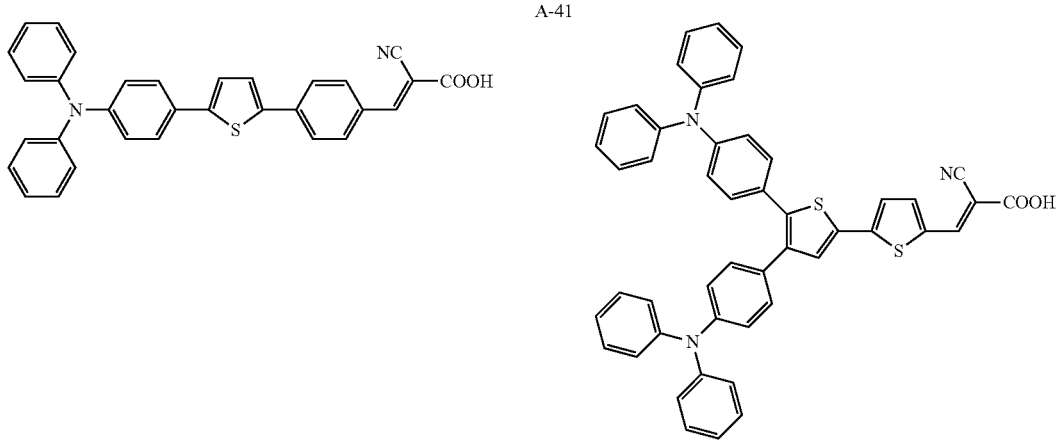
A-42
A-43
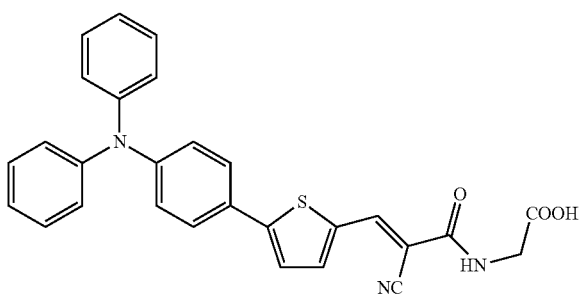
A-44
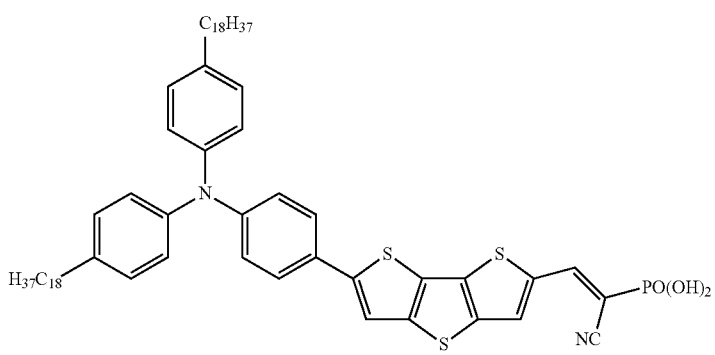

[Chem. 12]
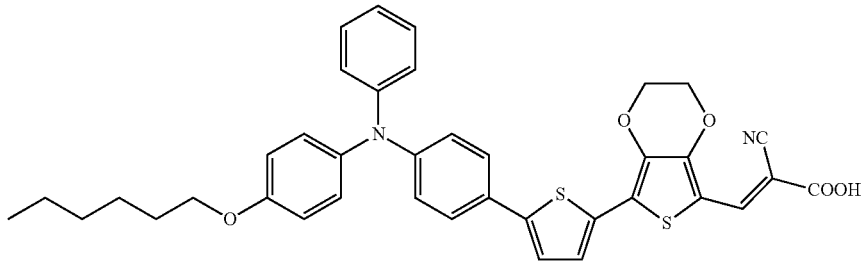
A-45
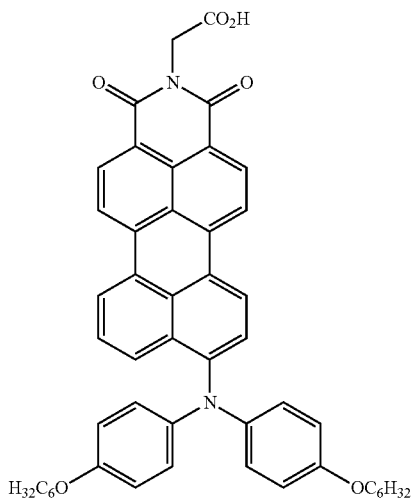
A-46
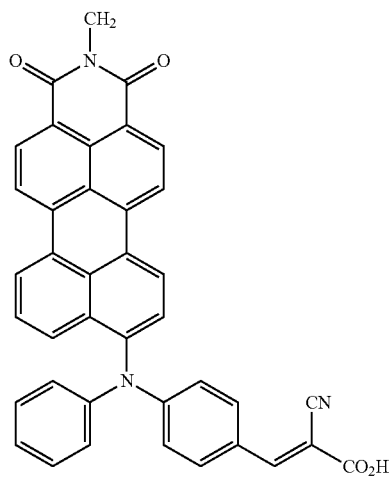
A-47
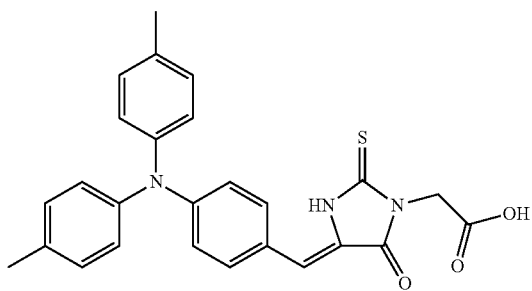
A-48

A-49
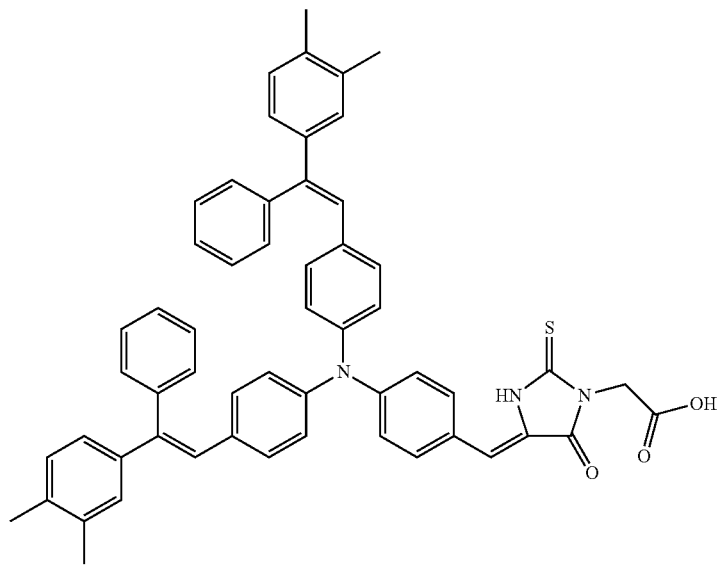
A-50
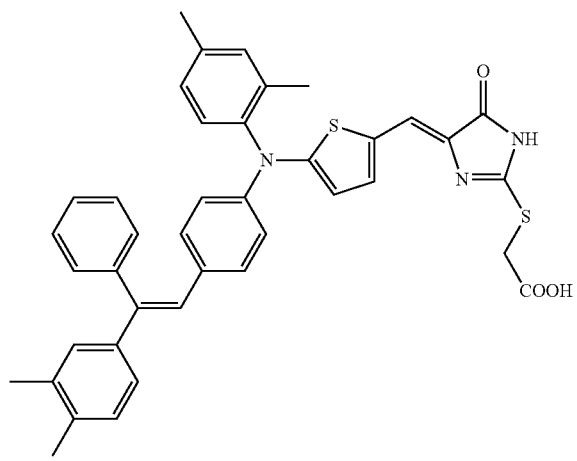
A-51
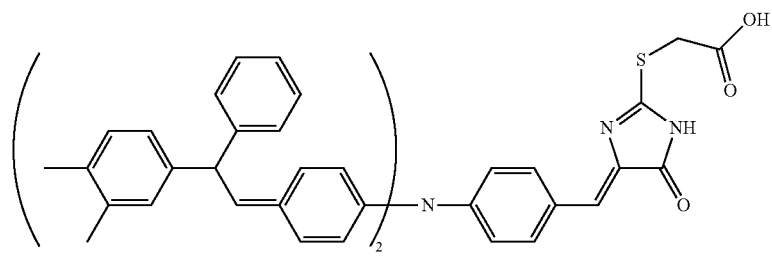

-continued
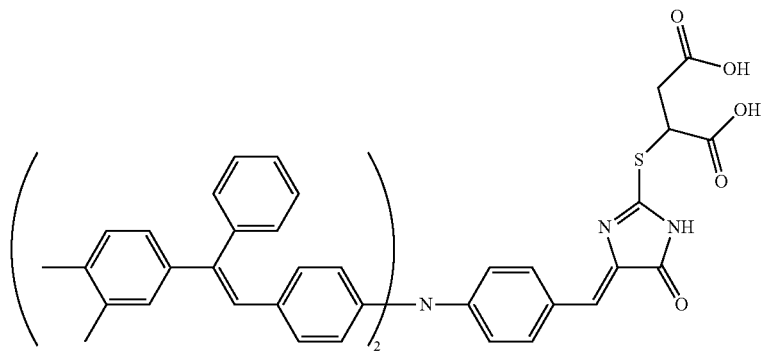
A-53
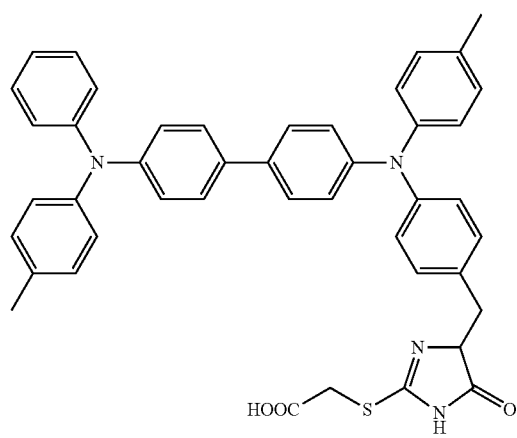
A-54
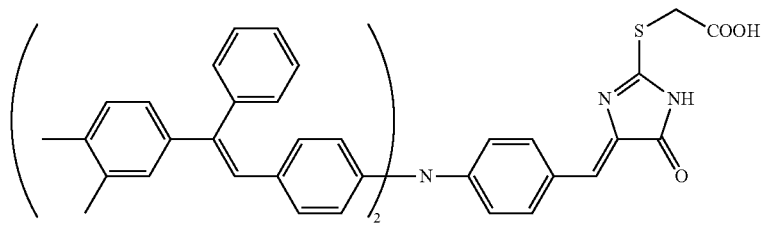
A-55
[Chem. 14]
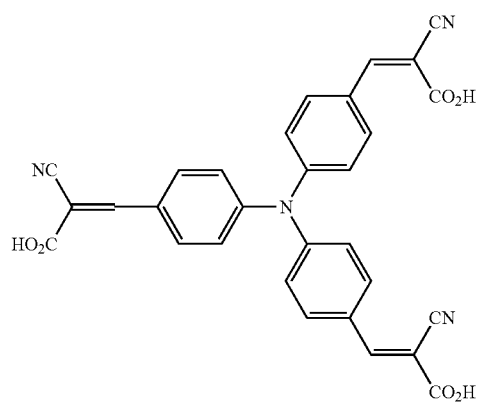
B-1

-continued
B-2
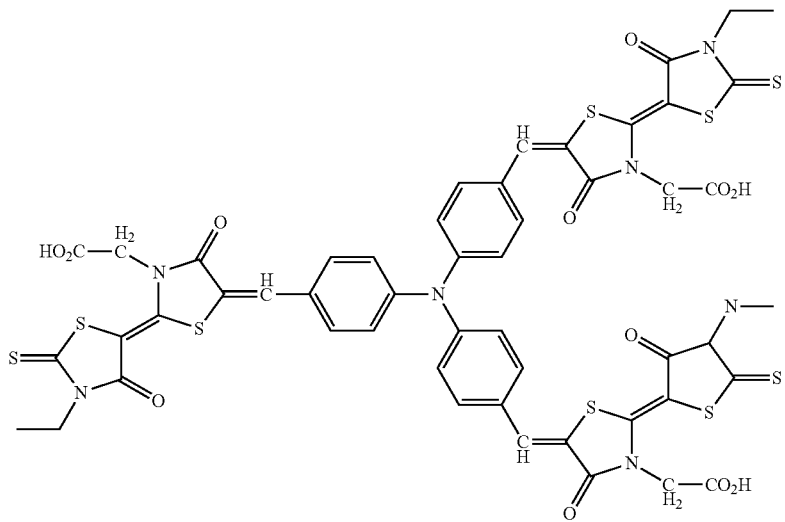
B-3
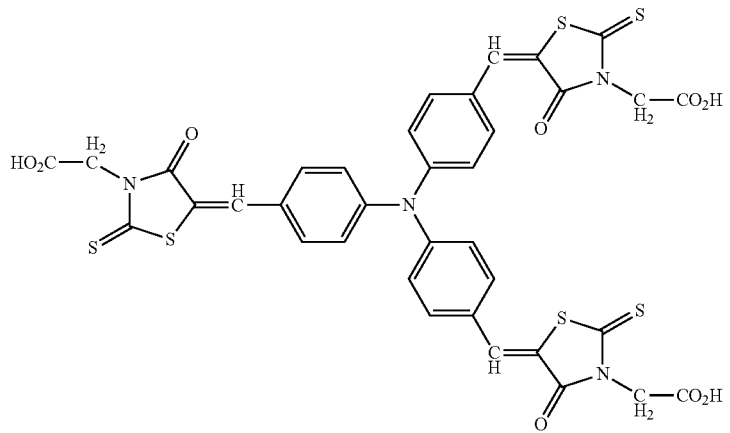
B-4
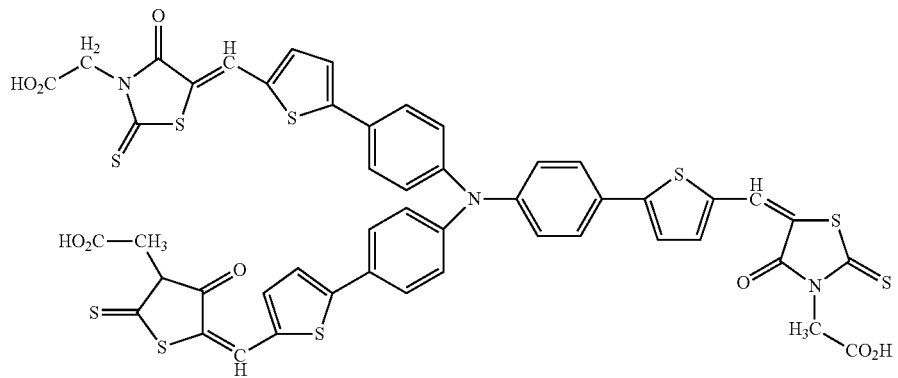

-continued
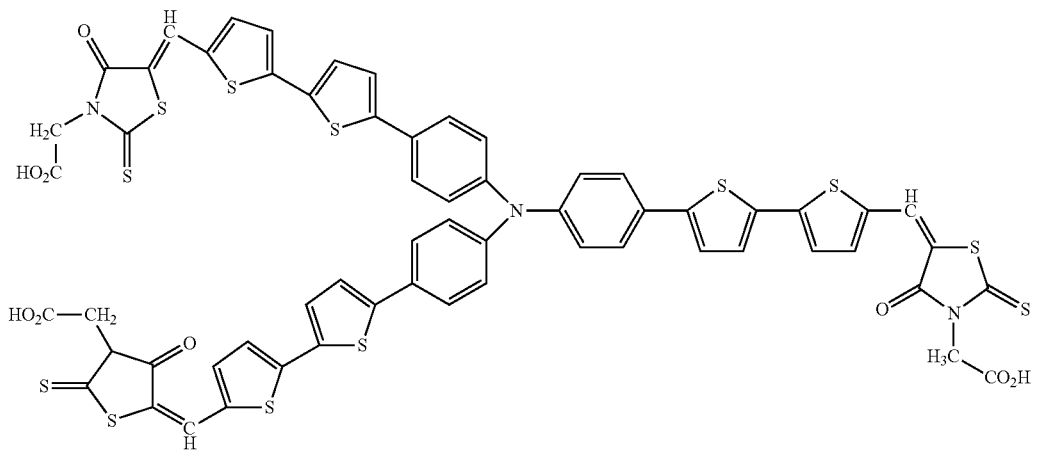
B-5
[Chem. 15]
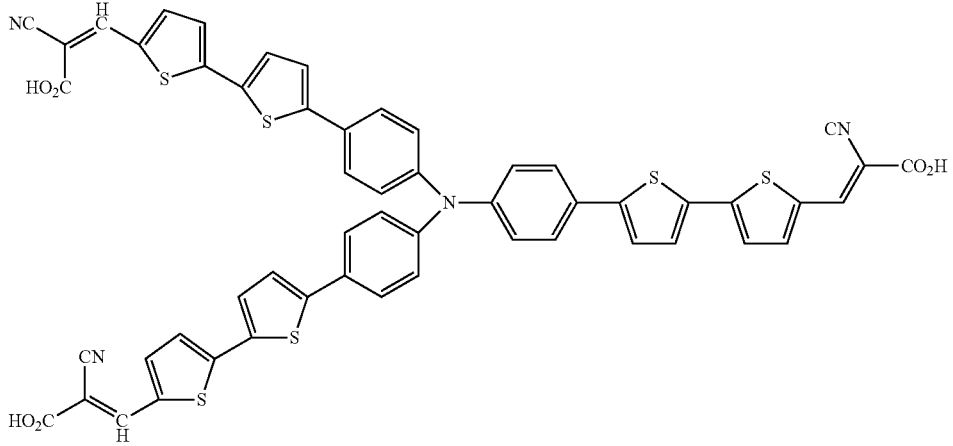
B-6
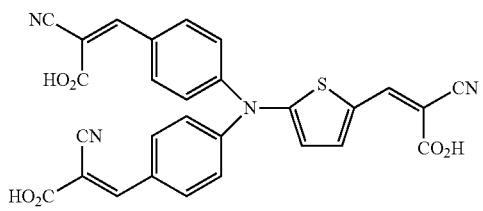
B-7
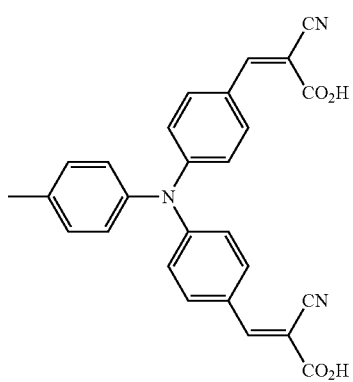
B-8

-continued
B-9
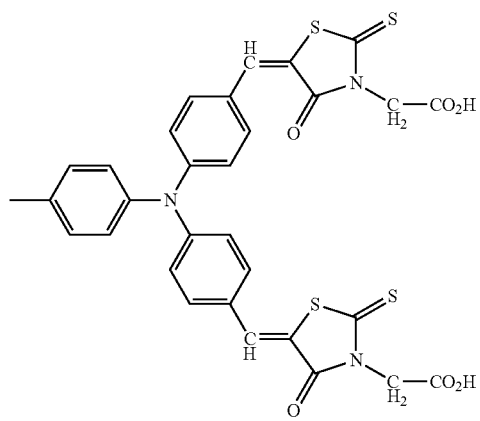
B-10
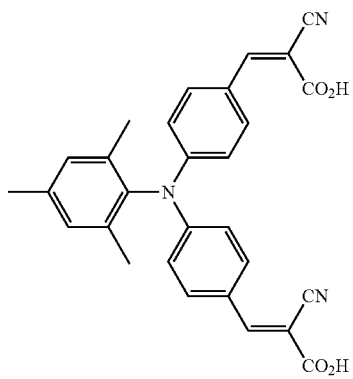
B-11
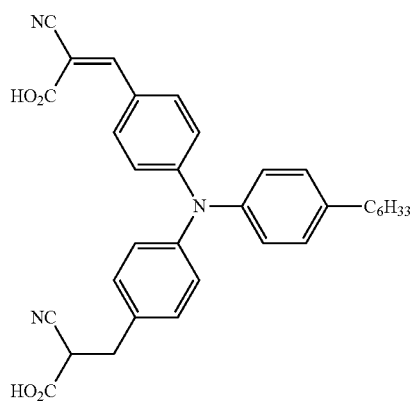
B-12
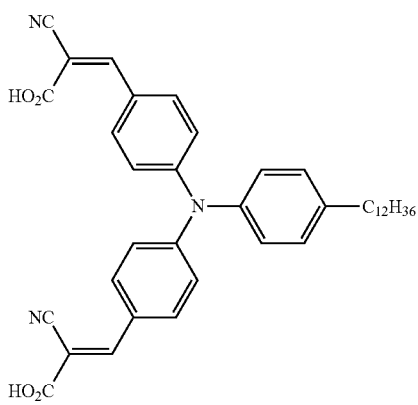
B-13
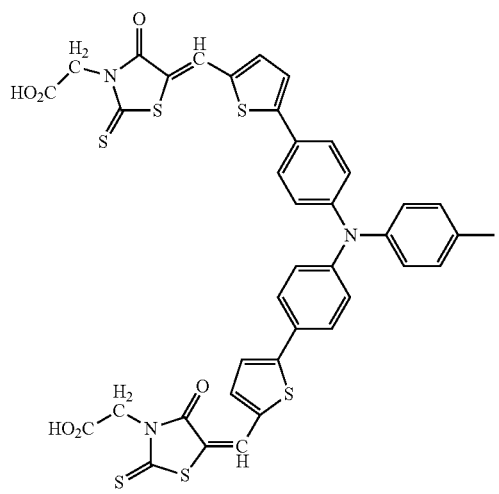
B-14
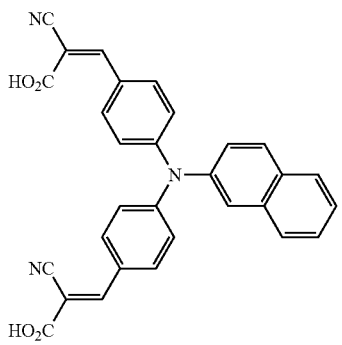

[Chem. 16]
B-15
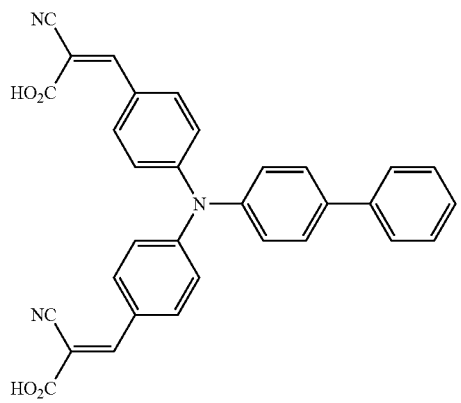
B-16
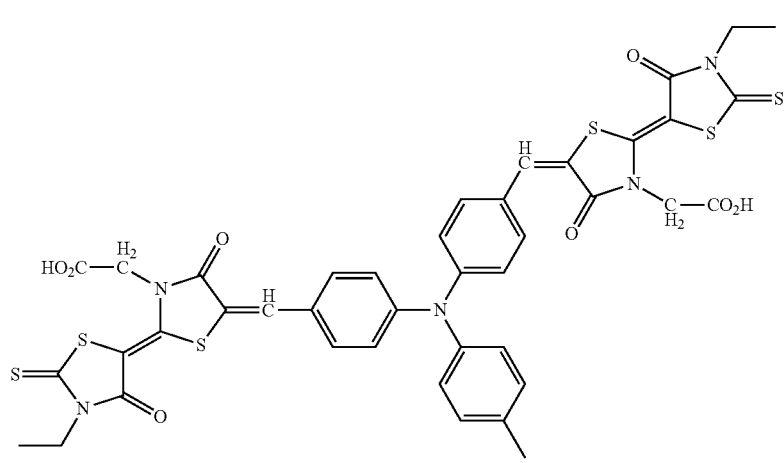
B-17
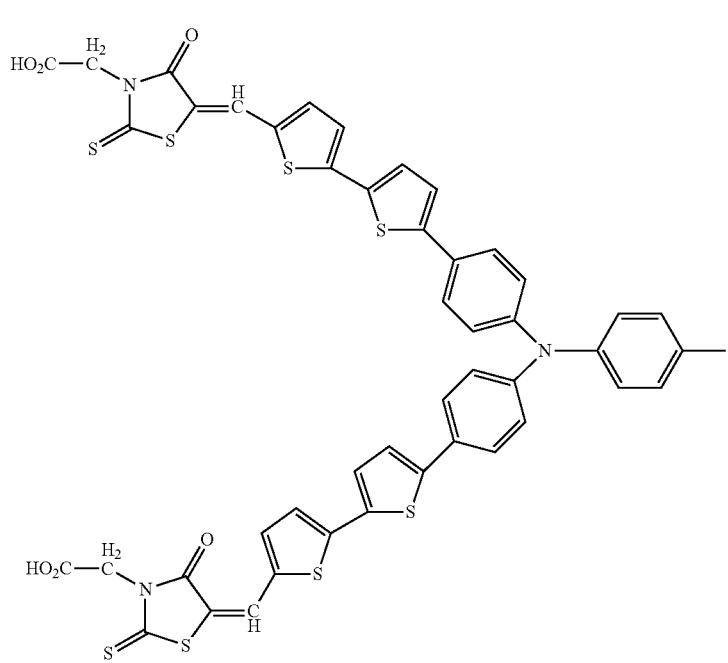

-continued
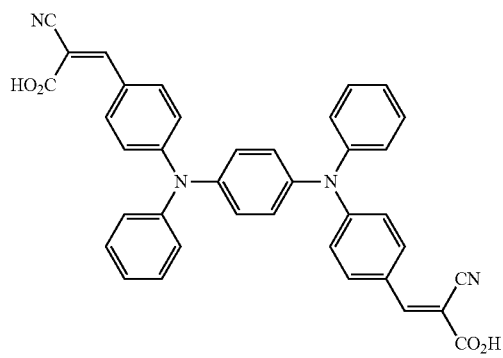
B-18
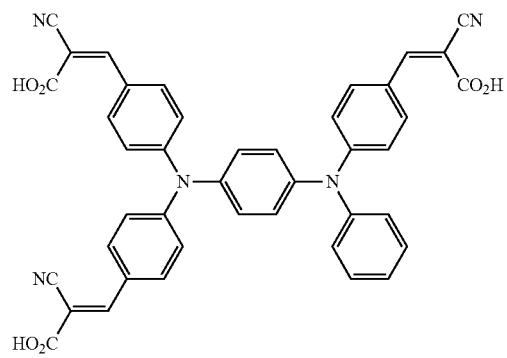
B-19
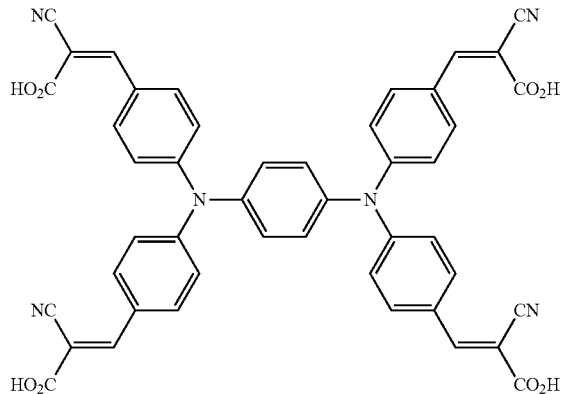
B-20
[Chem. 17]
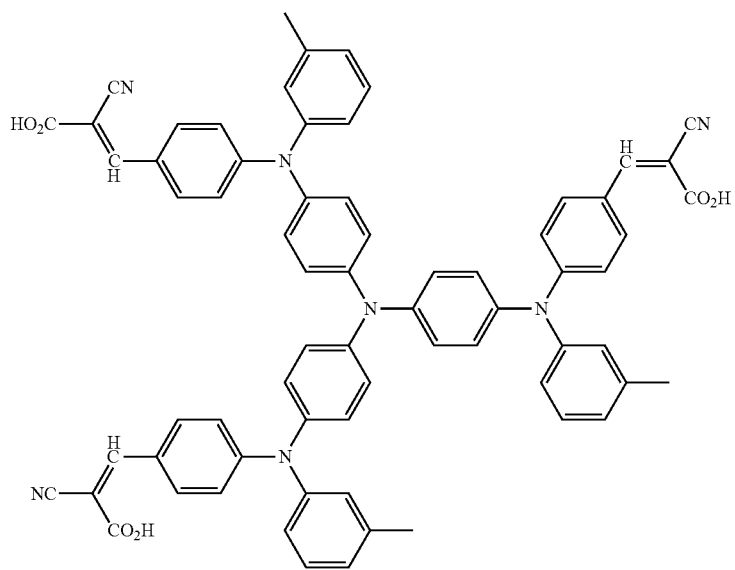
B-21

B-22
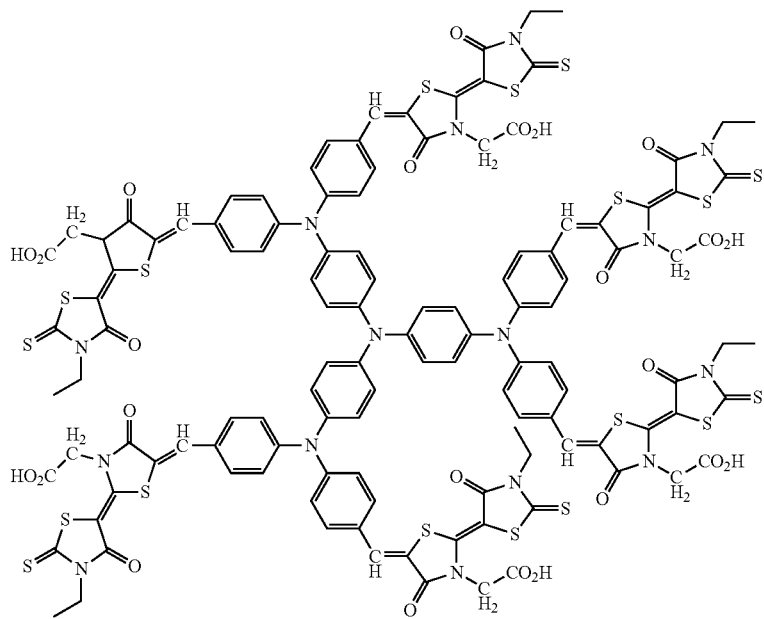
B-23
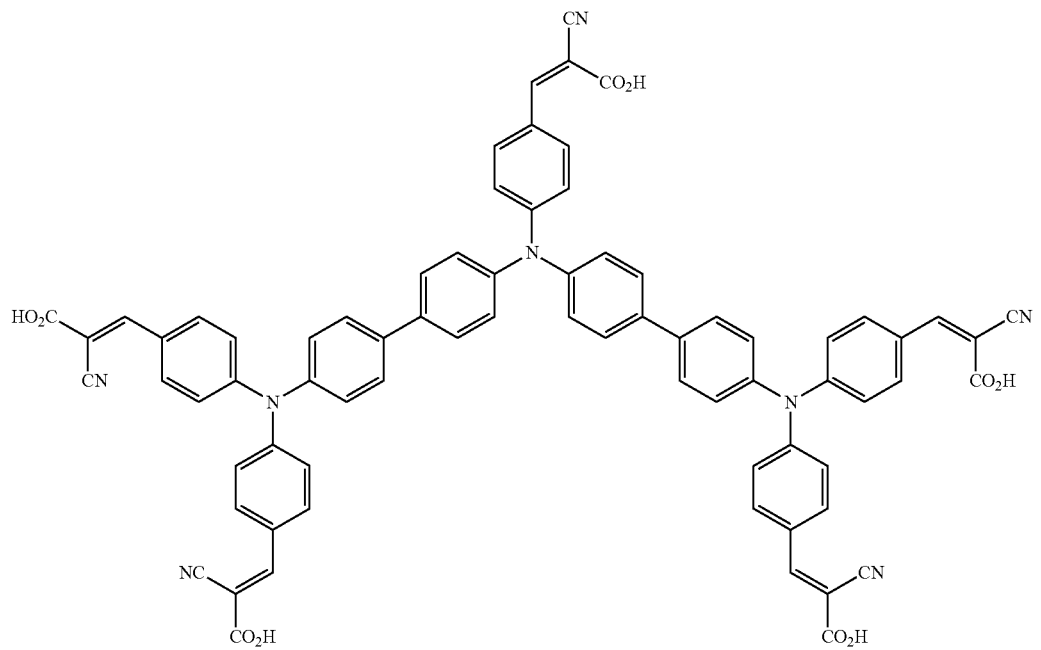

[Chem. 18]
B-24
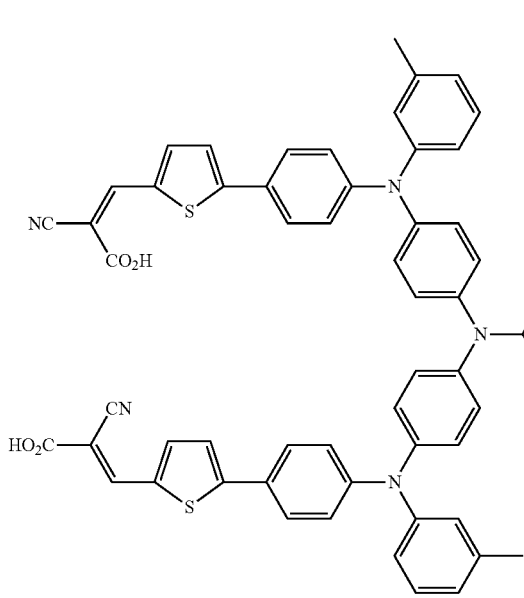
B-25
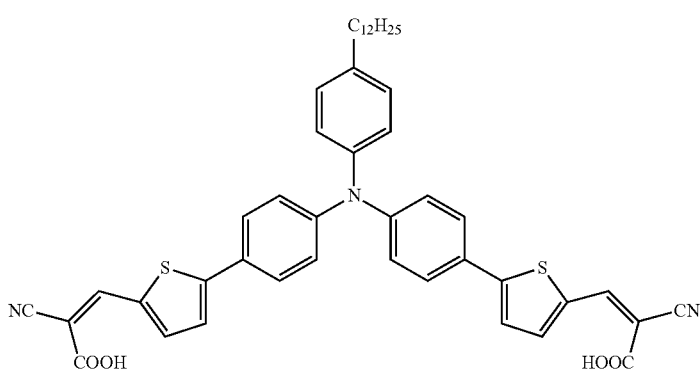
B-26
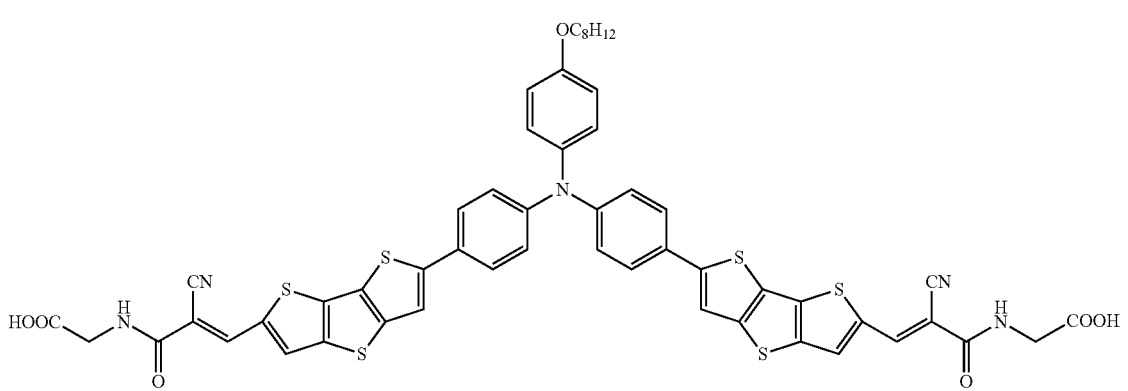
B-27
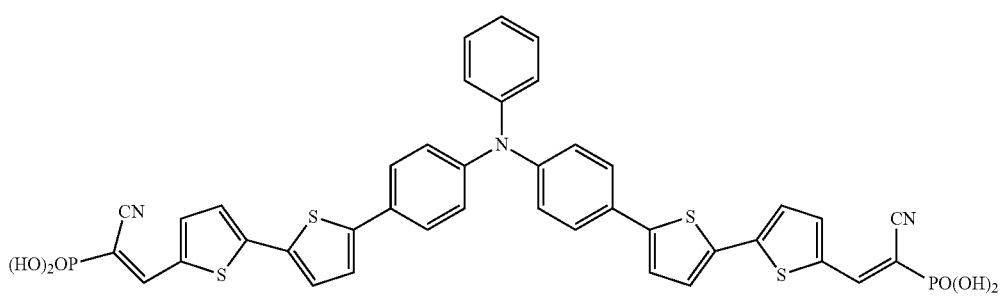

[Chem. 19]
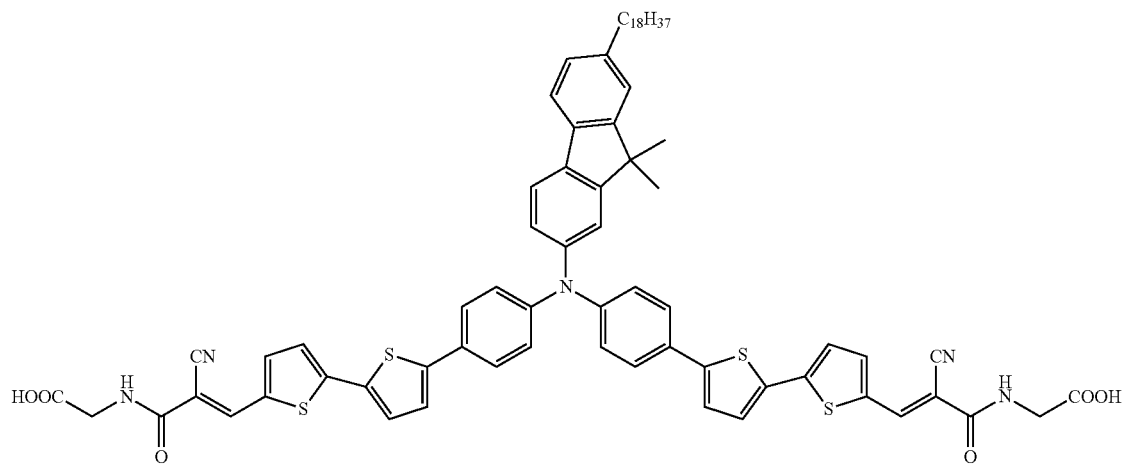
B-28
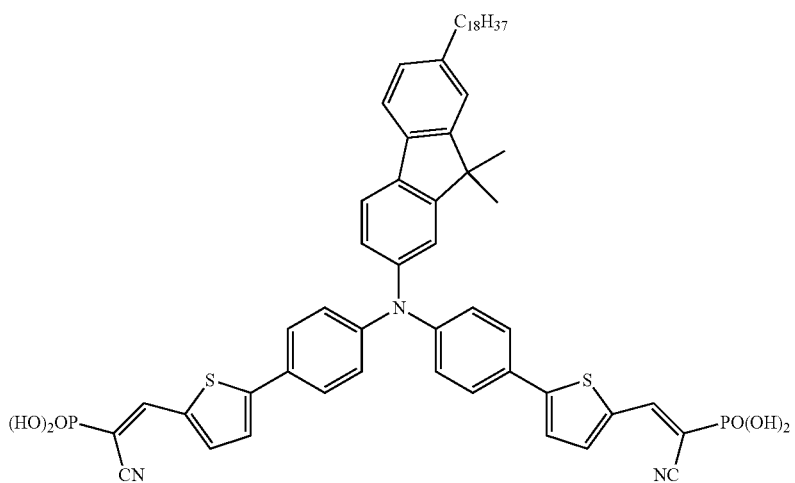
B-29
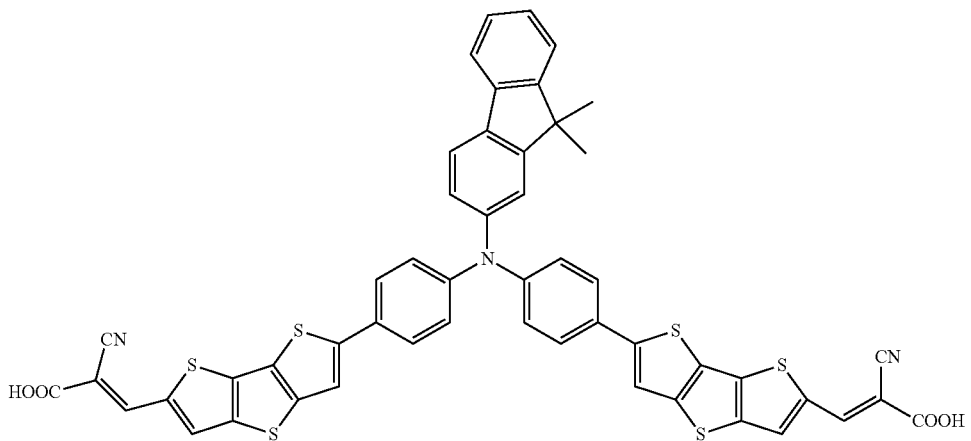
B-30

-continued
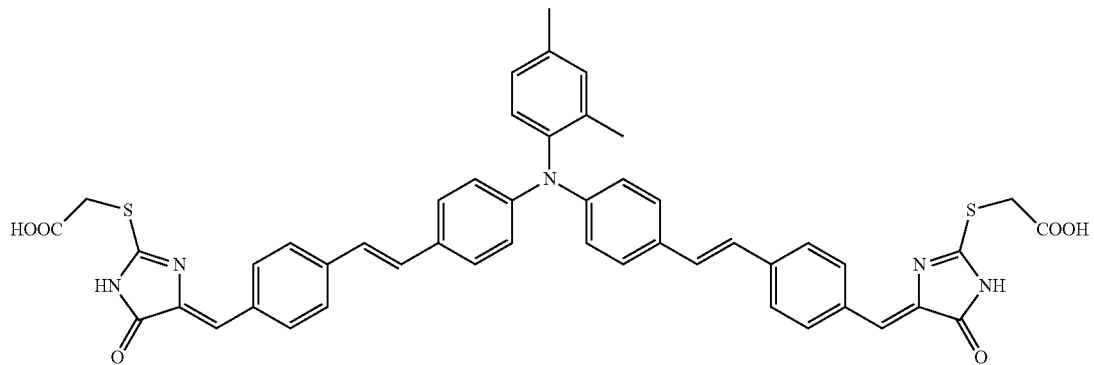
B-31
[Chem. 20]
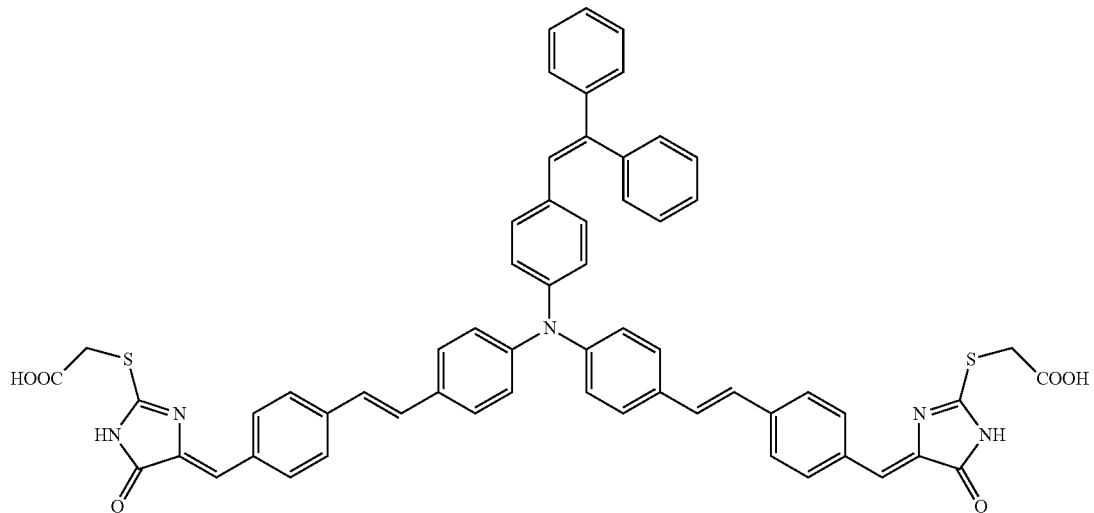
B-32
[Chem. 21]
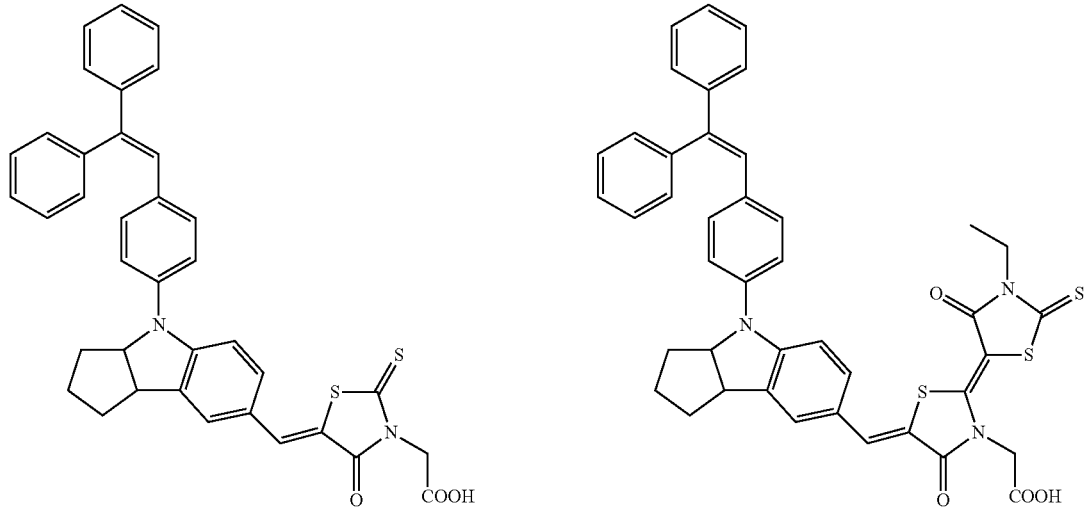
C-1  C-2

-continued
C-3
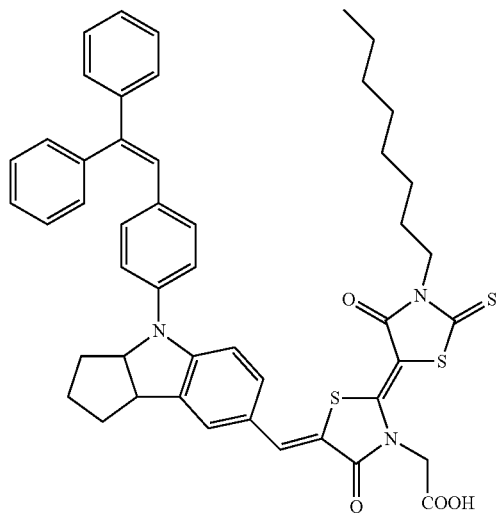
C-4
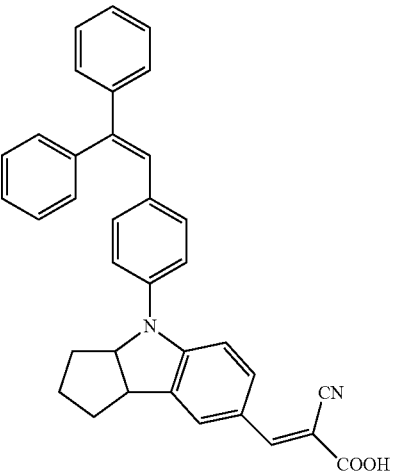
C-5
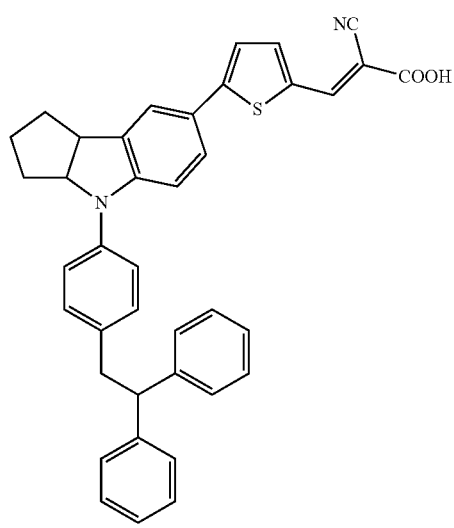
C-6
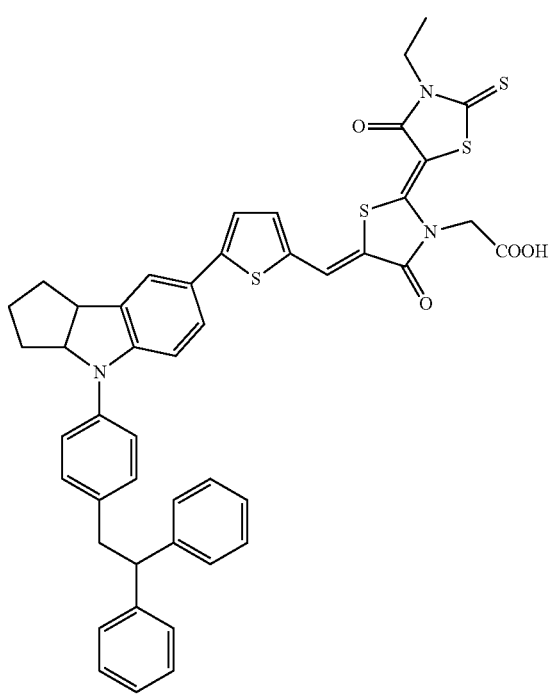
C-7
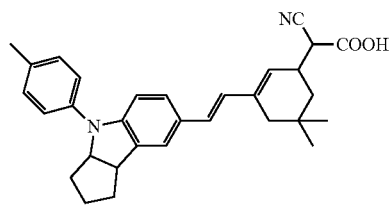
C-8
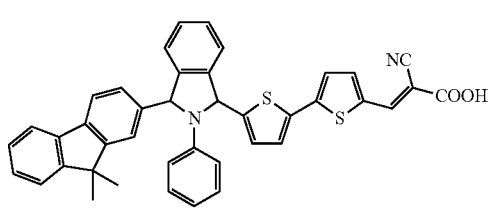

-continued
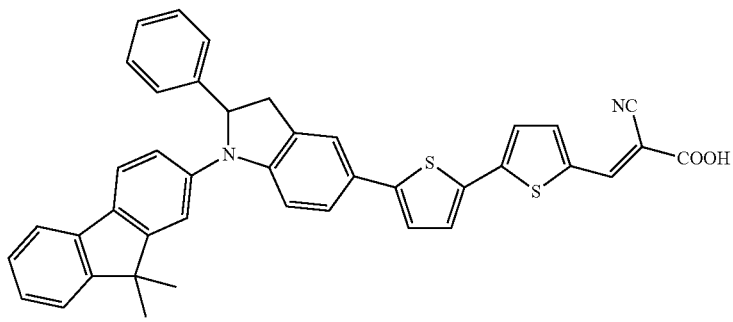
C-9
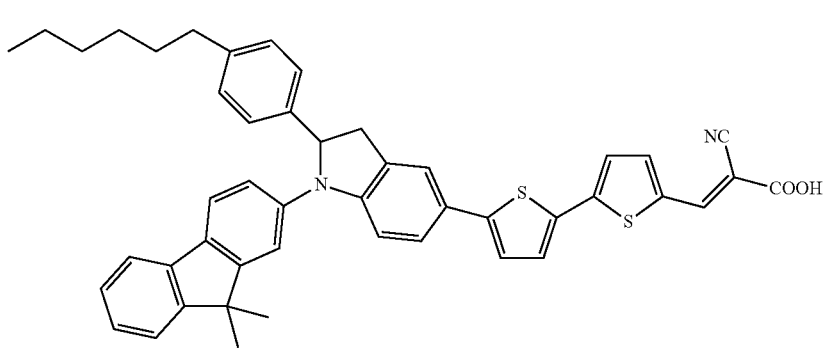
C-10
[Chem. 22]
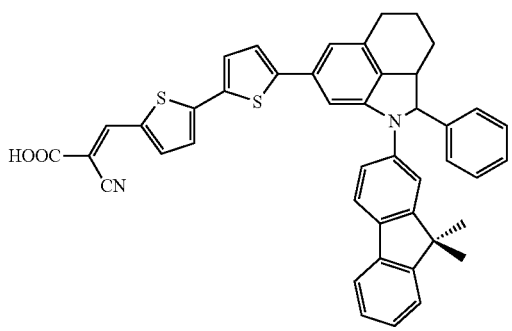
C-11
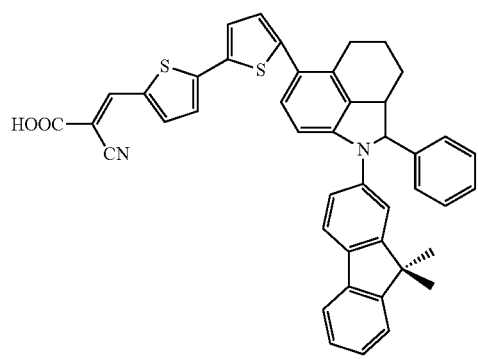
C-12
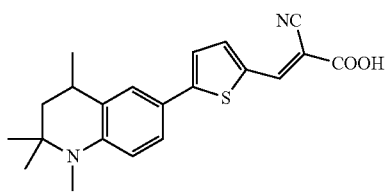
C-13
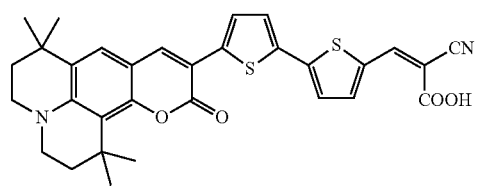
C-14

[Chem. 23]

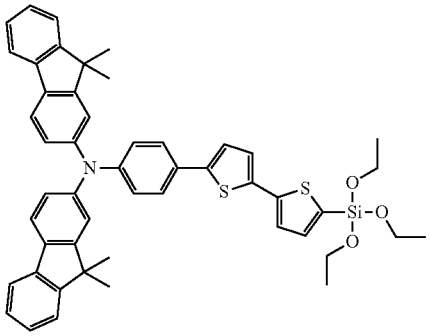

D-1

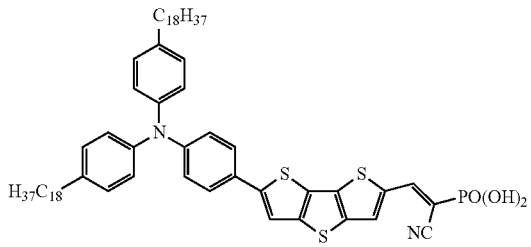

D-2

Among the above-mentioned preferable sensitizing pigments, sensitizing pigments wherein Ar has the chemical formula (1-B), and/or $R_3$ has any of the chemical formula (2-A), the chemical formula (2-G), the chemical formula (2-J) and the chemical formula (2-K), and/or $A_1$ and $A_2$ each has the chemical formula (3-D), the chemical formula (3-I), the chemical formula (3-P), the chemical formula (3-Q) or the chemical formula (3-R) are especially preferable.

"Hole Transport Layer"

The hole transport layer in the present invention has functions to feed electrons to the sensitizing pigment that has been oxidized by photoexcitation to thereby reduce the sensitizing pigment, and to transport holes that have generated on the interface with the sensitizing pigment to the second electrode. It is preferable that the hole transport layer is filled in not only the laminar part formed on the porous semiconductor layer but also in the parts in the airspaces of the porous semiconductor layer.

The hole transport layer in the present invention is formed by bringing the conductive polymer precursor into contact with the photoelectric conversion layer in the presence of an oxidizer, and irradiating the sensitizing pigment with light to polymerize the conductive polymer precursor.

Meanwhile, it is preferable to adjust the mixing ratio of the conductive polymer precursor to the oxidizer in the solution to be within the following mathematical formula (1). Specifically, it is preferable that the hole transport layer in the present invention is formed by bringing the above-mentioned photoelectric conversion layer into contact with a solution containing the conductive polymer precursor and the oxidizer by a ratio of the following mathematical formula (1):

[Math. 3]

$$0.1 < [Ox]/[M] \quad (1)$$

In the mathematical formula (1), [Ox] is the molar concentration of the oxidizer; and [M] is the molar concentration of the conductive polymer precursor. If the oxidizer is present in a larger amount than that of the conductive polymer precursor in such way, a more homogeneous hole transport layer can be formed as compared to that formed in photoelectrolytic polymerization, by conducting light irradiation (photochemical polymerization of the conductive polymer precursor), and thus the obtained photoelectric polymer conversion element can exert excellent durability. If the [Ox]/[M] ratio is 0.1 or less, the oxidizer is insufficient, and thus a homogeneous hole transport layer cannot be formed in some cases. The [Ox]/[M] ratio is preferably from 0.15 to 300, more preferably from 0.2 to 100.

Specifically, when the sensitizing pigment in the photoelectric conversion layer is irradiated with light, the electrons excited in the sensitizing pigment are consumed by the oxidizer (for example, aqueous hydrogen peroxide or the like). Therefore, the sensitizing pigment is put into a cation state, and the pigment in a cation state withdraws electrons from the conductive polymer precursor, whereby the conductive polymer precursor is put into a cation state. The conductive polymer precursor that has been put into a cation state acts as a trigger, whereby polymerization is initiated. Meanwhile, by mixing the oxidizer and the conductive polymer precursor at such a ratio that the oxidizer exists at a higher concentration than that of the conductive polymer precursor as in the present invention, the sensitizing pigment in a cation state efficiently withdraws electrons from the conductive polymer precursor, and thus the polymerization can be initiated more quickly by using the conductive polymer precursor that has been put into a cation state as a trigger.

Furthermore, when the conductive polymer precursor is a monomer of a relatively low molecule, the conductive polymer precursor easily enters into the inside of the photoelectric conversion layer of the porous body, and the sensitizing pigment in the photoelectric conversion layer acts as an initiator and also plays a role as a starting point of a polymerization reaction; therefore, the amount of the covering of the sensitizing pigment with the polymerized conductive polymer is considered to be larger than the amount of the covering of the sensitizing pigment with a conductive polymer polymerized by electrolytic polymerization.

Furthermore, since the above-mentioned process proceeds very quickly as compared to the process of electrolytic polymerization, it is possible to shorten the polymerization time, and this is very advantageous in the simplification of the production process. Furthermore, it is also possible to easily form a hole transport layer having a large surface area by the above-mentioned process.

Accordingly, the hole transport layer in the present invention has a conductive polymer formed by a photopolymerization reaction of a conductive polymer precursor by using a sensitizing pigment that has been oxidized by an oxidizer as a polymerization initiator. In more detail, the hole transport layer in the present invention contains a conductive polymer obtained by polymerizing a conductive polymer precursor by using a sensitizing pigment cation, which has been formed by oxidizing a sensitizing pigment by a reaction of electrons that are excited by irradiating the sensitizing pigment with light and an oxidizer.

As mentioned above, it becomes possible to polymerize the conductive polymer precursor by the presence of the sensitizing pigment, the light source for exciting the sensitizing pigment, and the oxidizer that deprives the sensitizing pigment of the excited electrons in the solution of the conductive polymer precursor for the hole transport layer. Furthermore, if the level of the oxidizer is higher than the level of the excited sensitizing pigment, it is possible to deprive the sensitizing pigment of the electrons. On the other hand, if the level of the oxidizer is too high, the conductive polymer precursor (for example, bis-EDOT) is directly subjected to oxidation polymerization, and thus it is possible that it becomes difficult to form a homogeneous film in the vicinity of the sensitizing pigment. Therefore, it is preferable to conduct polymerization with an oxidizer having a suitable standard electrode potential.

Considering the above-mentioned points, the oxidizer in the present invention has a standard electrode potential ($E^0_{(Ox)}$) (V) of preferably from −1.5 to +2.5 V, more preferably from −0.5 to +2.0 V. If the standard electrode potential of the oxidizer is at the lower limit or more, the polymerization can be promoted more efficiently. If the standard electrode potential of the oxidizer is at the upper limit or less, the reaction (reaction velocity) is easily controlled and the producibility is excellent, and this is industrially preferable. Specifically, since the oxidizer having such standard electrode potential ($E^0_{(Ox)}$) (V) can efficiently consume the electrons excited by the sensitizing pigment during the light irradiation, the polymerization of the conductive polymer precursor can further be promoted, and thus a more homogeneous film can be formed in the vicinity of the sensitizing pigment. In the present specification, "standard electrode potential ($E^0_{(Ox)}$) (V)" means a standard electrode potential (25° C.) in an aqueous solution.

Examples of the above-mentioned oxidizer include hydrogen peroxide, oxygen, methanol, metal salts and peroxides, and hydrogen peroxide, metal salts and organic peroxides [hydroperoxides (R—O—O—H), dialkylperoxides (R—O—O—R'), peroxy esters (R—C(=O)—O—O—R'), diacylperoxides (R—C(=O)—O—O—C(=O)—R'), peroxycarbonates (R—O—C(=O)—O—O—C(=O)—O—R'), peroxyketals (R—O—O—C(X) (X')—O—O—R') and ketoneperoxides (H—O—O—C(X) (X')—O—O—H)] are preferable. Specifically, the oxidizer used in the present invention is preferably hydrogen peroxide, oxygen, methanol, a metal salt or an organic peroxide.

Furthermore, the oxidizer in the present invention is preferably a compound that becomes a gas compound or a liquid compound by irradiation of light (by the reduction of the oxidizer itself). By that the oxidizer becomes a gas or a liquid after the polymerization reaction in such way, the oxidizer does not remain in the hole transport layer, which is a polymerized film, the durability of the obtained photoelectric conversion element can further be improved. In this specification, "gas compound" means a compound that is in a gas state under conditions of 20° C. and 1 atm. Furthermore, "liquid compound" means a compound that is in a liquid state under conditions of 20° C. and 1 atm.

It is considered that, when the sensitizing pigment is irradiated with light in the presence of the oxidizer, the electrons excited in the pigment are consumed by the oxidizer (for example, hydrogen peroxide/aqueous hydrogen peroxide or the like), and the sensitizing pigment in a cation state withdraws the electrons in the conductive polymer precursor as a monomer, and polymerization is initiated.

Examples of the above-mentioned peroxide include permanganese acid or salts thereof, chromate or salts thereof, peroxoacid or salts thereof, oxygen acid or salts thereof, nitric acids, sulfuric acids and the like, and specific examples include inorganic peroxides such as hydrogen peroxide, sodium peroxide, barium peroxide, potassium permanganate, sodium permanganate, metal chromates, metal dichromates, peroxodisulfate, ammonium peroxodisulfate, metal salt peroxodisulfates, peroxophosphate, peroxosulfate, sodium peroxoborate, hypochlorous acid, hypobromous acid, hypoiodous acid, hydrochloric acid, hydrobromic acid, hydroiodic acid, sodium hypochlorite, potassium hydrochlorite; organic peroxides such as cumenehydroperoxide, formic acid, performic acid, peracetic acid, perbenzoic acid, perphthalic acid, t-butylhydroperoxide, 1,1,3,3-tetramethylbutylhydroperoxide, diisopropylbenzenehydroperoxide, p-menthanehydroperoxide, di-t-butylperoxide, t-butylcumylperoxide, 2,5-dimethyl-2,5-di(t-butylperoxy)hexane, di-t-hexylperoxide, dicumylperoxide, di(2-t-butylperoxyisopropyl)benzene, n-butyl-4,4-di-(t-butylperoxy)valerate, t-butylperoxybenzoate, 2,2-di(t-butylperoxy)butane, t-butylperoxyacetate, 2,5-di-methyl-2,5-di (benzoylperoxy)hexane, t-hexylperoxybenzoate, t-butylperoxy 2-ethylhexylmonocarbonate, t-butylperoxy isopropylmonocarbonate, t-butylperoxylaurate, t-butylperoxy-3,5,5,-trimethylhexanoate, t-butylperoxymaleic acid, t-hexylperoxyisopropylmonocarbonate, 2,2-di(4,4-di-(t-butylperoxy)cyclohexyl)propane, 1,1-di(t-butylperoxy)cyclohexane, 1,1-di(t-hexylperoxy)cyclohexane, diisobutyrylperoxide, cumylperoxyneodecanoate, di-n-propylperoxydicarbonate, diisopropylperoxydicarbonate, di-sec-butylperoxydicarbonate, 1,1,3,3-tetramethylbutylperoxyneodecanoate, di(4-tert-butylcyclohexyl)peroxydicarbonate, di(2-ethylhexyl)peroxydicarbonate, t-hexylperoxyneodecanoate, t-butylperoxyneodecanoate, t-butylperoxyneoheptanoate, t-hexylperoxypivalate, t-butylperoxypivalate, di(3,5,5-trimethylhexanoyl)peroxide, dilauroylperoxide, 1,1,3,3-tetramethylbutylperoxy-2-ethylhexanoate, disuccinate peroxide, 2,5-dimethyl-2,5-di(ethylhexanoylperoxy)hexane, t-hexylperoxy-2-ethylhexanoate, di(3-methylbenzoyl)peroxide, benzoyl(3-methylbenzoyl) peroxide, dibenzoylperoxide, 1,1-di(t-butylperoxy)-2-methylcyclohexane and 1,1-di(t-hexylperoxy)-3,3,5-trimethylcyclohexane. The above-mentionedperoxides may be synthesized, or commercially available products may be used. In the above, the matter in the brackets represents a standard electrode potential ($E^0_{(Ox)}$) (V).

Examples of the above-mentioned metal salt include iron chloride (II), iron chloride (III), iron sulfate (III), iron nitrate (III), silver nitrate ($AgNO_3$), iron citrate (III), ammonium iron sulfate (III) and the like.

Besides the above-mentioned metal salts, an oxidizer having a standard electrode potential ($E^0_{(Ox)}$) of from −0.5 to +2.0 (V) may also be used, and as such examples, methanol (+0.588 V), oxygen (+1.229 V) and the like can be used.

Among the above-mentioned oxidizers, hydrogen peroxide (+1.763 V), cumene hydroperoxide, formic acid (+0.034 V), iron chloride (II) (−0.440V), silver nitrate ($AgNO_3$) (+0.799 V), methanol and oxygen (+1.229V) are preferable, and hydrogen peroxide, methanol and oxygen (+1.229 V) are more preferable.

The conductive polymer precursor the present invention is preferably a monomer component having a repeating unit represented by the following Monomer formula 1.

[Chem. 24]

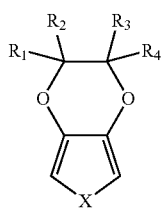

(Monomer formula 1)

In the above-mentioned monomer formula 1, X represents, S, NR or O, said R is any of a hydrogen atom and an alkyl group, and $R_1$ to $R_4$ are each independently a hydrogen atom, a halogen atom, a straight chain or branched alkyl group having 1 to 30 carbon atom(s), a cycloalkyl group having 3 to 10 carbon atoms, an alkoxy group having 1 to 30 carbon atom (s), a polyethylene oxide group having 2 to 30 carbon atoms, or a substituted or unsubstituted cyclic compound-containing group having 4 to 30 carbon atoms.

Since the straight chain or branched alkyl group having 1 to 30 carbon atom(s), the cycloalkyl group having 3 to 10 carbon atoms, and the alkoxy group having 1 to 30 carbon atom (s) mentioned above are similar to those in the general formula (1), these are abbreviated here.

Furthermore, the halogen atom is not especially limited, and examples include a fluorine atom, a chlorine atom, a bromine atom or an iodine atom.

The polyethylene oxide group having 2 to 30 carbon atoms is groups represented by the formula: —$(CH_2CH_2O)_xH$ or the formula: —$(OCH_2CH_2)_xH$ [wherein x is an integer of from 1 to 9]. Of these, groups wherein x is from 3 to 9 are preferable, and —$(OCH_2CH_2)_9H$ is more preferable.

The cyclic compound group having 4 to 30 carbon atoms is derived from a group formed by removing one hydrogen element from a benzene ring, a naphthalene ring, an anthracene ring, a thiophene group, a phenylthiophene group, a diphenylthiophene group, an imidazole ring, an oxazole ring, a thiazole ring, a pyrrole ring, a furan ring, a benzimidazole ring, a benzoxazole ring, a rhodanine ring, a pyrazolone ring, an imidazolone ring, a pyran ring, a pyridine ring, a fluorene ring or the like.

More preferable $R_1$ to $R_4$ in the general formula (2) in the present invention are each independently a hydrogen atom, a halogen atom, an alkyl group having a carbon number of 6 to 24, an alkoxy group having a carbon number of 1 to 18, a phenyl group, a biphenyl group, a phenyl group substituted with alkyl group(s) having a carbon number of 1 to 8, a biphenyl group substituted with alkyl group(s) having a carbon number of 1 to 8, a thiophene group, bithiophene group, a thiophene group substituted with alkyl group(s) having a carbon number of 1 to 8, a bithiophene group substituted with alkyl group (s) having a carbon number of 1 to 8, a thiophene group substituted with alkoxy group(s) having a carbon number of 1 to 8, a bithiophene group substituted with alkoxy group(s) having a carbon number of 1 to 8.

Furthermore, the conductive polymer precursor in the present invention may be any one as long as it has the above-mentioned formula (1) and plays a role of polymerization. Therefore, the above-mentioned formula (1) may be used singly, or as a multimer in which plural kinds of repeating units are bonded. Furthermore, the conductive polymer precursor may be a prepolymer formed by polymerizing a monomer having the above-mentioned repeating unit in advance, singly or together with plural kinds of monomers (multimers of dimer or more, and so-called oligomers are also encompassed). In this case, the conductive polymer precursor is a prepolymer, and as is also described in the following synthesis method, a method for forming a conductive polymer by applying the conductive polymer precursor in the form of a prepolymer on a photoelectric conversion layer, and conducting chemical polymerization on the photoelectric conversion layer may be convenient.

The repeating unit in the case when the conductive polymer precursor is a multimer is the following formula:

[Chem. 25]

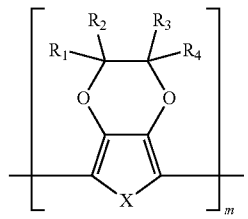

(Repeating unit formula 2)

In the repeating unit formula 2, X and $R_1$ to $R_4$ are the same as in the above-mentioned monomer formula 1, m represents the number of the bonds in the monomer, and for example, a dimer is represented in the case when m=2, and a trimer is represented in the case when m=3. Here, m is preferably an integer of 1 or more and 10 or less.

Furthermore, especially preferable embodiments of the conductive polymer precursor in the present invention will be shown below in Table 1.

TABLE 1

| Repeating unit | n | R1 | R2 | R3 | R4 |
|---|---|---|---|---|---|
| M1-1 | 2 | —H | —H | —H | —H |
| M1-2 | 2 | —H | —H | —C6H13 | —H |
| M1-3 | 2 | —H | —H | —C10H21 | —H |
| M1-4 | 2 | —H | —H | —C14H29 | —H |
| M1-5 | 2 | —H | —H | —C18H37 | —H |
| M1-6 | 2 | —H | —H | —C24H49 | —H |
| M1-7 | 2 | —H | —H | C9H19 (isopropyl-branched) | —H |
| M1-8 | 3 | —H | —H | (CH2)7 branched group | —H |
| M1-9 | 2 | —H | —H | cyclopropyl | —H |
| M1-10 | 2 | —H | —H | cycloheptyl | —H |
| M1-11 | 2 | —H | —H | —OCH3 | —H |
| M1-12 | 1 | —H | —H | —OC10H21 | —H |

TABLE 1-continued

| Repeating unit | n | R1 | R2 | R3 | R4 |
|---|---|---|---|---|---|
| M1-13 | 2 | —H | —H | —OC18H37 | —H |
| M1-14 | 1 | —H | —H | —OC2H5 / (OC2H4)8 | —H |
| M1-15 | 2 | —H | —H | (phenyl-methyl group) | —H |
| M1-16 | 2 | —H | —H | (biphenyl-methyl group) | —H |
| M1-17 | 2 | —H | —H | C6H13 (phenyl) | —H |
| M1-18 | 2 | —H | —H | C6H13-biphenyl | —H |
| M1-19 | 2 | —H | —H | thienyl-OC6H13 | —H |
| M1-20 | 2 | —H | —H | bithienyl-OC8H17 | —H |
| M1-21 | 3 | —H | —H | —Cl | —H |
| M1-22 | 2 | —H | —CH3 | —C14H29 | —H |
| M1-23 | 2 | —H | —H | —CH3 | —C4H9 |
| M1-24 | 2 | —H | —C10H21 | —C10H21 | —H |
| M1-25 | 2 | —H | —CH3 | —CH3 | —C6H13 |
| M1-26 | 2 | C2H5 | C2H5 | C2H5 | C2H5 |

It is preferable that the conductive polymer in the present invention has the repeating unit represented by the following general formula (2):

[Chem. 26]

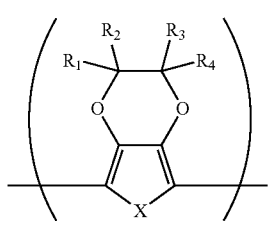

General formula (2)

In the above-mentioned general formula (2), X represents S, NR or O, the R is any of a hydrogen atom and an alkyl group, $R_1$ to $R_4$ each independently represents a hydrogen atom, a halogen atom, a straight chain or branched alkyl group having 1 to 30 carbon atom(s), a cycloalkyl group having 3 to 10 carbon atoms, an alkoxy group having 1 to 30 carbon atom (s), a polyethylene oxide group having 2 to 30 carbon atoms, or a substituted or unsubstituted cyclic compound-containing group having 4 to 30 carbon atoms.

The preferable substituents ($R_1$ to $R_4$) and X in the above-mentioned general formula (2) are the same as in the above-mentioned repeating unit.

It is difficult to figure out the polymerization degree of the conductive polymer in the present invention from the polymer obtained by the synthesis method therefor. However, since the solvent solubility of a hole transport layer formed after the polymerization significantly decreases, whether the conductive polymer is a polymer or not can be judged by the solubility of the hole transport layer by immersing the hole transport layer in tetrahydrofuran (THF), which can dissolve the polymer. Specifically, 60 mg of a compound (conductive polymer) is put into a sample vial of 25 mL, 10 ml of THF is added thereto, and the compound is irradiated with a ultrasonic wave (25 kHz, 150 W, Ultrasonic Industry, COLLECTOR CURRENT 1.5 A manufactured by Ultrasonic Industry 150) for 5 minutes, and in the case when the solved compound is 5 mg or less, the compound is judged to be polymerized.

The hole transport layer in the present invention contains the conductive polymer represented by the general formula (2), and where necessary, the hole transport layer may contain at least one selected from electrolytes and additives as components.

The above-mentioned electrolytes include a dispersion of a redox electrolyte and a support electrolyte. As the redox electrolyte, an $I^-/I^{3-}$-based, a $Br^-/Br^{3-}$-based, and a quinone/hydroquinone-based redox electrolytes and the like can be used. The above-mentioned dispersion of a redox electrolyte can be obtained by a known method. For example, an $I^-/I^3$-based electrolyte can be obtained by mixing iodide ion and iodine. The above-mentioned dispersion of a redox electrolyte is called as a liquid electrolyte when used in the form of a liquid, a solid polymer electrolyte when dispersed in a polymer that is a solid at room temperature (25° C.), and a gel electrolyte when dispersed in a gel-like substance. In the case when a liquid electrolyte is used as a hole transport layer, an electrochemically inactive solvent is used as a solvent therefor. As the solvent, for example, acetonitrile, propylene carbonate, and ethylene carbonate and the like are used. In the case when a solid polymer electrolyte is used, the electrolyte described in JP 2001-160427A can be referred to, and in the case when a gel electrolyte is used, the electrolyte described in "Surface Science" Vol. 21, No. 5, pages 288 to 293 can be referred to, respectively.

As the above-mentioned support electrolyte, an ionizable support electrolyte is used, and the ionizable support electrolyte is not specifically limited, but an ionizable support electrolyte that is difficult to be oxidized and reduced is preferably used. Specific examples preferably include salts such as lithium perchlorinate ($LiClO_4$), lithium tetrafluoroborate, tetrabutylammonium perchlorate, $Li[(CF_3SO_2)_2N]$ (lithium bistrifluoromethanesulfonylimide), $(n-C_4H_9)_4NBF_4$, $(n-C_4H_9)_4NPF_4$, p-toluenesulfonate and dodecylbenzenesulfonate. Furthermore, the polymer electrolyte described in JP 2000-106223 A (for example, PA-1 to PA-10 in this publication) may also be used as the support electrolyte. The above-mentioned support electrolytes may be used singly, or two or more kinds may be mixed and used.

On the other hand, as mentioned above, in the case when the polymer is formed by using a prepolymer as the conductive polymer precursor on the photoelectric conversion layer, the polymerization can be conducted by using a mixture containing, together with the prepolymer, a solvent, and additives such as a polymerization catalyst and a polymerization velocity adjusting agent as necessary.

The above-mentioned polymerization catalyst is not especially limited, and examples include iron chloride (III), iron (III) tris-p-toluenesulfonate, iron (III) p-dodecylbenzenesulfonate, iron (III) methanesulfonate, iron (III) p-ethylbenzenesulfonate, iron (III) naphthalenesulfonate, and hydrates thereof, and the like. In the present invention, as mentioned above, since the sensitizing pigment acts as a polymerization initiator, it is not necessary to add a polymerization catalyst, but in the case when it is desirable to further promote and progress polymerization, a polymerization catalyst may be added as necessary.

Furthermore, the above-mentioned polymerization velocity adjusting agent is not especially limited as long as a weak complexing agent is present for the trivalent iron ion in the polymerization catalyst, and the polymerization velocity is decreased so that a film can be formed. For example, in the cases when the polymerization catalyst is iron chloride (III) and a hydrate thereof, aromatic oxysulfonic acids such as 5-sulfosalicylic acid can be used. Furthermore, in the cases when the polymerization catalyst is tris-p-toluenesulfonate iron (III), p-dodecylbenzenesulfonate iron (III), methanesulfonate iron (III), p-ethylbenzenesulfonate iron (III), naphthalenesulfonate iron (III), and hydrates thereof, imidazole and the like can be used.

The reaction condition of the above-mentioned chemical polymerization differs depending on the prepolymer used, and the kinds, ratios and concentrations of the polymerization catalyst and polymerization velocity adjusting agent that are added as necessary, the thickness of the liquid film at the application stage, and the desired polymerization velocity, and preferable polymerization conditions are, in the case when heating is conducted in the air, a heating temperature of preferably from 25 to 120° C. and a heating time of preferably from 1 minute to 24 hours. Preferably, as is specifically described below, the chemical polymerization is conduct by irradiating light.

The hole transport layer in the present invention is preferably a solid hole transport layer. Therefore, as the material for said solid hole transport layer, the above-mentioned solid polymer electrolyte is preferably used.

Where necessary, for example, various additives such as acceptor dopants such as $N(PhBr)_2SbCl_6$, $NOPF_6$, $SbCl_5$, $I_2$, $Br_2$, $HClO_4$, $(n-C_4H_9)_4ClO_4$, trifluoroacetic acid, 4-dodecylbenzenesulfonic acid, 1-naphthalenesulfonic acid, $FeCl_2$, $AuCl_3$, $NOSbF_6$, $AsF_5$, $NOBF_4$, $LiBF_4$, $H_3[PMo_{12}O_{40}]$ and 7,7,8,8-tetracyanoquinodimethane (TCNQ), binder resins that are difficult to trap holes, and agents for improving application property such as a levelling agent may be added to the hole transport layer in the present invention. The above-mentioned additives may be used singly or by mixing two or more kinds.

It is preferable that the material contained in the hole transport layer has a large band gap so that the light absorption by the sensitizing pigment is not inhibited. Specifically, the material has preferably a band cap of 2 eV or more, further preferably a band cap of 2.5 eV or more. Furthermore, it is preferable that the hole transport layer has a low ionization potential so as to reduce sensitizing pigment holes. The value of the ionization potential varies depending on the sensitizing pigment to be applied, and generally, the value is preferably from 4.5 to 5.5 eV, more preferably from 4.7 to 5.3 eV.

In the case when the semiconductor layer is a porous body, it is not easy to measure the average thickness of the hole transport layer in the present invention due to permeation into the insides and gaps of the porous body.

{Method for Producing Photoelectric Conversion Element}

The second of the present invention is a method for producing a photoelectric conversion element containing a substrate, a first electrode, a photoelectric conversion layer containing a semiconductor and a sensitizing pigment, a hole transport layer having a conductive polymer, and a second electrode, the method including the steps of: step (1): forming the photoelectric conversion layer on the substrate including the first electrode on the surface, step (2): bringing the conductive polymer precursor into contact with the photoelectric conversion layer in the presence of an oxidizer, step (3): irradiating the sensitizing pigment with light in the presence of the oxidizer to polymerize the conductive polymer precursor to thereby form the hole transport layer, and step (4): forming the second electrode. In the above-mentioned step (2), it is preferable that the above-mentioned conductive polymer precursor and oxidizer are brought into contact at a ratio of the following mathematical formula (1):

[Math. 4]

$$0.1 < [Ox]/[M] \quad (1)$$

wherein in the mathematical formula (1), [Ox] is the molar concentration of the oxidizer; and [M] is the molar concentration of the conductive polymer precursor.

As mentioned above, the hole transport layer in the present invention is formed by not electrolytic polymerization but chemical polymerization. Therefore, as mentioned above, the present invention can solve the problems that a sufficient amount of conductive polymer cannot be formed by polymerization under a low voltage so as to prevent the deterioration of the sensitizing pigment, the problem that the producibility is decreased due to a long polymerization time by the polymerization under a low voltage, or the problem that it is difficult to form a homogeneous conductive polymer on the entirety of a photoelectric conversion element since it is difficult to homogeneously apply a voltage in conventional electrolytic polymerization in the production of the photoelectric conversion element with an enlarged surface area.

In the case when the hole transport layer is formed by electrolytic polymerization, a problem that, when a —COOH group is present in a sensitizing pigment, $CO_2$ is detached by an applied voltage (Kolbe electrolysis) and thus a pigment is decomposed, has been reported (for example, see JP 2011-065751 A). However, since the hole transport layer is formed by chemical polymerization in the present invention, the problem of the decomposition of the sensitizing pigment can be solved, and thus a pigment having a carboxylic acid (carboxyl group) can be preferably used.

Hereinafter the method for the production of the photoelectric conversion element according to the present invention will be explained in detail for the respective steps.

"Step (1)"

In the method for producing the photoelectric conversion element according to the present invention, the step (1) of forming the above-mentioned photoelectric conversion layer on the substrate including the first electrode on the surface is divided into a method for producing the first electrode including forming the first electrode on the substrate and a method for forming the photoelectric conversion layer, and where necessary, a method including forming the first electrode on the substrate, and then forming a buffer layer may also be provided. The respective methods will be explained in detail.

(Method for Producing First Electrode)

As the method for producing the first electrode in the present invention, i.e., a method for forming a first electrode (or also referred to as a transparent conductive layer) on a substrate, a suitable method can be selected depending on the material of the transparent conductive layer. Examples of such method include a sputtering process and a CVD process (a vapor deposition process), a SPD process (a spray pyrosis deposition process), a deposition process and the like. By these methods, a thin film formed of ITO, FTO, $SnO_2$ or the like is formed. If the transparent conductive layer is too thick, the light transmittivity is poor, whereas if the transparent conductive layer is too thin, the conductivity is poor. Therefore, considering the balance of the functions of light transmittivity and conductivity, the film thickness of the transparent conductive layer is preferably in the range of from about 0.3 to 3 µm.

Furthermore, in the case when the transparent conductive layer is formed into slits, a suitable method can be selected depending on the material of the transparent conductive layer. Specific examples include processing by excimer laser, YAG laser, $CO_2$ laser, airjet or waterjet, etching processing, mechanical processing and the like. By this way, the transparent conductive layer can be separated into plural regions. The pitch of the slits can be suitably preset depending on the size of the cell of the photoelectric conversion element.

(Method for Forming Buffer Layer)

The method for forming a buffer layer in the present invention includes a method including covering the first electrode with a buffer layer precursor, which is a component for forming the buffer layer, and conducting a thermal treatment as necessary. Specifically, a method including forming an (application) layer of the component for forming the buffer layer on the transparent conductive substrate (the first electrode) in which the first electrode in the present invention is formed on the surface of the substrate, and progressing a reaction by a CVD process or a calcination process to form a buffer layer, an inkjet method using an application liquid for forming a buffer layer, application by a spin coat process, and an atom layer deposition (ALD) process are preferable. Among these, the method mentioned below, which includes forming an (application) layer of the component for forming the buffer layer on the transparent conductive substrate (the first electrode) in which the first electrode in the present invention is formed on the surface of the substrate, and progressing a reaction by a CVD process or a calcination process to forma buffer layer is more preferable. The component for forming a buffer layer herein refers to a compound that becomes a buffer layer by a chemical reaction.

Furthermore, the component for forming a buffer layer used in the calcination process in the present invention is preferably a titanium oxide precursor, and the titanium oxide precursor is more preferably a titanium oxide precursor that generates titanium oxide by hydrolysis. Specific examples include organic titanium compounds such as halogenated titaniums (titanium trichloride, titanium tetrachloride and the like), orthotitanate esters (methyl orthotitanate, ethyl orthotitanate, isopropyl orthotitanate, butyl orthotitanate and the like), titanium butoxide dimer, titanium stearate, diiso-propoxytitanium distearate, tri-n-butoxytitanium monostearate, polyhydroxytitanium stearate titanacylate; titanium diisopropoxybis(acetylacetonate), titanium tetraacetylacetonate, titanium dioctyloxybis(octyleneglycolate), titanium diisopropoxybis(ethylacetacetate), titanium diisopropoxybis(triethanol aminate), titanium lactate ammonium salt, titanium lactate, propanedioxytitanium bis(ethyl acetacetate) and the like. Among these, orthotitanate esters are preferable. These titanium oxide precursors may be mixed with various ligands (for example, acetylacetone, aminoethanol, diethanolamine, triethanolamine, ethylenediamine, other amines, pyridinecarboxylic acid, tartaric acid, oxalic acid, lactic acid, glycolic acid, other hydroxycarboxylic acids and the like) in advance to hydrolysis to thereby form a complex of the titanium oxide precursor, and the complex may be used for the hydrolysis. Furthermore, it is preferable to use these titanium oxide precursors used for the calcination process as a solution by dissolving in a solvent.

As the solvent for dissolving the titanium oxide precursor, water, alcohols (methanol, ethanol, n-propanol, isopropanol), THF and the like are preferable.

In the case when the component for forming a buffer layer in the present invention is a solution, it is preferable to incorporate 0.5 to 13 parts by mass of the component for forming a buffer layer in 100 parts by mass of the above-mentioned solvent.

The CVD process is called as Chemical Vapor Deposition, and is a method including forming a desired titanium oxide layer on a substrate by deposition, by feeding a raw material substance (gas, liquid, solid) that has been formed into a gas to a reaction chamber in an apparatus, and causing a chemical reaction (gas phase reaction) on the surface of the substrate. Since it is necessary to make the raw material substance chemically active (an excited state) in the CVD process, heat, plasma and light (laser light, ultra violet and the like) are used, the respective processes are called as a thermal CVD process, a plasma CVD process and a light CVD process.

As other method for forming the buffer layer in the present invention, in the case when the above-mentioned application liquid for forming a buffer layer is applied by an inkjet method, the inkjet head is preferably of a piezoelectric element system, and the amount of discharge and the number of discharge are suitably selected. Alternatively, the above-mentioned application liquid for forming a buffer layer may be applied by a known method such as a doctor blade process, a squeegee process, a spin coat process or a screen print process.

As mentioned above, the buffer layer in the present invention can be obtained by applying the application liquid for forming a buffer layer on the transparent conductive substrate, and drying or/and sintering the application liquid. Furthermore, it is generally preferable to apply the application liquid for forming a buffer layer on the transparent conductive substrate, and thereafter immediately conducting drying or/and sintering, in view of improvement of conductivity. In addition, that the buffer layer contains titanium oxide may be that the buffer layer has a —Ti—O— bond, and the buffer layer of the photoelectric conversion element in the present invention may contain a buffer layer precursor whose bonds have not reacted, and for example, may include an organic substance such as an unreacted titanium oxide precursor.

The conditions for the calcination method for forming the buffer layer by calcining the component for forming a buffer layer in the present invention are suitably selected depending on the kind of the compound used, and for example, the calcination treatment temperature is preferably from 200 to 700° C., more preferably from 300 to 600° C. Furthermore, the calcination treatment time is preferably from 0.5 to 120 minutes, and more preferably is a method including calcining for 5 to 30 minutes.

(Method for Forming Photoelectric Conversion Layer)

[Method for Preparing Semiconductor Layer]

The method for preparing the semiconductor layer in the step (1) of the formation of the photoelectric conversion layer in the present invention will be explained below. As mentioned above, the preferable photoelectric conversion layer in the present invention is formed by flocculating a semiconductor having a sensitizing pigment carried by the surface thereof.

In the case when the semiconductor in the semiconductor layer is in a particulate form, (1) a method for preparing a semiconductor layer by applying or spraying a dispersion liquid or colloid solution of a semiconductor (a semiconductor-containing application liquid) onto a conductive substrate; (2) a method including applying a precursor of semiconductor microparticles onto a conductive substrate, hydrolyzing the precursor with moisture (for example, moisture in the air), and then conducting condensation (a sol-gel process), and the like can be used. The method of the above-mentioned (1) is preferable. In the case when the semiconductor in the present invention is in a film-like form and is not retained on the conductive substrate, it is preferable to prepare the semiconductor layer by attaching a semiconductor onto a conductive substrate.

A preferable embodiment of the method for preparing the semiconductor layer in the present invention include a method including forming the semiconductor layer by calcination using microparticles of a semiconductor onto the above-mentioned conductive substrate.

In the case when the semiconductor layer in the present invention is prepared by calcination, it is preferable to conduct a treatment for sensitizing the semiconductor (adsorption, filling into a porous layer or the like) by using a pigment treatment after the calcination. After the calcination, it is especially preferable to quickly conduct a treatment for adsorbing the compound before the semiconductor adsorbs water.

The semiconductor layer that is preferably used in the present invention will be explained below in detail for a method of forming the semiconductor layer by calcination using a semiconductor micropowder.

<Preparation of Semiconductor-Containing Application Liquid>

Firstly, an application liquid containing a semiconductor, preferably a micropowder of a semiconductor (semiconductor-containing application liquid) is prepared. A finer primary particle size of the semiconductor micropowder is more preferable, and the primary particle size is preferably from 1 to 5,000 nm, more preferably from 2 to 100 nm. The application liquid containing the semiconductor micropowder can be prepared by dispersing the semiconductor micropowder in a solvent.

The semiconductor micropowder dispersed in the solvent is dispersed in the form of its primary particles. The solvent may be any one that can disperse the semiconductor micropowder, and is not especially limited. As the above-mentioned solvent, water, an organic solvent, a mixed liquid of water and an organic solvent are encompassed. As the organic solvent, alcohols such as methanol, ethanol and isopropanol, ketones such as methyl ethyl ketone, acetone and acetylacetone, hydrocarbons such as hexane and cyclohexane, cellulose derivatives such as acetyl cellulose, nitrocellulose, acetyl butyl cellulose, ethyl cellulose and methyl cellulose, and the like are used. Where necessary, surfactants, acids (acetic acid, nitrate and the like), viscosity adjusting agents (polyvalent alcohols such as polyethylene glycol, and the like), chelating agents (acetylacetone and the like) may be added to the application liquid. The range of the concentration of the semiconductor micropowder in the solvent is preferably from 0.1 to 70 mass %, further preferably from 0.1 to 30 mass %.

<Application of Semiconductor-Containing Application Liquid, and Treatment for Calcining Formed Semiconductor Layer>

The semiconductor-containing application liquid obtained as above is applied or sprayed onto the conductive substrate, drying and the like are conducted, and the application liquid is calcined in the air or an inert gas, whereby a semiconductor layer (also referred to as a semiconductor film) is formed on the conductive substrate. The application method is not especially limited, and examples include known methods such as a doctor blade process, a squeegee process, a spin coat process and a screen print process.

The coating obtained by applying the semiconductor-containing application liquid onto the conductive substrate and conducting drying is formed of an aggregate of the semiconductor microparticles, and the particle size of the microparticles corresponds to the primary particle size of the semiconductor micropowder used.

The semiconductor layer (semiconductor microparticle layer) formed in such way on the conductive layer such as the conductive substrate generally has a weak bonding force against the conductive substrate and a weak mutual bonding force of the microparticles, and thus has a weak mechanical intensity. Therefore, in order to increase the mechanical intensity to thereby give a semiconductor layer that is strongly fixed on the substrate, a treatment for calcining the semiconductor layer (semiconductor microparticle layer) is conducted.

Although the semiconductor layer may have any structure, it is preferably a porous structure film (also referred to as a porous layer having airspaces). In the case when the semiconductor layer is a porous structure film, it is preferable that the components of the hole transport layer such as the hole transportation substance are also present in the airspaces. The porosity of the semiconductor layer is not especially limited, and is preferably from 1 to 90% by volume, further preferably from 10 to 80% by volume, especially preferably from 20 to 70% by volume. The porosity (porosity) of the semiconductor layer means a porosity having permeability in the thickness direction of a dielectric, and can be measured by using a commercially available apparatus such as a mercury porosimeter (Shimadzu Poresizer Type 9220). Furthermore, although the film thickness of the semiconductor layer that has become a film of a calcined product having a porous structure is not especially limited, it is preferably at least 1 μm or more, further preferably from 2 to 30 μm. In such range, a semiconductor layer that is excellent in properties such as transmittivity and conversion efficiency can be formed. The semiconductor layer may be either a single layer formed by semiconductor microparticles having approximately the same average particle size, or a multi-layered film (laminar structure) containing semiconductor microparticles having different average particle sizes and kinds.

Furthermore, the conditions for the calcination are not especially limited. From the viewpoint of obtaining a calcined film having the above-mentioned porosity by suitably adjusting the actual surface area of the calcination film in the calcination treatment, the calcination temperature is preferably lower than 900° C., further preferably in the range of from 200° C. to 850° C., especially preferably in the range of from 450° C. to 800° C. Furthermore, in the case when the substrate is plastic or the like and thus is poor in heat-resistance, it is also possible to fix the microparticles and the microparticles-substrate by pressurization without conducting a calcination treatment at 250° C. or more, or the only the semiconductor layer can be subjected to a heat treatment by a microwave without heating the substrate. Furthermore, from the above-mentioned viewpoint, the calcination time is preferably in the range of from 10 seconds to 12 hours, more preferably in the range of from 1 to 240 minutes, especially preferably in the range of from 10 to 120 minutes. Furthermore, the calcination atmosphere is also not especially limited, but the calcination step is generally conducted in the air or an atmosphere of an inert gas (for example, argon, helium, nitrogen or the like). The above-mentioned calcination may be conducted only one time at a single temperature, or may be repeatedly conducted twice or more with changing the temperature and time.

Furthermore, the ratio of the actual surface area to the apparent surface area can be controlled by the particle size and specific surface area of the semiconductor microparticles, calcination temperature and the like. Furthermore, for example, chemical plating using an aqueous titanium tetrachloride solution or an electrochemical plating treatment using an aqueous trichloride titanium solution may be conducted for the purpose of enhancing the electron injection efficiency from the pigment to the semiconductor particles, by increasing the surface area of the semiconductor particles after the heating treatment, or increasing the purity in the vicinity of the semiconductor particles.

[Method for Sensitizing Treatment of Semiconductor Layer]

In the case when the sensitizing treatment in the present invention is conducted, the sensitizing pigments described above can be used singly, plural sensitizing pigments may be used in combination, or the sensitizing pigments can be used by mixing with other compounds (for example, the compounds described in U.S. Pat. Nos. 4,684,537, 4,927,721, 5,084,365, 5,350,644, 5,463,057, 5,525,440, JP 7-249790 A, JP 2000-150007 A and the like).

Especially in the case when the intended use of the photoelectric conversion element of the present invention is a solar cell mentioned below, it is preferable to use two or more kinds of pigments having different absorption wavelengths by mixing so that solar light can be effectively utilized by broadening the wavelength region of photoelectric conversion as possible.

The method for making the above-mentioned semiconductor layer carry the sensitizing pigment is not especially limited, and a known method can be applied in a similar manner or after suitable modification. For example, in order to make the semiconductor carry the sensitizing pigment, a method including dissolving the sensitizing pigment in a suitable solvent, and immersing the semiconductor layer that has been thoroughly dried in the solution is a general method. In conducting the sensitizing treatment by using plural sensitizing pigments in combination or using other pigment in combination, mixed solutions of the respective pigments may be prepared and used, or it is possible to prepare separate solutions for the respective pigments and sequentially immerse the semiconductor layer in the respective solutions. Furthermore, in the case when the preparation is conducted by preparing separate solutions for the respective sensitizing pigments and sequentially immersing in the respective solutions, the order of incorporating the sensitizing pigment and the like in the semiconductor may be any order. Alternatively, the preparation may be conducted by mixing microparticles of the semiconductor that has adsorbed the above-mentioned pigment singly, or the like.

Furthermore, in the case of a semiconductor having a high porosity, it is preferable to complete the treatment for adsorbing the sensitizing pigment and the like before water is adsorbed on the semiconductor layer and the airspaces in the semiconductor layer due to moisture, water vapor and the like in the airspaces.

As mentioned above, the treatment for sensitizing the semiconductor is conducted by dissolving the sensitizing pigment in a suitable solvent, and immersing the above-mentioned substrate on which the semiconductor has been calcined in the solution. At this time, it is preferable to subject the substrate on which the semiconductor layer (semiconductor film) has been formed by calcination to a treatment under a reduced pressure or a heating treatment in advance to thereby remove the airbubbles in the film. By this treatment, the sensitizing pigment becomes possible to enter into the portion deep inside of the semiconductor layer (semiconductor thin film), and this is especially preferable in the case when the semiconductor layer (semiconductor thin film) is a porous structure film.

The solvent used for dissolving the sensitizing pigment is not especially limited as long as the solvent can dissolve the sensitizing pigment but does not dissolve the semiconductor or react with the semiconductor. However, it is preferable to subject the semiconductor film to deaeration and distillation purification in advance so as to prevent a sensitizing treatment such as adsorption of the sensitizing pigment by entering of the moisture and gas dissolved in the solvent into the semiconductor film. Examples of the solvent that is preferably used in dissolving the sensitizing pigment include nitrile-based solvents such as acetonitrile, alcohol-based solvents such as methanol, ethanol, n-propanol, isopropanol and t-butyl alcohol, ketone-based solvents such as acetone and methyl ethyl ketone, ether-based solvents such as diethyl ether, diisopropyl ether, tetrahydrofuran and 1,4-dioxane, halogenated hydrocarbon solvents such as methylene chloride and 1,1,2-trichloroethane, and the like. These solvents may be used singly, or by mixing two or more kinds. Among these, acetonitrile, methanol, ethanol, n-propanol, isopropanol, t-butyl alcohol, acetone, methyl ethyl ketone, tetrahydrofuran and methylene chloride, and mixed solvents thereof such as acetonitrile/methanol mixed solvent, acetonitrile/ethanol mixed solvent and acetonitrile/t-butyl alcohol mixed solvent are preferable.

<Conditions for Sensitizing Treatment>

The conditions for the sensitizing treatment in the present invention is not especially limited. For example, the time for immersing the substrate on which the semiconductor has been calcined in the sensitizing pigment-containing solution is preferably a time such that the solution enters deep into the semiconductor layer (semiconductor film) to sufficiently progress the adsorption and the like to thereby sufficiently sensitize the semiconductor. Furthermore, from the viewpoint of preventing the decomposed product that is generated by the decomposition of the pigment in the solution and the like from inhibiting the adsorption of the pigment, the temperature for the sensitizing treatment is preferably from 0 to 80° C., more preferably from 20 to 50° C. Furthermore, from similar viewpoints, the time for the sensitizing treatment is preferably from 1 to 24 hours, and more preferably from 2 to 6 hours. It is especially preferable to conduct the sensitizing treatment under a condition of room temperature (25° C.) for 2 to 48 hours, especially for 3 to 24 hours. This effect is significant especially in the case when the layer is a porous structure film. However, the immersion time is a value under 25° C. condition, and is not limited to the above-mentioned value in the cases when the temperature condition is changed.

In the immersion, the solution containing the pigment in the present invention may be used by heating to a temperature at which the solution does not boil as long as the above-mentioned pigment is not decomposed. A preferable temperature range is from 5 to 100° C., further preferably from 25 to 80° C., but the temperature range is not limited to this range in the case when the solvent boils in the above-mentioned temperature range as mentioned above.

"Step (2)"

The step (2) in the method for producing a photoelectric conversion element in the present invention is such that the photoelectric conversion layer prepared in the above-mentioned step (1) and a conductive polymer precursor as a precursor for the conductive polymer that constitutes the hole transport layer are brought into contact in the presence of an oxidizer. Specifically, in the case when the semiconductor layer, which is the constitutional element of the photoelectric conversion layer, is not a porous body, a method including forming an oxidizer and a conductive polymer precursor, and where necessary, the electrolyte explained above, on the photoelectric conversion layer, or a method including applying a solution of an oxidizer, and a form of a monomer or a prepolymer as a precursor for the hole transport layer, and a solvent to which an electrolyte and the like have been added as necessary, onto a photoelectric conversion layer, and conducting polymerization to form a polymer is preferable. Furthermore, in the case when the semiconductor layer, which is the constitutional element of the photoelectric conversion layer, is a porous body, it is specifically preferable to bring the sensitizing pigment that has been adsorbed on the surface of the semiconductor layer and the hole transport layer in the presence of the oxidizer so that the surface of the porous body is covered with the hole transport layer, and it is specifically preferable to polymerize the conductive polymer by immersion and/or application so that the above-mentioned solution containing precursor for the hole transport layer and oxidizer and the electrolyte added as necessary would permeate into the inside and gaps of the porous body and cover approximately the whole surface of the porous body.

In this step (2), it is preferable that the photoelectric conversion layer prepared in the above-mentioned step (1) is brought into contact with a solution containing the conductive polymer precursor and the oxidizer by a ratio represented by the following mathematical formula (1):

[Math. 5]

$$0.1 < [Ox]/[M] \quad (1)$$

wherein in the mathematical formula (1), [Ox] is the molar concentration of the oxidizer; and [M] is the molar concentration of the conductive polymer precursor. When the oxidizer is present in a larger amount than that of the conductive polymer precursor in such way, a homogeneous hole transport layer can be formed by conducting light irradiation (photochemical polymerization of the conductive polymer precursor) as compared to photoelectrolytic polymerization, and thus the obtained photoelectric conversion element can exert excellent durability. When [Ox]/[M] ratio is 0.1 or less, the oxidizer is insufficient, and thus a homogeneous hole transport layer cannot be formed in some cases. The ratio [Ox]/[M] is preferably from 0.15 to 300, more preferably from 0.2 to 100.

Among these, a method including applying a solution to which an oxidizer, and a form of a monomer or a prepolymer as a precursor for the hole transport layer, and where necessary, a solvent, an electrolyte and the like have been added, onto a photoelectric conversion layer, and conducting polymerization to form a polymer, or a method including polymerizing the conductive polymer by immersion and/or application so that the above-mentioned solution containing the precursor for the hole transport layer and oxidizer and the electrolyte added as necessary would permeate and cover approximately the whole surface of the porous body is more preferable. Especially, since it is preferable that the semiconductor layer, which is the constitutional element of the photoelectric conversion layer is a porous body, an immersion process including immersing the photoelectric conversion layer in the solution containing the conductive polymer precursor and the oxidizer is especially preferable.

The composition of the solution to be applied onto the photoelectric conversion layer or in which the photoelectric conversion layer is to be immersed is preferably a composition such that the oxidizer is from 10 to 10,000 parts by mass, the support electrolyte is from 100 to 100,000 parts by mass, and the solvent is from 5,000 to 200,000 parts by mass, more preferably a composition such that the oxidizer is from 10 to 1,000 parts by mass, the support electrolyte is from 500 to 10,000 parts by mass, the solvent is from 10,000 to 1,000,000 parts by mass, with respect to 100 parts by mass of the conductive polymer precursor.

Furthermore, the above-mentioned solvent is not especially limited as long as it can dissolve the support electrolyte and the above-mentioned monomer or a multimer thereof, and examples include butylene oxide, chloroform, cyclohexanone, acetonitrile, tetrahydrofuran, propylene carbonate, dichloromethane, o-dichlorobenzene, dimethylformamide, dimethylsulfoxide, hexamethylphosphate triamide, dimethoxyethane, acetone, methanol, ethanol, propanol, isobutyl alcohol, t-butyl alcohol, methylene chloride and the like. Furthermore, the above-mentioned solvents may be used as a mixed solvent by adding water or other organic solvent as necessary. The above-mentioned solvent may be used singly, or by mixing two or more kinds.

Furthermore, as the application method in the case when the hole transport layer is formed by applying the above-mentioned solution onto the photoelectric conversion layer, various application processes such as dipping, dropwise addition, a doctor blade, spin coat, brush application, spray coat, a roll coater, air knife coat, curtain coat, wire bar coat, gravure coat, the extrusion coat using a hopper described in U.S. Pat. No. 2,681,294, and the simultaneous multilayer application processes described in U.S. Pat. Nos. 2,761,418, 3,508,947 and 2,761,791 can be specifically used. Furthermore, the stacking may be conducted by repeatedly conducting such operations for application. The number of application in this case is not especially limited and can be suitably selected depending on the thickness of a desired hole transport layer.

"Step (3)"

In the step (3) in the method for producing the photoelectric conversion element according to the present invention, the sensitizing pigment is irradiated with light in the presence of an oxidizer after the above-mentioned step (2), whereby the above-mentioned conductive polymer precursor is polymerized to form the hole transport layer. Specifically, it is preferable to irradiate the sensitizing pigment with light from outside in the state that the photoelectric conversion layer is immersed in a solution of the oxidizer and a form of a monomer or a prepolymer (multimer) that is a precursor of the hole transport layer, and a solvent to which an electrolyte and the like have been added as necessary. Alternately, the sensitizing pigment may be irradiated with light from outside in the state that the solution is applied onto the photoelectric conversion layer.

In the method for producing according to the present invention, although the condition for irradiating the photoelectric conversion layer (especially the sensitizing pigment in the photoelectric conversion layer) with light is not especially limited, it is preferable that the wavelength of the irradiated light includes the absorption wavelength of the sensitizing pigment. Specifically, it is preferable to use a light source having a wavelength of 400 nm or more, preferably from 400 to 1100 nm, more preferably a wavelength of more than 430 nm and 1100 nm or less. Furthermore, the intensity of the light is preferably from 10 to 150 mW/cm$^2$, more preferably from 20 to 80 mW/cm$^2$. The time for irradiating the sensitizing pigment with light is preferably from 0.1 to 30 minutes, more preferably from 0.5 to 15 minutes. When light with a wavelength of 400 nm or more is selectively irradiated, a titania photocatalyst action that is caused by light having a wavelength equal to or less than that wavelength is suppressed, and thus concern about the decomposition of the pigment is eliminated, and a photoelectric conversion element having stable properties can be formed also in the case when light is irradiated for a long time so as to form a thick hole transport layer. Furthermore, it is preferable to suppress irradiation of infrared ray at a wavelength of longer than 1,100 nm since heating due to excess irradiation can be suppressed, delamination can be suppressed, and a high photoelectric conversion efficiency can be obtained, and in the case when a hole transport layer having a polymer having the monomer formula 1 is used, side reactions such as decomposition of the polymer caused by overlapping of light at a wavelength of more than 1,100 nm with the absorption region of this polymer, and the like are suppressed, and thus stable properties can be obtained.

If the wavelength at which the sensitizing pigment is irradiated with light is 430 nm or less, a wavelength of preferably 420 nm or less, more preferably a wavelength of 400 nm or less is used, titania is excited, and thus a photocatalystic action acts on the pigment to decompose the pigment. Furthermore, light at a longer wavelength transmits deeper into the titania fine pores, although it is slightly different depending on the pigment, the polymerization proceeds more homogeneously. On the other hand, if the wavelength of the light source is a too long wavelength, the absorption of the pigment is conversely eliminated, and thus the polymerization does not progress. Therefore, the wavelength is set to be within the above-mentioned range. Furthermore, the amount of light is set to be within the above-mentioned range as an amount of light which is deemed to be necessary so as to transmit the light deep into the titania fine pores as mentioned above. Furthermore, the irradiation time represents a time in which the polymerization sufficiently proceeds within this range.

Examples of the light source in the present invention include a xenon lamp, a halogen lamp, an LED and the like.

As indicated in the following reaction formula, when the sensitizing pigment adsorbed by the photoelectric conversion layer is irradiated with light, the sensitizing pigment is excited by the light, and the excited electrons are consumed by the oxidizer, whereby the sensitizing pigment is put into a cation state. It is considered that the sensitizing pigment that has been put into a cation state withdraws electrons from the conductive polymer precursor, whereby the conductive polymer precursor is cationized and plays a role as a polymerization initiator.

[Chem. 27]

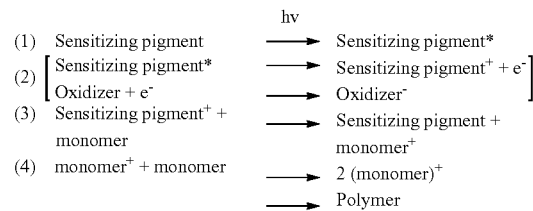

(Reaction formula)

By this way, since the conductive polymer can be formed by photopolymerization, the polymerization time can be shorten as compared to electrolytic polymerization, and thus a layer of a polymer can be easily formed on the surface of the photoelectric conversion layer (semiconductor layer) with a sufficient amount and finely. Furthermore, according to the above-mentioned method, the problem of decomposition of the sensitizing pigment can be solved, and a pigment having a carboxylic acid can be preferably used.

It is preferable to set the range of the temperature at which the application of the solution onto the photoelectric conversion layer and/or immersion of the photoelectric conversion layer in the solution to a range at which the solvent is not solidified or does not boil explosively, and the range is generally from −10° C. to 60° C.

Furthermore, after the formation of the hole transport layer on the photoelectric conversion layer in the step (3), where necessary, a step of washing by a known method using the above-mentioned solvent, and/or a step of drying under conditions of from 25 to 150° C. and from 0.2 to 12 hours may be conducted.

Furthermore, where necessary, in the step (3), after the formation of the conductive polymer by photopolymerizing the conductive polymer to thereby dispose the hole transport layer on the surface of the photoelectric conversion layer, the semiconductor electrode on which the hole transport layer has been formed may be immersed in a solution formed by mixing a solvent used for the immersion and/or application of the above-mentioned photoelectric conversion layer and at least one selected from the group consisting of the above-mentioned support electrolyte and the above-mentioned organic salt at from −10 to 70° C. for 0.1 to 2 hours for the purpose of improving the doping rate of the conductive polymer and prevention of reverse electron transfer from the titania to the hole transport layer. In such case, it is preferable to conduct the step (4) mentioned below by conducing immersion, and thereafter allowing to stand for 0.01 to 24 hours under natural drying.

"Step (4)"

The step (4) in the method for producing a photoelectric conversion element according to the present invention is a step of forming a second electrode on the above-mentioned hole transport layer after the above-mentioned step (3).

The method for forming the second electrode in the present invention is not especially limited, and a known method can be applied. For example, a method including depositing (including vacuum deposition), sputtering, applying or screening a material for the above-mentioned second electrode is preferably used.

The photoelectric conversion element of the present invention obtained as mentioned above can absorb light with a fine efficiency. Specifically, the absorbance at 1,000 nm ($A_{1000}$) of the photoelectric conversion element satisfies the following mathematical formula (2):

[Math. 6]

$$A_{1000} \geq FT_{sc}/8 \qquad (2)$$

In the above-mentioned mathematical formula (2), $A_{1000}$ is the absorbance at 1,000 nm of the photoelectric conversion element; and $FT_{sc}$ is the film thickness (μm) of the semiconductor layer.

(Solar Cell)

The photoelectric conversion element of the present invention can be preferably used especially for a solar cell. Therefore, the present invention also provides a solar cell having the photoelectric conversion element of the present invention or a photoelectric conversion element produced by the method of the present invention.

The solar cell of the present invention has the above-mentioned the photoelectric conversion element of the present invention. The solar cell of the present invention has the photoelectric conversion element of the present invention, the solar cell is designed and the circuit thereof is designed optimally for solar light, and thus has such a structure that optimal photoelectric conversion is conducted when solar light is used as a light source. In other words, it has a structure in which a pigment-sensitized semiconductor can be irradiated with solar light. In constituting the solar cell of the present invention, it is preferable to seal the above-mentioned photoelectric conversion layer, hole transport layer and second electrode by housing in a case, or seal the entirety thereof by a resin.

When the solar cell of the present invention is irradiated with solar light or an electromagnetic wave that is equal to solar light, the sensitizing pigment carried by the semiconductor excites by absorbing the irradiation light or electromagnetic wave. The electrons generated by the excitation transfer to the semiconductor, and then transfer to the second electrode through the conductive substrate and outer load, and are fed to the charge transfer material of the hole transport layer. On the other hand, the sensitizing pigment from which the electrons have transferred to the semiconductor has become an oxidized body, but is reduced by the feeding of the electrons from the second electrode through the polymer of the hole transport layer to thereby return to the original state, and at the same time, the polymer of the hole transport layer is oxidized to return again to a reducible state by the electrons fed from the second electrode. The electrons flow in such way, whereby a solar cell using the photoelectric conversion element of the present invention can be constituted.

EXAMPLES

The present invention will be explained in detail by Examples, but the scope of the present invention is not limited to these. In the following Examples, unless otherwise stated, the operations were conducted at room temperature (25° C.).

Production of Pigment-Sensitizing Photoelectric Conversion Element

Example 1

Fluorine-doped tin oxide (FTO) having a sheet resistance of 20Ω/□ (square) as a first electrode was sputtered on a glass substrate to form a transparent conductive layer (FTO) (application amount of FTO: 7 g/m² substrate), whereby a conductive glass substrate (first electrode substrate) was obtained. The glass substrate had a thickness of 1.0 mm, and the first electrode had a thickness of 1 μm. TC100 (manufactured by Matsumoto Trading Co., Ltd.): titanium diisopropoxybis(acetylacetonate) was added dropwise onto the transparent electrode layer (FTO) of the obtained conductive glass substrate, applied by a spin coat process, and heated at 450° C. for 8 minutes. By this way, a buffer layer formed of a titanium oxide thin layer (porosity C: 1.0% by volume) having a thickness 50 nm was formed on the transparent conductive film (FTO).

A titanium oxide paste (an anatase type, primary average particle size (average observed under a microscope): 18 nm, ethyl cellulose was dispersed in 10% aqueous acetylacetone) was applied on the above-mentioned buffer layer by a screen print process (application surface area: 25 mm²). The obtained coating was calcined at 200° C. for 10 minutes and at 500° C. for 15 minutes, whereby a titanium oxide porous layer having a thickness of 2.5 μm and a porosity of 60% by volume (porous semiconductor layer; porosity D: 60% by volume) was formed.

As a sensitizing pigment, A-4 (manufactured by Konica Minolta, Inc.) was dissolved in a mixed solvent of acetonitrile:t-butyl alcohol=1:1 (volume ratio) to prepare a solution of 5×10⁻⁴ mol/l. The above-mentioned FTO glass substrate on which the titanium oxide porous film had been formed was immersed in this solution at room temperature (25° C.) for 3 hours to make the porous film adsorb the pigment. By this way, a semiconductor electrode having a porous semiconductor layer (photoelectric conversion layer) carrying a pigment was obtained. The total loading amount per 1 m² of the semiconductor layer at this time was 1 mmol. Furthermore, as the sensitizing pigment used, a sensitizing pigment of the following structural formula having an absorption band at 350 to 650 nm was used.

[Chem. 28]

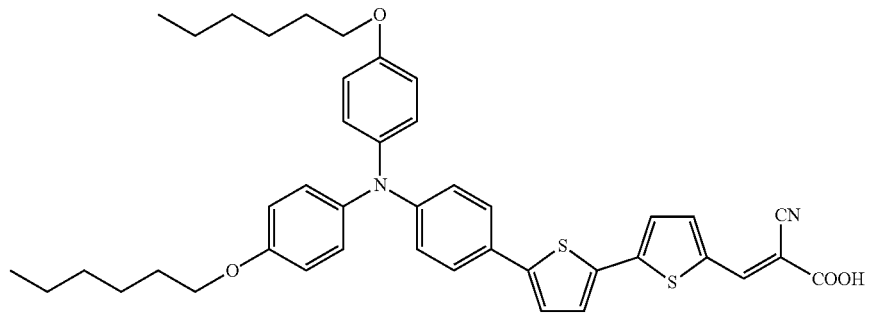

A-4

On the other hand, the above-mentioned conductive polymer precursor M1-1 (2,2'-bis[3,4-(ethylenebisoxy)thiophene]) was dissolved at a ratio of $1\times10^{-2}$ (mol/l) and Li[$(CF_3SO_2)_2$N] was dissolved at a ratio of 0.1 (mol/l) in acetonitrile to prepare a solution, 35 wt % aqueous hydrogen peroxide was then added to the solution so as to be 1 v/v %, and the semiconductor electrode prepared above was immersed. Furthermore, the semiconductor electrode was irradiated from outside with light that had come from a xenon lamp and passed through a sharp cut filter (manufactured by HOYA: S-L42), which cuts the wavelengths of 420 nm or less, for 2 minutes, whereby photopolymerization was conducted. The condition for the light irradiation was a light intensity of 22 mW/cm$^2$. When the light was irradiated under this condition, a new absorption appeared at 600 to 1100 nm, and thus it was confirmed that the conductive polymer precursor was polymerized to form a conductive polymer. The semiconductor electrode on which the hole transport layer had been formed by the polymerization was washed with acetonitrile and dried. The obtained hole transport layer was a polymerized film being insoluble in solvents.

The semiconductor electrode on which the hole transport layer had been formed (semiconductor electrode/hole transport layer) was then immersed in an acetonitrile solution containing Li[$(CF_3SO_2)_2$N] at a ratio of $15\times10^{-3}$ (mol/l) and tert-butylpyridine at a ratio of $50\times10^{-3}$ (mol/l) for 10 minutes. The obtained semiconductor electrode/hole transport layer was naturally dried, and 60 nm of gold was further deposited thereon by a vacuum deposition process to form a second electrode. By this way, photoelectric conversion element SC-1 was obtained.

Examples 2 to 18

As shown in Table 2, photoelectric conversion elements SC-2 to SC-18 were produced in a similar manner to the method for the preparation in the above-mentioned Example 1, except for the kind of the oxidizer, the kind of the conductive polymer precursor, the light irradiation, or the kind of the pigment used in Example 1.

Examples 19 to 21

SC-19 to 21 were produced in a similar manner to that for SC-1, except that the addition amount of the aqueous hydrogen peroxide used in SC-1 was changed to 0.02, 0.1, 10 v/v %, respectively.

Comparative Example 1

In the preparation of the photoelectric conversion element 1, the above-mentioned semiconductor electrode was immersed in an acetonitrile solution (electrolytic polymerization solution) containing the above-mentioned conductive polymer precursor M1-1 at a ratio of $1\times10^{-2}$ (mol/l) and Li[$(CF_3SO_2)_2$N] at a ratio of 0.1 (mol/l). The above-mentioned semiconductor electrode was used as a working electrode, a platinum wire was used as a counter electrode, Ag/Ag$^+$ (AgNO$_3$ 0.01 M) was used as a working electrode, and the retention voltage was set to −0.16 V. The voltage was retained for 30 minutes while light that had come from a xenon lamp and passed through a sharp cut filter (manufactured by HOYA: S-L42), which cuts the wavelengths of 420 nm or less, was irradiated from the direction of the semiconductor layer (xenon lamp was used, light intensity of 22 mW/cm$^2$), whereby a hole transport layer was formed on the surface of the above-mentioned semiconductor electrode. Photoelectric conversion element SC-22 was prepared in a similar manner, except that the obtained semiconductor electrode/hole transport layer was washed with acetonitrile and dried to give a charge transport layer.

Comparative Example 2

Photoelectric conversion element SC-23 was prepared in a similar manner to Example 1 of the present invention, except that, for the above-mentioned semiconductor electrode, the above-mentioned conductive polymer precursor M1-1 (2,2'-bi[3,4-(ethylenebisoxy)thiophene]) was dissolved at a ratio of $1\times10^{-2}$ (mol/l) and Li[ $(CF_3SO_2)_2$N] was dissolved at a ratio of 0.1 (mol/l) in acetonitrile to prepare a solution, and that the cobalt chloropentaneamine complex was added to the solution so as to be $1\times10^{-3}$ (mol/l) in the preparation of the photoelectric conversion element 1.

The compositions of the above-mentioned photoelectric conversion elements SC-1 to SC-23 are shown in the following Table 2.

"Evaluations of Pigment-Sensitizing Photoelectric Conversion Elements"

The following evaluations were conducted for the above-mentioned photoelectric conversion elements SC-1 to SC-22, and the results are shown in the following Table 3.

(Measurement of Initial Photoelectric Conversion Efficiency)

For the photoelectric conversion elements prepared in the above-mentioned Examples and Comparative Examples, the obtained photoelectric conversion elements were each irradiated with artificial solar light at an intensity of 100 mW/cm$^2$ through an AM filter (AM-1.5) from a xenon lamp by using a solar simulator (manufactured by EKO Instruments). Furthermore, the current-voltage property of the photoelectric conversion element at room temperature was measured by using an I-V tester, and the short-circuit current density (Jsc), open circuit voltage (Voc) and fill factor (F. F.) were measured. These values were put into the following formula to obtain a photoelectric conversion efficiency η (%).

[Math. 7]

$$\eta = 100 \times (Voc \times Jsc \times F.F.)/P \quad \text{Formula (A)}$$

Wherein P represents an incident light intensity [mW/cm$^2$], Voc represents an open circuit voltage [V], Jsc represents a short-circuit current density [mA·cm$^{-2}$], and F. F. represents a fill factor.

(Measurement of Photoelectric Conversion Efficiency after Photodeterioration Test)

Artificial solar light having an intensity of 100 mW/cm$^2$ were irradiated from a xenon lamp through an AM filter (AM-1.5) for 6 hours in an open circuit state, and the photoelectric conversion efficiency η1(%) of the photoelectric conversion element was obtained in a similar manner to that mentioned above. Furthermore, the ratio θ1/η of the photoelectric conversion efficiency after the photodeterioration η1 to the initial photoelectric conversion efficiency η was obtained. The measurements were each conducted by irradiating artificial solar light of 100 mW/cm$^2$ from a xenon lamp through an AM filter (AM-1.5) by using a solar simulator (manufactured by EKO Instruments) under a condition of a relative humidity of 60% RH under a condition of 20° C., 45° C. or 0° C. Namely, for the photoelectric conversion element, the current-voltage property was measured by using an I-V tester at room temperature, the short-circuit current (Jsc), open circuit voltage (Voc) and fill factor (F.F.) were obtained, and the photoelectric conversion efficiency (η (%)) was obtained therefrom. The conversion efficiency (η (%)) of the photoelectric conversion element was calculated based on the above-mentioned formula (A).

TABLE 2

| Photoelectric conversion element | Oxidizer | State of oxidizer after polymerization | Conductive polymer precursor | Wavelength of irradiated light | Pigment species |
|---|---|---|---|---|---|
| SC-1 | $H_2O_2$ | Liquid | M1-1 | 430 nm or less cut | A-4 |
| SC-2 | $AgNO_3$ | Solid | M1-1 | 430 nm or less cut | A-4 |
| SC-3 | Cumenehydroperoxide | Solid | M1-1 | 430 nm or less cut | A-4 |
| SC-4 | $FeCl_2$ | Solid | M1-1 | 430 nm or less cut | A-4 |
| SC-5 | HCOOH | Liquid | M1-1 | 430 nm or less cut | A-4 |
| SC-6 | MeOH | Liquid | M1-1 | 430 nm or less cut | A-4 |
| SC-7 | $H_2O_2$ | Liquid | M1-4 | 430 nm or less cut | A-4 |
| SC-8 | $H_2O_2$ | Liquid | M1-21 | 430 nm or less cut | A-4 |
| SC-9 | $H_2O_2$ | Liquid | M1-26 | 430 nm or less cut | A-4 |
| SC-10 | $H_2O_2$ | Liquid | M1-1 | 430 nm or less cut | A-44 |
| SC-11 | $H_2O_2$ | Liquid | M1-1 | 430 nm or less cut | B-11 |
| SC-12 | $H_2O_2$ | Liquid | M1-1 | 430 nm or less cut | B-27 |
| SC-13 | $H_2O_2$ | Liquid | M1-1 | 430 nm or less cut | C-1 |
| SC-14 | $H_2O_2$ | Liquid | M1-1 | 430 nm or less cut | C-3 |
| SC-15 | $H_2O_2$ | Liquid | M1-1 | 430 nm or less cut | C-14 |
| SC-16 | $H_2O_2$ | Liquid | M1-1 | 430 nm or less cut | D-1 |
| SC-17 | $H_2O_2$ | Liquid | M1-1 | 430 nm or less cut | D-2 |
| SC-18 | $H_2O_2$ | Liquid | M1-1 | 430 nm or less cut | A-4 |
| SC-19 | $H_2O_2$ | Liquid | M1-1 | 430 nm or less cut | A-4 |
| SC-20 | $H_2O_2$ | Liquid | M1-1 | 430 nm or less cut | A-4 |
| SC-21 | $H_2O_2$ | Liquid | M1-1 | 430 nm or less cut | A-4 |
| SC-22 | None | — | M1-1 | 430 nm or less cut | A-4 |
| SC-23 | Cobaltchloropentaneamine complex | Solid | M1-1 | 430 nm or less cut | A-4 |

TABLE 3

| Photoelectric conversion element | Thickness of porous film $(Ft_{SC})/\mu m$ | $A_{1000}$: Absorbance of element at 1,000 nm | $[Ox]/[M]$ | Short circuit current $(mA \cdot cm^{-2})$ | Open circuit voltage (mV) | Fill factor | Photoelectric conversion efficiency of photoelectric conversion element (η(%)) Before photodeterioration (%) | After photodeterioration (%) | Efficiency rate before and after photodeterioration |
|---|---|---|---|---|---|---|---|---|---|
| SC-1 | 3.0 | 0.59 | 10 | 9.62 | 821 | 0.61 | 4.82 | 3.98 | 82.61 |
| SC-2 | 3.1 | 0.50 | 10 | 9.11 | 814 | 0.60 | 4.45 | 3.53 | 79.34 |
| SC-3 | 3.0 | 0.41 | 10 | 8.80 | 811 | 0.61 | 4.35 | 3.35 | 76.95 |
| SC-4 | 3.0 | 0.41 | 10 | 8.45 | 854 | 0.58 | 4.19 | 3.09 | 73.83 |
| SC-5 | 3.1 | 0.47 | 10 | 8.61 | 839 | 0.60 | 4.33 | 3.26 | 75.21 |
| SC-6 | 3.1 | 0.51 | 10 | 8.79 | 822 | 0.62 | 4.48 | 3.30 | 73.67 |
| SC-7 | 3.0 | 0.60 | 10 | 8.98 | 834 | 0.60 | 4.49 | 3.37 | 75.00 |
| SC-8 | 3.1 | 0.57 | 10 | 8.49 | 932 | 0.55 | 4.35 | 3.22 | 73.99 |
| SC-9 | 3.2 | 0.55 | 10 | 7.88 | 871 | 0.62 | 4.26 | 2.97 | 69.79 |
| SC-10 | 2.9 | 0.40 | 10 | 8.12 | 845 | 0.60 | 4.12 | 2.81 | 68.26 |
| SC-11 | 3.0 | 0.63 | 10 | 7.93 | 871 | 0.59 | 4.08 | 2.65 | 65.03 |
| SC-12 | 3.1 | 0.61 | 10 | 7.31 | 854 | 0.63 | 3.93 | 2.56 | 65.09 |
| SC-13 | 3.1 | 0.62 | 10 | 8.67 | 810 | 0.59 | 4.14 | 2.98 | 71.92 |
| SC-14 | 3.0 | 0.61 | 10 | 6.98 | 955 | 0.59 | 3.93 | 2.54 | 64.58 |
| SC-15 | 3.1 | 0.57 | 10 | 7.73 | 791 | 0.62 | 3.79 | 2.39 | 63.04 |
| SC-16 | 2.9 | 0.59 | 10 | 7.12 | 809 | 0.63 | 3.63 | 2.37 | 65.31 |
| SC-17 | 2.9 | 0.52 | 10 | 7.75 | 810 | 0.63 | 3.95 | 2.41 | 60.94 |
| SC-18 | 3.1 | 0.54 | 10 | 7.23 | 794 | 0.62 | 3.56 | 2.18 | 61.25 |
| SC-19 | 2.9 | 0.41 | 0.2 | 8.03 | 842 | 0.61 | 4.12 | 2.77 | 67.16 |
| SC-20 | 3.0 | 0.68 | 1 | 8.85 | 785 | 0.64 | 4.45 | 3.71 | 83.44 |
| SC-21 | 3.1 | 1.03 | 100 | 8.14 | 798 | 0.63 | 4.09 | 3.00 | 73.31 |
| SC-22 | 2.9 | 0.35 | — | 8.24 | 821 | 0.58 | 3.92 | 1.02 | 26.00 |
| SC-23 | 3.0 | 0.22 | 0.1 | 3.22 | 764 | 0.51 | 1.25 | 0.31 | 24.71 |

The invention claimed is:

1. A photoelectric conversion element having:
a substrate, a first electrode, a photoelectric conversion layer containing a semiconductor and a sensitizing pigment, a hole transport layer having a conductive polymer, and a second electrode,
wherein the hole transport layer is formed by bringing the photoelectric conversion layer into contact with a conductive polymer precursor in the presence of an oxidizer, and irradiating the sensitizing pigment with light to conduct a polymerization of the conductive polymer precursor, and
the polymerization consists essentially of a photochemical polymerization, wherein the photochemical polymerization is conducted without applying a voltage to the first electrode and the second electrode.

2. The photoelectric conversion element according to claim 1, wherein the conductive polymer precursor and the oxidizer are brought into contact at a ratio of the following mathematical formula (1):

$$0.1 < [Ox]/[M] \tag{1}$$

wherein in the mathematical formula (1), [Ox] is the molar concentration of the oxidizer; and [M] is the molar concentration of the conductive polymer precursor.

3. The photoelectric conversion element according to claim 1, wherein the oxidizer is hydrogen peroxide, oxygen, methanol, a metal salt or an organic peroxide.

4. The photoelectric conversion element according to claim 1, wherein the oxidizer has a standard electrode potential ($E^0_{(OX)}$) of from −0.5 to +2.0 (V).

5. The photoelectric conversion element according to claim 1, wherein the oxidizer becomes a gas compound or a liquid compound by the light irradiation.

6. The photoelectric conversion element according to claim 1, wherein the conductive polymer precursor has a repeating unit represented by the following monomer formula 1:

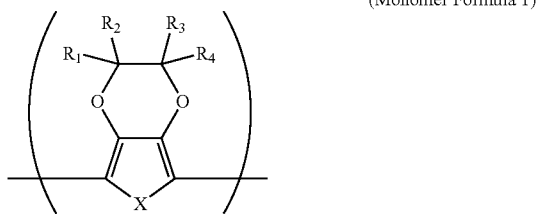
(Monomer Formula 1)

wherein in the monomer formula 1, X represents S, NR or O, R is either of hydrogen and an alkyl group, $R_1$ to $R_4$ are each independently a hydrogen atom, a halogen atom, a straight chain or branched alkyl group having 1 to 30 carbon atom(s), a cycloalkyl group having 3 to 10 carbon atoms, an alkoxy group having 1 to 30 carbon atom(s), a polyethylene oxide group having 2 to 30 carbon atoms, or a substituted or unsubstituted cyclic compound-containing group having 4 to 30 carbon atoms.

7. The photoelectric conversion element according to claim 1, wherein the sensitizing pigment has a carboxyl group.

8. The photoelectric conversion element according to claim 1, wherein the sensitizing pigment is represented by the general formula (1):

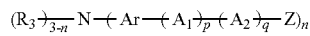

wherein in the general formula (1),
$R_3$s each independently represents a hydrogen atom, a halogen atom, a substituted or unsubstituted alkyl group, a substituted or unsubstituted alkoxy group, a substituted or unsubstituted alkenyl group, a substituted or unsubstituted alkynyl group, a substituted or unsubstituted aryl group, an amino group, a cyano group, or a substituted or unsubstituted heterocyclic group, Ar represents a bivalent cyclic compound group,
$A_1$ and $A_2$ each independently represents a single bond, a bivalent saturated or unsaturated hydrocarbon group, a substituted or unsubstituted alkylene group, an arylene group, or a bivalent heterocyclic group,
Z is an organic group having an acidic group, an alkoxysilane or a halogenated silane,
p and q are each independently an integer of 0 or more and 6 or less,
n is an integer of 1 or more and 3 or less,
when n is 1, the two $R_3$s may be different from each other, and $R_3$ may connect to another substituent to form a cyclic structure, and when n is 2 or more, each of the plural Ars, $A_1$s, $A_2$s and Zs may be different from each other.

9. The photoelectric conversion element according to claim 8, wherein the sensitizing pigment is such that n=2 in the general formula (1).

10. The photoelectric conversion element according to claim 1, wherein the semiconductor is titanium oxide.

11. The photoelectric conversion element according to claim 1, wherein the photoelectric conversion layer has an absorbance at 1,000 nm ($A_{1000}$) that satisfies the following mathematical formula (2):

$$A_{1000} \geq FT_{SC}/8 \tag{2}$$

wherein in the above-mentioned mathematical formula (2), $A_{1000}$ is the absorbance at 1,000 nm of the photoelectric conversion layer; and
$FT_{SC}$ is the film thickness (μm) of the photoelectric conversion layer.

12. A method for producing a photoelectric conversion element having a substrate, a first electrode, a photoelectric conversion layer containing a semiconductor and a sensitizing pigment, a hole transport layer having a conductive polymer, and a second electrode, the method including the steps of:
step (1): forming the photoelectric conversion layer on the substrate having the first electrode on the surface,
step (2): bringing the conductive polymer precursor into contact with the photoelectric conversion layer in the presence of oxidizer,
step (3): irradiating the sensitizing pigment with light in the presence of the oxidizer to conduct a photochemical polymerization of the conductive polymer precursor to thereby form the hole transport layer, and
step (4): forming the second electrode,
wherein the photochemical polymerization is conducted without applying a voltage to the first electrode and the second electrode.

13. The method for producing a photoelectric conversion element according to claim 12, wherein, in the step (2), the conductive polymer precursor and the oxidizer are brought into contact at a ratio of the following mathematical formula (1):

$$0.1 < [Ox]/[M] \tag{1}$$

wherein in the mathematical formula (1), [Ox] is the molar concentration of the oxidizer; and [M] is the molar concentration of the conductive polymer precursor.

14. The method according to claim 12, wherein the oxidizer is hydrogen peroxide, a metal salt or an organic peroxide.

15. The method according to claim 12, wherein the oxidizer has a standard electrode potential ($E^0_{(OX)}$) of from −0.5 to +2.0 (V).

16. The method according to claim 12, wherein the oxidizer becomes a gas compound or a liquid compound by the light irradiation.

17. The method according to claim 12, wherein the conductive polymer has a repeating unit represented by the following general formula (2)

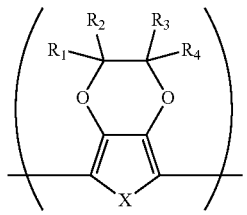

General formula (2)

wherein in the general formula (2), X represents S, NR or O, R is either of hydrogen and an alkyl group, $R_1$ to $R_4$ are each independently a hydrogen atom, a halogen atom, a straight chain or branched alkyl group having 1 to 30 carbon atom(s), a cycloalkyl group having 3 to 10 carbon atoms, an alkoxy group having 1 to 30 carbon atom(s), a polyethylene oxide group having 2 to 30 carbon atoms, or a substituted or unsubstituted cyclic compound-containing group having 4 to 30 carbon atoms.

* * * * *